US012473270B2

(12) United States Patent
Benita et al.

(10) Patent No.: US 12,473,270 B2
(45) Date of Patent: Nov. 18, 2025

(54) CB1R RECEPTOR BLOCKERS WITH ACYCLIC BACKBONES

(71) Applicant: YISSUM RESEARCH DEVELOPMENT COMPANY OF THE HEBREW UNIVERSITY OF JERUSALEM LTD., Jerusalem (IL)

(72) Inventors: Simon Benita, Tel Aviv (IL); Taher Nassar, Kfar Tur'an (IL); Joseph Tam, Jerusalem (IL); Shira Hirsh, Jerusalem (IL)

(73) Assignee: Yissum Research Development Company of the Hebrew University of Imersualem Ltd. (IL)

( * ) Notice: Subject to any disclaimer, the term of this patent is extended or adjusted under 35 U.S.C. 154(b) by 1050 days.

(21) Appl. No.: 17/422,733

(22) PCT Filed: Jan. 15, 2020

(86) PCT No.: PCT/IL2020/050062

§ 371 (c)(1),
(2) Date: Jul. 13, 2021

(87) PCT Pub. No.: WO2020/148760

PCT Pub. Date: Jul. 23, 2020

(65) Prior Publication Data

US 2022/0119365 A1 Apr. 21, 2022

Related U.S. Application Data

(60) Provisional application No. 62/792,531, filed on Jan. 15, 2019, provisional application No. 62/936,819, filed on Nov. 18, 2019, provisional application No. 62/942,383, filed on Dec. 2, 2019.

(51) Int. Cl.

| | |
|---|---|
| ***C07D 401/12*** | (2006.01) |
| ***A61P 1/04*** | (2006.01) |
| ***A61P 3/04*** | (2006.01) |
| ***A61P 3/10*** | (2006.01) |
| ***A61P 11/06*** | (2006.01) |
| ***A61P 13/12*** | (2006.01) |
| ***A61P 15/00*** | (2006.01) |
| ***C07C 233/13*** | (2006.01) |
| ***C07C 235/06*** | (2006.01) |
| ***C07C 235/20*** | (2006.01) |
| ***C07C 255/58*** | (2006.01) |
| ***C07D 231/14*** | (2006.01) |
| ***C07D 403/12*** | (2006.01) |
| ***C07D 473/00*** | (2006.01) |
| ***C07D 473/26*** | (2006.01) |
| ***C07D 473/32*** | (2006.01) |
| ***C07D 491/044*** | (2006.01) |

(52) U.S. Cl.

CPC .............. *C07D 401/12* (2013.01); *A61P 3/04* (2018.01); *A61P 3/10* (2018.01); *C07D 231/14* (2013.01); *C07D 473/00* (2013.01); *C07D 491/044* (2013.01)

(58) Field of Classification Search

CPC ................ C07D 401/12; C07D 231/14; C07D 473/00; C07D 473/26; C07D 473/32; C07D 491/044; C07D 403/12; A61P 3/04; A61P 3/10; A61P 1/04; A61P 11/06; A61P 13/12; A61P 15/00; C07C 233/13; C07C 235/06; C07C 235/20; C07C 255/58

See application file for complete search history.

(56) References Cited

U.S. PATENT DOCUMENTS

| | | | |
|---|---|---|---|
| 6,509,367 | B1 | 1/2003 | Martin et al. |
| 6,972,295 | B2 | 12/2005 | Hagmann et al. |
| 2003/0199536 | A1 | 10/2003 | Thomas et al. |
| 2007/0213302 | A1 | 9/2007 | McElroy et al. |

FOREIGN PATENT DOCUMENTS

| | | | |
|---|---|---|---|
| WO | 2004037823 | | 5/2004 |
| WO | 2006133926 | | 12/2006 |
| WO | 2015162452 | A1 | 10/2015 |
| WO | 2018119076 | | 6/2018 |

OTHER PUBLICATIONS

RN362007-43-0, registry database compound, 2001.*
RN362007-43-0, registry database compound properties, 2001.*
Coronaryheartdisease-Prevention, 2024, https://www.nhs.uk/conditions/coronary-heart-disease/prevention/#:~:text=Be%20more%20physically%20active&text=Regular%20exercise%20will%20make%20your,of%20having%20a%20heart%20attack.*
ObesityPrevention, 2024, https://www.hopkinsmedicine.org/health/conditions-and-diseases/obesity/preventing-obesity#:~:text=Improving%20eating%20habits%20and%20increasing,of%20fruits%20and%20vegetables%20daily.*
Cristina Fernandez-Fernandez et al., Description of a Bivalent Cannabinoid Ligand with Hypophagic Properties, Arch. Pharm. Chem. Life Sci., 2013, vol. 346, pp. 171-179.
Luc F. Van Gaal et al., Effects of the Cannabinoid-1 Receptor Blocker Rimonabant on Weight Reduction and Cardiovascular Risk Factors in Overweight Patents: 1-year Experience from the RIO—Europe Study, Lancet, vol. 365, 2005, pp. 1389-1397.
F. Xavier Pi-Sunyer et al., J. Effect of Rimonabant, a Cannabinoid-1 Receptor Blocker, on Weight and Cardiometabolic Risk Factors in Overweight or Obese Patients: RIO—North America: a Randomized Controlled Trial, JAMA, vol. 295, 2006, pp. 761-775.
Jean-Pierre Despres et al., Effects of Rimonabant on Metabolic Risk Factors in Overweight Patients with Dyslipidemia., N. Engl. J. Med., vol. 353, 2005, pp. 2121-2134.
A.S. Wierzbicki et al., Rimonabant Improves Cholesterol, Insulin Resistance and Markers of Non-Alcoholic Fatty Liver in Morbidly Obese Patients: a Retrospective Cohort Study, Int. J. Clin. Pract., vol. 65, 2011, pp. 713-715.

(Continued)

*Primary Examiner* — Sun Jae Yoo
(74) *Attorney, Agent, or Firm* — McAndrews, Held & Malloy, Ltd.

(57) ABSTRACT

The invention generally concerns a novel class of CB 1 receptor binding molecules and uses thereof.

15 Claims, 19 Drawing Sheets

(56) References Cited

OTHER PUBLICATIONS

P. Hollander, Endocannabinoid Blockade for Improving Glycemic Control and Lipids in Patients With Type 2 Diabetes Mellitus, The American Journal of Medicine, vol. 120, 2007, pp. S18-28, S29-32.
M.D. Randall et al., Rimonabant in Obese Patients with Type 2 Diabetes, Lancet, vol. 369, 2007, p. 555.
Hycon-Kyu Lee et al., The Current Status and Future Perspectives of Studies of Cannabinoid Receptor 1 Antagonists as Anti-Obesity Agents, Current Topics in Medicine Chemistry, vol. 9, 2009, pp. 482-503.
Zhensheng Ding et al., A Succinct Synthesis of the Vaulted Biaryl Ligand Vanol via a Dienone-Phenol Rearrangement, Chemistry—an Asian Journal, vol. 6, No. 8, May 20, 2011, pp. 2130-2146.
Su Z. et al., Dynamics of Anilinium Radical Alpha-Heterolytic Fragmentation Process, Electrofugal Group, Substituent, and Medium Effects on Desilylation, Decarbonxylation, and Retro-Aldol Cleavage Pathways, Journal of the American Chemical Society, vol. 120, No. 41, 1998, pp. 10676-10686.
Chaonan Dong et al., Pd-Catalyzed Ligand-Free Suzuki Reaction of [Beta]-Substituted Allylic Halides With Arylboronic Acids in Water, RSC Adv., vol. 4, No. 22, 2014, pp. 11152-11158.
Kassem Beydoun et al., Ruthenium-Catalyzed Reductive Methylation of Imines Using Carbon Dioxide and Molecular Hydrogen, Angewandte Chemie, International Edition, vol. 53, No. 41, Aug. 21, 2014, pp. 11010-11014.
MA. Elena Y. Francisco et al., Synthesis and Structure-Activity Relationships of Amide and Hydrazide Analogues of the Cannabinoid CB 1 Receptor Antagonist N-(Piperidinyl)-5-(4-chlorophenyl)-1-(2,4-dichlorophenyl)-4-methyl-1 H-pyrazole-3-carboxamide (SR141716), Journal of Medicinal Chemistry, vol. 45, No. 13, Jun. 2002, pp. 2708-2719.
Alan Fulp et al., Towards Rational Design of Cannabinoid Receptor 1 (CB1) Antagonists for Peripheral Selectivity, Bioorganic & Medicinal Chemistry Letters, Pergamon, Amsterdam, NL, vol. 21, No. 19, Aug. 4, 2011, pp. 5711-5714.
Yahan Zhang et al., Synthesis and Biological Evaluation of Bivalent Ligands for the Cannabinoid 1 Receptor, Journal of Medicinal Chemistry, American Chemical Society, vol. 53, Oct. 14, 2010, pp. 7048-7060.
M.J. Genin et al., Novel 1,5-Diphenylpyrazole Nonnucleoside Hiv-1 Reverse Transcriptase Inhibitors with Enhanced Activity Versus the Delavirdine-Resistant P2361 Mutant: Lead Identification and Sar of 3- and 4-Substituted Derivatives, Journal of Medicinal Chemistry, American Chemical Society, vol. 43, Jan. 1, 2000, pp. 1034-1040.
BF Thomas et al., Synthesis of Long-Chain Amide Analogs of the Cannabinoid CB1 Receptor Antagonist N-(piperidinyl)-5-(4-chlorophenyl)-1-(2,4-dichlorophenyl)-4-methyl-1H-pyrazole-3-car Boxamide (SR141716) with Unique Binding Selectivities and Pharmacological Activities, Biorganic & Medicinal Chemistry: A Tetrahedron Publication for the Rapid Dissemination of Full Original Research Papers and Critical Reviews on Biomolecular Chemistry, Medicinal Chemistry and Related Disciplines, Elsevier, NL, vol. 13, No. 18, Sep. 15, 2005, pp. 5643-5474.
Elena Cichero et al., Exploring the Binding Features of Rimonabant Analogues and Acyclic CB1 Antagonists: Docking Studies and QSAR Analysis, Journal of Molecular Modeling, Springer, DE, vol. 14, No. 12, Aug. 12, 2008, pp. 1131-1145.
Lan et al., Structure-Activity Relationships of Pyrazole Derivatives as Cannabinoid Receptor Antagonists, Journal of Medicinal Chemistry, American Chemical Society, vol. 42, No. 4, Jan. 1, 1999, pp. 769-776.
K.S. Song et al., Synthesis and Structure-Activity Relationship of Novel Diarylpyrazole imide Analogues as CBI Cannabinoid Receptor Ligands, Bioorganic & Medicinal Chemistry: A Tetrahedron Publication for the Rapid Dissemination of Full Original Research Papers and Critical Reviews on Biomolecular Chemistry, Medicinal Chemistry and Related Disciplines, Elsevier, NL, vol. 17, No. 8, Apr. 15, 2009, pp. 3080-3092.
D.A. Griffith et al., Discovery of 1-[9-(4-Clorophenyl)-8-(2-clorophenyl)-9H-purin-6-yl]-4-ethylamino-biperidine-4carb oxlic Acid Amide Hydrochloride (CP-945,598), a Novel, Potent, and Selective Cannabinoid Type 1 Receptor, Journal of Medicinal Chemistry, American Chemical Society, vol. 52, No. 2, Dec. 22, 2008, pp. 234-237.
George S. Amato et al., Blocking Alcoholic Steatosis in Mice with a Peripherally Restricted Purine Antagonist of the Type 1 Cannabinoid Receptor, Journal of Medicinal Chemistry, vol. 61, No. 10, Apr. 24, 2018, pp. 4370-4385.
Guozheng Huang et al., Design, Synthesis and in Vitro Evaluation of Novel Uni- and Bivalent Ligands for the Cannabinoid Receptor Type 1 with Variation of Spacer Length and Structure, Biorganic & Medicinal Chemistry Letters, vol. 24, 2014, pp. 4209-4214.
Pradip K. Sasmal et al., Novel Pyrazole-3-Carboxamide Derivatives as Cannabinoid-1 (CB1) Antagonists: Journey from Non-Polar to Polar Amides, Biorganic & Medicinal Chemistry Letters, vol. 21, 2011, pp. 562-568.
Mario Alvarado et al., Antiobesity Designed Multiple Ligands: Synthesis of Pyrazole Fatty Acid Amides and Evaluation as Hypophagic Agents, Biorganic & Medicinal Chemistry, vol. 16, 2008, pp. 10098-10105.
STN Search Report, STN Registry, Chemical Abstract Service, Columbus, Ohio, US, pp. 8-10.

* cited by examiner

Ambulatory Activity (Counts, Y)
150
120
90
60
30
0
Vehicle
R 10mg/kg
Vehicle
10mg/kg
20mg/kg
50mg/kg
B2
HU210

Ambulatory Activity (Counts, Y)
8000
6000
4000
2000
0
Vehicle
R 10mg/kg
Vehicle
10mg/kg
20mg/kg
50mg/kg
B2
HU210

Wheel Running (m)
4000
3000
2000
1000
0
Vehicle
R 10mg/kg
Vehicle
10mg/kg
20mg/kg
50mg/kg
B2
HU210

Daily Food Intake (cal)
(Cal)
40
30
20
10
0
-10
0
10
20
30
Day
STD-Veh
HFD-Veh
HFD-R
HFD-B2

Total Food Intake (cal)
(Cal)
800
600
400
200
0
STD
HFD
STD-Veh
HFD-Veh
HFD-R
HFD-B2

Fasting Plasma Glucose
mg/dL
150
100
50
0
STD
HFD
STD-Veh
HFD-Veh
HFD-R
HFD-B2

GTT-Glucose
mg/dL
500
400
300
200
100
0
0
50
100
150
STD-Veh
HFD-Veh
HFD-R
HFD-B2

Serum Insulin Level
ng/mL
8
6
4
2
0
STD
HFD
STD-Veh
HFD-Veh
HFD-R
HFD-B2

Ambulatory Activity (Counts,Y)
Wheel running (m )
Veh
IDB
07:00
19:00
07:00
Light
Dark
Total
0
50
100
150
200
10
20
30
40

GTT mg/dL
Time (min)

AUG GTT mg/dL/h
VEH
IDB

ITT Glucose (%)
Time (min)

ITT mg/dL
Time (min)

AUG ITT mg/dL/h
Veh
IDB

ITT Slop Change
Veh
IDB

Fasting Glucose mg/dL
Veh
IDB

Plasma glucose md/dL
Veh
IDB

Urine glucose µg/h
Veh
IDB

Cholesterol mg/dl
250
200
150
100
50
0
Veh
IDB
*

TG mg/dL
250
200
150
100
50
0
Veh
IDB

HDL mg/dL
250
200
150
100
50
0
Veh
IDB
*

LDL-C mg/dL
150
100
50
0
Veh
IDB
*

HDL/LDL
Cholesterol ratio
3
2
1
0
Veh
IDB
*

CB1R RECEPTOR BLOCKERS WITH ACYCLIC BACKBONES

CROSS-REFERENCE TO RELATED APPLICATIONS

The present application is a National Phase Entry of PCT International Application No. PCT/IL2020/050062 which was filed on Jan. 15, 2020, which claims priority to provisional patent application Ser. No. 62/792,531, filed Jan. 15, 2019, provisional patent application Ser. No. 62/936,819, filed Nov. 18, 2019, and provisional patent application Ser. No. 62/942,383, filed Dec. 2, 2019, all of which are hereby incorporated by reference in their entireties.

TECHNOLOGICAL FIELD

The invention generally concerns novel peripherally restricted $CB_1$ receptor blockers and uses thereof.

BACKGROUND

Obesity is a chronic disease reaching epidemic proportions, with more than one-third (34.9% or 78.6 million) of U.S. adults considered obese. Obesity has been described as a catalyst for a number of conditions, most notably cardiovascular disease, type 2 diabetes mellitus (T2DM) and non-alcoholic fatty liver disease (NAFLD). While several metabolic factors have been linked to the development of obesity, the molecular mechanisms involved in metabolism are not fully understood.

Endocannabinoids (eCBs) are endogenous lipid ligands that interact with the same cannabinoid receptors, $CB_1$ and $CB_2$, which also recognize $\Delta^9$-tetrahydrocannabinol (THC), the psychoactive component of cannabis and mediate its biological effects. By activating $CB_1$ receptors, eCBs increase appetite (the 'munchies') and lipogenesis in adipose tissue and liver and induce insulin resistance and dyslipidemia. These effects suggest that an overactive eCB/$CB_1$ receptor system contributes to the development of visceral obesity, T2DM and their complications. Accordingly, this has prompted pharmaceutical companies to develop drugs that block $CB_1$ receptors as potential treatment for obesity, T2DM and NAFLD. The first such compound, rimonabant [globally-acting $CB_1$ receptor antagonist ($1^{st}$ generation)], was effective not only in reducing body weight in obese and overweight individuals, but also in ameliorating the associated metabolic abnormalities, including fatty liver, insulin resistance and T2DM [1-6]. However, due to neuropsychiatric side effects (such as, depression, anxiety and suicidal ideation) rimonabant was withdrawn from the market worldwide, and $CB_1$ receptors are no longer considered as a valid therapeutic target for obesity, T2DM or NAFLD.

REFERENCES

[1] Van Gaal, L. F., Rissanen, A. M., Scheen, A. J., Ziegler, O. & Rossner, S. Effects of the cannabinoid-1 receptor blocker rimonabant on weight reduction and cardiovascular risk factors in overweight patients: 1-year experience from the RIO-Europe study. *Lancet* 365, 1389-1397 (2005).

[2] Pi-Sunyer, F. X., Aronne, L. J., Heshmati, H. M., Devin, J. & Rosenstock, J. Effect of rimonabant, a cannabinoid-1 receptor blocker, on weight and cardiometabolic risk factors in overweight or obese patients: RIO-North America: a randomized controlled trial. *JAMA* 295, 761-775 (2006).

[3] Despres, J. P., Golay, A., Sjostrom, L. & Rimonabant in Obesity-Lipids Study, G. Effects of rimonabant on metabolic risk factors in overweight patients with dyslipidemia. *N Engl J Med* 353, 2121-2134 (2005).

[4] Wierzbicki, A. S., et al. Rimonabant improves cholesterol, insulin resistance and markers of non-alcoholic fatty liver in morbidly obese patients: a retrospective cohort study. *Int J Clin Pract* 65, 713-715 (2011).

[5] Hollander, P. Endocannabinoid blockade for improving glycemic control and lipids in patients with type 2 diabetes mellitus. *The American journal of medicine* 120, S18-28; discussion S29-32 (2007).

[6] Randall, M. D., Kendall, D. A., Bennett, A. J. & O'Sullivan, S. E. Rimonabant in obese patients with type 2 diabetes. *Lancet* 369, 555 (2007).

[7] US 2003/0199536

GENERAL DESCRIPTION

The inventors of the technology disclosed herein have developed a methodology whereby peripherally restricted $CB_1$ receptor antagonists retain the therapeutic benefits of globally acting $CB_1$ receptor blockers without causing CNS-mediated side effects; thus, reviving the earlier prospect of $CB_1$ receptor blockade for the treatment of metabolic syndromes. To that end, the inventors have designed a new class of novel compounds that do not penetrate the blood-brain-barrier and thus block the $CB_1$ receptor only in peripheral organs, such as the adipose tissue, the liver, in skeletal muscles, pancreatic β-cells and the kidneys, without causing centrally-mediated side effects.

The inventors have also demonstrated that lipophilic compounds that bind a $CB_1$ receptor and which are P-gp substrates; and/or have a brain/plasma ratio below 0.3; and/or have a diphenyl ethylene or diphenyl methylene moiety exhibit therapeutic benefits without causing CNS-mediated side effects.

This novel class of compounds exhibited efficacy in affecting several features of the metabolic syndrome.

Thus, in a first aspect of the presently disclosed invention, there is provided a lipophilic derivative of cannabinoid having a calculated Log P (partition coefficient between n-octanol and water) value ranging from 3 and 17.

The invention further provides a $CB_1$ receptor-binding lipophilic compound, wherein:

the compound is a P-glycoprotein (P-gp) substrate; and/or the compound has a brain/plasma ratio below 0.3; and/or the compound having a diphenyl ethylene or diphenyl methylene moiety of formula (A):

(A)

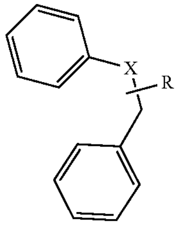

wherein

R is a substituent or a ring structure as defined in any of the structures below, X is a carbon containing group (C, C═, CH), a nitrogen containing group (N, N═, NH) or is absent; provided that R is different from H.

In a compound of formula (A), each of the phenyl groups, independently of the other, may or may not be substituted by 1, 2, 3, 4 or 5 same or different substituents.

In some embodiments, the $CB_1$ receptor-binding lipophilic compound is a P-gp substrate.

In some embodiments, the $CB_1$ receptor-binding lipophilic compound has a brain/plasma ratio below 0.3.

In some embodiments, the $CB_1$ receptor-binding lipophilic compound comprises a diphenyl ethylene or diphenyl methylene moiety of formula (A), which may optionally be any of the compounds of general formulae (I) through (XXXXI) or any of the compounds specifically disclosed.

As indicated, compounds of the invention exhibit therapeutic benefits without causing CNS-mediated side effects. The absence of a CNS-mediated side effects is due, inter alia, to an interaction between compounds of the invention and P-gp (thus regarded as "P-gp substrates") which limits or diminishes their penetration to the brain. The absence of or the diminished penetration to the brain may be qualitatively and, in some instances, quantitatively determined by means known in the art.

The brain-plasma concentration ratio representing one of the tools available for estimation of CNS pharmacokinetics is a parameter that indicates the blood-brain barrier availability of compounds. This value describes the free drug concentration of a compound in the brain, which is believed to be the parameter that causes the relevant pharmacological response at the target site. As indicated, compounds of the invention have exhibited substantially no brain penetration. Within the context of this aspect of the invention, the expression "substantially no brain penetration" refers no brain penetration to a brain-plasma ratio ranging from 0.0001 and 0.3. Compounds of the invention are further characterized by comprising a diphenyl ethylene or diphenyl methylene moiety of formula (A), as defined herein. In some embodiments, the compound of formula (A) is a compound of formula (I), as disclosed herein.

The invention further provides a lipophilic CB1 receptor-binding compound having a calculated Log P (partition coefficient between n-octanol and water) value ranging from 3 and 17, wherein the compound comprising a diphenyl ethylene or diphenyl methylene moiety of formula (A), as defined herein, or is a compound of formula (I), as disclosed herein.

The invention further provides a compound of formula (I):

(I)

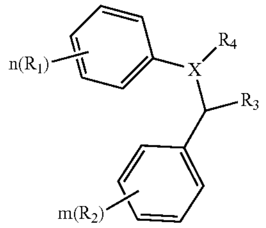

wherein each of $R_1$ and $R_2$, independently of the other, is a group selected from —H, halide, —CN, —$C_1$-$C_5$alkyl-OH and —OH;

each of n and m, independently of the other, is an integer between 0 and 5, designating the number of substituents on the ring;

X is selected from nitrogen and —CH—; or X—$R_4$ may optionally be N═$R_4$ or C═$R_4$;

$R_3$ is selected from H, a carbon containing group comprising between 1 and 3 carbon atoms, being optionally substituted, and a nitrogen atom or a nitrogen containing group;

$R_4$ is selected from a carbon containing group comprising between 1 and 3 carbon atoms, being optionally substituted, and a nitrogen atom or a nitrogen containing group;

or $R_3$ and $R_4$ together with atoms to which they are bonded (carbon atom and X, respectively) form a 5- or 6-membered carbocyclic ring optionally containing between 1 and 3 heteroatoms selected from N, O and S;

or $R_3$ and $R_4$ together with the atoms to which they are bonded form a fused ring system optionally containing between 1 and 6 heteroatoms selected from N, O and S.

In some embodiments, X is N.

In some embodiments, X—$R_4$ is C═$R_4$.

In some embodiments, X—$R_4$ is N═$R_4$.

In some embodiments, X is a nitrogen atom and $R_4$ is a nitrogen containing group. In such embodiments, moiety X—$R_4$ may thus be selected from —N—NH—, —N═N— and N—N═(wherein in the selection the N on the left is X and the N on the right is $R_4$).

In some embodiments, $R_3$ is a carbon containing group and $R_4$ is a nitrogen containing group.

In some embodiments, $R_3$ and $R_4$ together with the atoms to which they are bonded form a 6-membered carbocyclic ring optionally containing 1 or 2 nitrogen atoms.

In some embodiments, $R_3$ and $R_4$ together with the atoms to which they are bonded form a 5-membered carbocyclic ring optionally containing 1 or 2 nitrogen atoms.

In some embodiments, $R_3$ and $R_4$ together with the atoms to which they are bonded form a fused ring system optionally containing 1, 2, 3, 4, 5, or 6 heteroatoms such as nitrogen atoms.

In some embodiments, the fused ring system is a two-ring fused system comprising a 5-membered ring that is fused to a 5-membered ring, or fused to a 6-membered ring, or fused to a 7-membered ring, or fused to a 8-membered ring. In some embodiments, the fused ring system is a two-ring fused system comprising a 5-membered ring that is fused to a 6-membered ring, wherein the fused system comprises 1, 2, 3, 4, or 5 heteroatoms. The fused system may further be substituted.

In some embodiments, the compound is of the general formula (II):

(II)

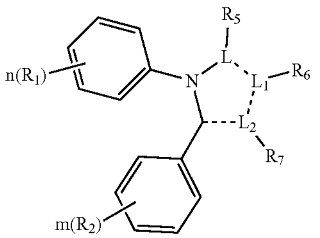

wherein one of L, $L_1$ and $L_2$ is a nitrogen atom and the others of L, $L_1$ and $L_2$ are each a carbon atom (being selected from C, CH or $CH_2$);

each of $R_5$, $R_6$ and $R_7$, independently of the other, may be selected from —H, —$C_1$-$C_3$alkyl, —C(═O)—OH, —C(═O)—O—$R_8$, —C(═O)—NR'$R_8$, halide, —CN, —OH, and —NR'R"; or one of R5 and R6 or R6 and R7 together with the atoms to which they bond may form a 5-, 6-, 7- or 8-membered carbocyclic ring optionally containing between 1 and 3 heteroatoms selected from N, O and S;

the 5-, 6-, 7- or 8-membered carbocyclic ring is further optionally substituted by at least one functionality selected from H, —$C_1$-$C_{25}$alkyl, —$C_2$-$C_{25}$alkenyl, —$C_2$-$C_{25}$alkynyl, —$C_6$-$C_{10}$aryl, an hydroxyl, an amine, a halide, —$ONO_2$, —$NO_2$, —S—, —S—$C_1$-$C_5$alkyl, —S—$C_2$-$C_5$alkenyl, —S—$C_2$-$C_5$alkynyl, —C(═O)—, —C(═O)—$C_1$-$C_{25}$alkyl, —C(═O)—O—$C_1$-$C_5$alkyl, —C(═O)—O—$C_2$-$C_5$alkenyl, —C(═O)—O—$C_2$-$C_5$alkynyl, —C(═O)—NR'R"R'", —C(═O)—NR'—C(═O)—$C_1$-$C_{25}$alkyl, —C(═O)—NR'—C(═O)—$C_2$-$C_{25}$alkenyl, —C(═O)—NR—C(═O)—$C_2$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'";

the 5-, 6-, 7- or 8-membered carbocyclic ring may be optionally substituted by at least one functionality selected from structures (A) through (H):

(A)

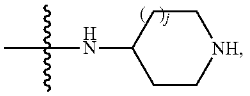

(B)

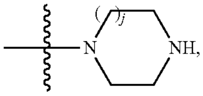

(C)

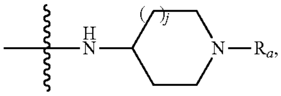

(D)

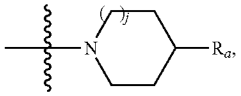

(E)

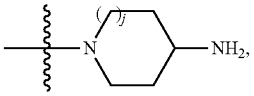

(F)

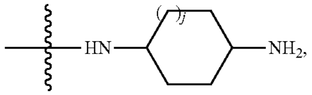

(G)

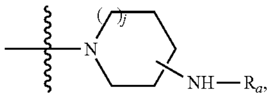

and (H)

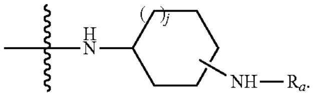

wherein in each functionality (A) through (H), the wavy line indicates point or bond of connectivity, j is 0 or 1 and Ra is selected from —H, —$C_1$-$C_{25}$alkyl, —$C_2$-$C_{25}$alkenyl, —$C_2$-$C_{25}$alkynyl, —C(═O)—$C_6$-$C_{10}$aryl and —C(═O)—$C_3$-$C_{10}$heteroaryl, wherein in functionalities (G) and (H) the pendant —NH—Ra group may appear between 1 and 11 times at any position along the carbocycle (in some embodiments, it may be positioned at a ring atom once removed, twice removed or three times removed from the existing group or endocyclic N atom; in some embodiments, the position of the functionality is 1, 2 or 1, 3 or 1, 4, wherein 1 designates the position of the existing group or the endocyclic N atom);

one of $R_5$, $R_6$ and $R_7$ may be absent;

$R_8$ is selected from H, —$C_1$-$C_{25}$alkyl, —$C_2$-$C_{25}$alkenyl, —$C_2$-$C_{25}$alkynyl, —$C_6$-$C_{10}$aryl and $C_3$-$C_{10}$heteroaryl, each of which being optionally substituted by at least one functionality selected from an hydroxyl, an amine, a halide, —$ONO_2$, —$NO_2$, —S—, —S—$C_1$-$C_5$alkyl, —S—$C_2$-$C_5$alkenyl, —S—$C_2$-$C_5$alkynyl, —C(═O)—, (═O)—$C_1$-$C_{25}$alkyl, —C(═O)—O—$C_1$-$C_5$alkyl, —C(═O)—O—$C_2$-$C_5$alkenyl, (═O)—O—$C_2$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, (═O)—NR—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'";

$R_{10}$ is selected from H, —$C_1$-$C_{25}$alkyl, —$C_2$-$C_{25}$alkenyl, —$C_2$-$C_{25}$alkynyl, —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2$C$(CH_3)_2$—O-aryl-Cl, idebenonyl-derivative, -pyridine-3-C(═O)—OH and —NR'R"R'";

each of R', R" and R'" is independently selected from —H, $C_1$-$C_5$alkyl, $C_2$-$C_5$alkenyl, $C_2$-$C_5$alkynyl, —C(═O)—$C_2$-$C_{25}$alkyl, —C(═O)—$C_2$-$C_{25}$alkenyl and $C_5$-$C_{25}$alkynyl; or wherein one of R', R" and R'" is absent; and wherein each bond between N-L, L-$L_1$, $L_1$-$L_2$ and $L_2$-C (designated ---) is a single or double bond.

In some embodiments, $R_8$ is —$C_1$-$C_{25}$alkyl.

In some embodiments, $R_8$ is —$C_2$-$C_{25}$alkenyl.

In some embodiments, $R_8$ is —$C_2$-$C_{25}$alkynyl.

In some embodiments, $R_8$ is —$C_6$-$C_{10}$aryl.

In some embodiments, $R_8$ is $C_3$-$C_{10}$heteroaryl.

In some embodiments, $R_8$ is —$C_1$-$C_{25}$alkyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2C(CH_3)_2$—O-aryl-Cl, idebenonyl-derivative, -pyridine-3-C(═O)—OH and —NR'R"R'".

In some embodiments, $R_8$ is —$C_2$-$C_{25}$alkenyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2C(CH_3)_2$—O-aryl-Cl, idebenonyl-derivative, -pyridine-3-C(═O)—OH and —NR'R"R'".

In some embodiments, $R_8$ is —$C_2$-$C_{25}$alkynyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'".

In some embodiments, $R_8$ is —$C_6$-$C_{10}$aryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'".

In some embodiments, $R_8$ is $C_3$-$C_{10}$heteroaryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'".

In some embodiments, in all compounds of the invention, excluded are compounds wherein $R_8$ is $C_7$-$C_{12}$alkyl. In such cases, where $R_8$ is said to be an alkyl having between 1 and 25 carbon atoms (inclusive), namely an alkyl of the form $C_1$-$C_{25}$alkyl or $C_1$-$C_{25}$alkylene, in consideration of the aforementioned exclusion, the alkyl or alkylene may be stated to be $C_1$-$C_6$alkyl/alkylene and $C_{13}$-$C_{25}$alkyl/alkylene.

In some embodiments, the 5-, 6-, 7- or 8-membered carbocyclic ring substituted by at least one functionality selected from structures (A) through (H):

(A)

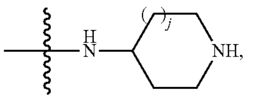

(B)

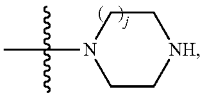

(C)

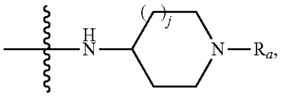

(D)

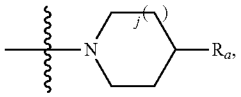

(E)

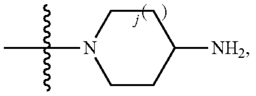

(F)

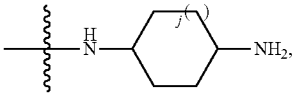

(G)

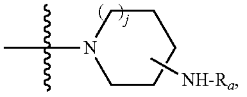

(H)

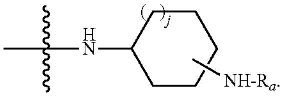

In some embodiments, in each functionality (A) through (H), j is 0.

In some embodiments, in each functionality (A) through (H), j is 1.

In some embodiments, the pendant —NH—Ra group appears once. In some embodiments, —NH—Ra is positioned at a ring atom once removed from the existing group or endocyclic N atom. In some embodiments, the —NH—Ra is positioned at a ring atom twice removed from the existing group or endocyclic N atom. In some embodiments, the —NH—Ra is positioned at a ring atom three times removed from the existing group or endocyclic N atom.

The invention further provides a compound of formula (II), as defined herein.

As used herein, a "carbon containing group having between 1 and 3 carbon atoms" is any carbon chain or carbon-containing group or a carbon-containing functionality that comprises one to three carbon atoms, inclusive, which may be bonded to each other or may be separated or interrupted by one or more atoms that are not carbon. In some embodiments, the carbon containing group is a group comprising a chain of one to three carbon atoms, each of which being connected to another atom. Non-limiting examples of such carbon groups include —CH, —$CH_2$—, —$CH_3$, —CH—CH—, —$CH_2$—CH—, —CH═CH—, —CH—$CH_2$—, —$CH_2$—$CH_2$—$CH_2$—, —$CH_2$—CH—CH—, —$CH_2$—CH═CH— and others. Non-limiting examples of such carbon groups that include one or more atoms that are not carbon, e.g., a heteroatom such as nitrogen, include CH—NH—, C═N—, —$CH_2$—NH—, —N—$CH_3$, —CH—NH—CH—, —$CH_2$—CH—NH—, —CH═N—CH—, —CH—NH—$CH_2$—, —$CH_2$—NH—$CH_2$—$CH_2$—, —$CH_2$—CH—NH—CH—, —$CH_2$—CH═CH—NH—, —$CH_2$—N═CH—NH—, —$CH_2$—NH—CH═CH—NH—, —$CH_2$—N═CH—, and others. Such groups may be optionally substituted.

The carbon-containing group containing between 1 and 3 carbon atoms may be alternatively designated as —$C_1$-$C_3$alkyl, —$C_2$-$C_3$alkenyl or —$C_2$-$C_3$alkynyl, or any substituted for thereof.

A "nitrogen atom or a nitrogen-containing group" is similarly any group of atoms or a functionality that comprises one or more nitrogen atoms. The nitrogen(s) atom may be substituted with hydrogen atoms or with a carbon group or any other functionality. In some embodiments, the nitrogen containing group is a group such as NH—, —$NH_2$—, —NHR', $NH_2$R', NHR'R", NR'R"R"', wherein each of R', R" and R"' is as further defined herein. The nitrogen containing group may additionally be selected from nitrogen-containing cycles. Non-limiting examples of such nitrogen-containing cycles include aziridinyl, azetidinyl, pyrrolidinyl, Imidazolidinyl, imidazolyl, Pyrazolidinyl, Pyrazolyl, triazolyl, piperidinyl, pyridinyl, piperazinyl, diazinyl, triazinyl, trihydrotriazinyl, indolyl, isoindolyl, quinolinyl, isoquinolinyl and others. The nitrogen atom or nitrogen-containing group may be presented in a form of a charged nitrogen atom (an ammonium).

As disclosed herein, e.g., with reference to variables $R_3$ and $R_4$, any two groups, as recited, together with atoms to which they are bonded (carbon atom and X, respectively, when in reference to variables $R_3$ and $R_4$) may form a 5- or 6-membered carbocyclic ring optionally containing a heteroatom, e.g., between 1 and 3 heteroatoms, inclusive, wherein the heteroatoms may be selected from N, O and S. Other non-carbon atoms may also be present. The 5- or 6-membered ring comprises one or more carbon atoms in a cyclic form (forming a carbocyclic structure). The carbon chain forming the carbocycle may be interrupted by one or more heteroatoms, together forming a heterocyclic ring structure.

In some embodiments, the heterocyclic ring may comprise 1, 2 or 3 nitrogen atoms. In some embodiments, the heterocyclic ring may comprise 1, 2 or 3 oxygen atoms. In some embodiments, the heterocyclic ring may comprise 1, 2 or 3 sulfur atoms.

In some embodiments, the heterocyclic ring may comprise 1, 2 or 3 nitrogen and/or oxygen and/or sulfur atoms.

In some embodiments, the heterocyclic ring may comprise 1 or 2 nitrogen atoms.

Alternatively, variables $R_3$ and $R_4$ together with atoms to which they are bonded (carbon atom and X, respectively, when in reference to variables $R_3$ and $R_4$) may form a fused ring system as defined.

$R_8$ is selected from —H, —$C_1$-$C_{25}$alkyl, —$C_2$-$C_{25}$alkenyl, —$C_2$-$C_{25}$alkynyl, —$C_6$-$C_{10}$aryl and —$C_3$-$C_{10}$heteroaryl. As used herein with reference to $R_8$ or to any other variable, the alkyl, alkenyl and alkynyl are each as known in the art.

Where $R_8$ or any other group is a $C_1$-$C_{25}$alkyl, it may be linear, branched or cyclic and may optionally be substituted by one or more substituents as defined. In some embodiments, $R_8$ is a linear alkyl comprising a number of carbon atoms selected from between 1 and 25, 1 and 20, 1 and 10, 5 and 25, 5 and 20, 10 and 25, 10 and 20, 15 and 25, 15 and 20 or between 20 and 25 carbon atoms. In some embodiments, the linear alkyl comprises 1, 2, 3, 4, 5, 6, 7, 8, 9, 10, 11, 12, 13, 14, 15, 16, 17, 18, 19 or 20 carbon atoms. In some embodiments, the linear alkyl comprises 6, 10, 16 or 18 carbon atoms.

Where the alkyl group is substituted on both ends, it may be regarded as an alkylene group.

In some embodiments, the alkyl group is a non-linear, branched or cyclic —$C_5$-$C_{25}$alkyl.

Where $R_8$ or any other group is a $C_5$-$C_{25}$alkenyl, it may be linear, branched or cyclic and comprising one or more double bonds in cis or trans configuration. The double bond may be a mid-chain double bond or a terminal double bond. Where $R_8$ is a cyclic alkenyl, the double bond may be endocyclic or exocyclic. In some embodiments, $R_8$ is a linear alkenyl comprising a number of carbon atoms selected from between 5 and 25, 5 and 20, 5 and 10, 10 and 25, 10 and 20, 15 and 25, 15 and 20 or between 20 and 25 carbon atoms. In some embodiments, the linear alkenyl comprises 5, 6, 7, 8, 9, 10, 11, 12, 13, 14, 15, 16, 17, 18, 19 or 20 carbon atoms. In some embodiments, the linear alkenyl comprises between 1 and 10 double bonds, each double bond may independently be in a cis or trans configuration. Where the alkenyl group is substituted on both ends, it may be regarded as an alkenylene group. Where $R_8$ or any other group is a $C_5$-$C_{25}$alkynyl, it may be linear, branched or cyclic and comprising one or more triple bonds. The triple bond may be a mid-chain bond or a terminal bond. Where $R_8$ is a cyclic alkynyl, the triple bond may be endocyclic or exocyclic. In some embodiments, $R_8$ is a linear alkynyl comprising a number of carbon atoms selected from between 5 and 25, 5 and 20, 5 and 10, 10 and 25, 10 and 20, 15 and 25, 15 and 20 or between 20 and 25 carbon atoms. In some embodiments, the linear alkynyl comprises 5, 6, 7, 8, 9, 10, 11, 12, 13, 14, 15, 16, 17, 18, 19 or 20 carbon atoms. In some embodiments, the linear alkynyl comprises between 1 and 5 triple bonds. Where the alkynyl group is substituted on both ends, it may be regarded as an alkynylene group.

In some embodiments, the alkyl, alkenyl or alkynyl may be selected from $CH_3(CH_2)_3-$, $CH_3(CH_2)_4-$, $CH_3(CH_2)_5-$, $CH_3(CH_2)_6-$, $CH_3(CH_2)_7-$, $CH_3(CH_2)_8-$, $CH_3(CH_2)_9-$, $CH_3(CH_2)_{10}-$, $CH_3(CH_2)_{11}-$, $CH_3(CH_2)_{12}-$, $CH_3(CH_2)_{13}-$, $CH_3(CH_2)_{14}-$, $CH_3(CH_2)_{15}-$, $CH_3(CH_2)_{16}-$, $CH_3(CH_2)_{17}-$, $CH_3(CH_2)_{18}-$, $CH_3(CH_2)_{19}-$, $CH_3(CH_2)_{20}-$, $CH_3(CH_2)_{21}-$, $CH_3(CH_2)_{22}-$, $CH_3(CH_2)_{23}-$, $(CH_3)_2CHCH_2-$, $CH_3(CH_2)_3CH=CH(CH_2)_7-$, $CH_3(CH_2)_5CH=CH(CH_2)_7-$, $CH_3(CH_2)_8CH=CH(CH_2)_4-$, $CH_3(CH_2)_7CH=CH(CH_2)_7-$, $CH_3(CH_2)_7CH=CH(CH_2)_7-$, $CH_3(CH_2)_5CH=CH(CH_2)_9-$, $CH_3(CH_2)_4CH=CHCH_2CH=CH(CH_2)_7-$, $CH_3(CH_2)_4CH=CHCH_2CH=CH(CH_2)_7-$, $CH_3CH_2CH=CHCH_2CH=CHCH_2CH=CH(CH_2)_7-$, $CH_3(CH=CH)_2-$, $CH_3(CH_2)_4CH=CHCH_2CH=CHCH_2-CH=CHCH_2CH=CH(CH_2)_3-$, $CH_3CH_2CH=CHCH_2CH=CHCH_2CH=CHCH_2CH=CHCH_2-CH=CH(CH_2)_3-$, $CH_3(CH_2)_7CH=CH(CH_2)_{11}-$, $CH_3CH_2CH=CHCH_2CH=CHCH_2CH=CH-CH_2CH=CHCH_2CH=CHCH_2CH=CH(CH_2)_2-$, $CH_3CH_2CH=CHCH_2CH=CHCH_2CH=CH-CH_2CH=CH(CH_2)_4-$, $CH_3(CH_2)_4CH=CHCH_2CH=CHCH_2CH=CH(CH_2)_4-$, $CH_3(CH_2)_4CH=CHCH_2CH=CHCH_2CH=CH(CH_2)_6-$, $CH_3(CH_2)_4CH=CHCH_2CH=CHCH_2CH=CHCH_2-CH=CH(CH_2)_5-$, $CH_3(CH_2)_5CH=CH(CH_2)_{11}-$, $CH_3(CH_2)_7CH=CH(CH_2)_9-$, $CH_3(CH_2)_7CH=CH(CH_2)_{13}-$, $CH_3(CH_2)_7CH=CHCH_2CH=CHCH_2CH=CH(CH_2)_3-$, $C_6H_5CH=CH-$, $CH_3(CH_2)_3\equiv(CH_2)_7-$, $CH_3(CH_2)_5C\equiv C(CH_2)_7-$, $CH_3(CH_2)_8C\equiv C(CH_2)_4-$, $CH_3(CH_2)_7C\equiv C-(CH_2)_7-$, $CH_3(CH_2)_7C\equiv C(CH_2)_7-$, $CH_3(CH_2)_5C\equiv C(CH_2)_9-$, $CH_3(CH_2)_4C\equiv CCH_2CH=CH(CH_2)_7-$, $CH_3(CH_2)_4CH-CHCH_2C\equiv C(CH_2)_7-$, $CH_3(CH_2)_4C\equiv CCH_2C\equiv C(CH_2)_7-$, $CH_3CH_2C\equiv CCH_2CH=CHCH_2CH=CH(CH_2)_7-$, $CH_3(CC)_2-$, $CH_3(CH_2)_4C\equiv CCH_2CH=CHCH_2-CH=CHCH_2CH=CH(CH_2)_3-$, $CH_3(CH_2)_4CH=CHCH_2CH=CHCH_2C\equiv CCH_2CH=CH(CH_2)_3-$, $CH_3CH_2CH=CHCH_2CH=CHCH_2C\equiv CCH_2CH=CHCH_2-CH=CH(CH_2)_3-$, $CH_3(CH_2)_7C\equiv C(CH_2)_{11}-CH_3CH_2C\equiv CCH_2CH=CHCH_2C\equiv CCH_2CH=CHCH_2C\equiv CCH_2-CH=CH(CH_2)_2-$, $CH_3CH_2CH=CHCH_2CH=CHCH_2C\equiv C-CH_2C\equiv C(CH_2)_4-$, $CH_3(CH_2)_4C\equiv CCH_2CH=CHCH_2C\equiv C(CH_2)_4-$, $CH_3(CH_2)_4CH=CHCH_2CH=CHCH_2C\equiv C(CH_2)_6-$, $CH_3(CH_2)_4C\equiv CCH_2CH=CHCH_2C\equiv CCH_2-CH=CH(CH_2)_5-$, $CH_3(CH_2)_5C\equiv C(CH_2)_{11}-$, $CH_3(CH_2)_7C\equiv C(CH_2)_9-$, $CH_3(CH_2)_7C\equiv C(CH_2)_{13}$ $CH_3(CH_2)_7C\equiv CCH_2CH-CH-CH_2C\equiv C(CH_2)_3-$ $C_6H_5C\equiv C-$ and alkenylene derived from DHA (all-cis-docosa-4,7,10,13,16,19-hexa-enoic acid).

Where $R_8$ or any other group is a $C_6$-$C_{10}$aryl, the aryl group, as known in the art, may be any aromatic system comprising between 6 and 10 atoms, typically carbon atoms. The aryl group may be a single aromatic ring, such as a phenyl or a benzyl ring; a group containing two or more rings structures, one or more of which being aromatic, such as a diphenyl group; or a fused ring system comprising at least one aromatic ring, such as fused phenyl rings and naphthyl groups.

Where $R_8$ or any other group is a $C_3$-$C_{10}$heteroaryl, the group comprises one or more heteroatom in the ring structure. Such groups may contain nitrogen oxygen or sulfur atoms as ring atoms. Non-limiting examples include pyrrolyl, pyridyl, pyrimidyl, pyrazinyl, indolyl, quinolyl, isoquinolyl, furyl, thienyl, oxazolyl, benzoxazolyl, thiazolyl, benzothiazolyl, benzofuranyl, benzdioxolyl, benzothiophenyl and others. Substitution of the heteroaryl group may be at any position, typically at any carbon atom of the heteroaryl group. For example, the pyridyl group may be substituted ortho, meta or para to the N atom.

In some embodiments, in a compound of formula (II), $R_5$ or $R_6$ or $R_7$ is —C(═O)—O—$R_8$ or —C(═O)—NR'$R_8$, and $R_8$ is —$C_1$-$C_{25}$alkyl selected, for example, from $(CH_2)_8CH{=}CH(CH_2)_7CH_3$, $-(CH_2)_2-$, $-(CH_2)_{15}CH_3$, $-(CH_2)_{15}CH_3$ and $(CH_2)_2CH{=}CH(CH_2CH{=}CH)_5CH_2CH_3$.

In some embodiments, in a compound of formula (II), $R_6$ or $R_7$ is —C(═O)—O—$R_8$ or —C(═O)—NR'$R_8$, and $R_8$ is selected from 2,2,6,6-tetramethylpiperidin-1-ol-4-yl, —NHC(═O)$CH_2C(CH_3)_2$—O-aryl-Cl, idebenonyl-derivative, -pyridine-3-C(═O)—OH and —NR'R"R'".

The group "2,2,6,6-tetramethylpiperidin-1-ol-4-yl" is the radical having the structure:

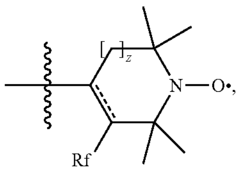

wherein z is 1, Rf is H and wherein the dashed bond is a single bond. Yet, also encompassed are groups wherein Z is zero, the dashed bond is a single bond or a double bond and wherein Rf is H or is selected from halide, —CN, —OH, —$C_2$-$C_{25}$alkenyl, —$C_2$-$C_{25}$alkynyl, —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, $C_5$alkyl, —C(═O)—O—$C_1$-$C_5$alkenyl, (═O)—O—$C_1$-$C_5$alkynyl, —C(═O)—NR'R"R'", —C(═O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_5$alkenyl, —S—$C_1$-$C_5$alkynyl, —$ONO_2$, —$NO_2$, and —NR'R"R'", as defined herein.

In some embodiments, in a group wherein Z is zero, the groups may be selected from:

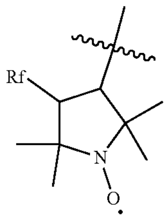

and

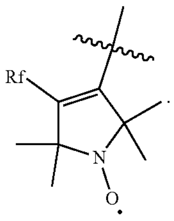

The group "—NHC(═O)$CH_2C(CH_3)_2$—O-aryl-Cl" designates a substituted aryl group, wherein the chloride atom and the ether group are substituted on the aryl structure ortho, meta or para to each other. In some embodiments, the group has the structure:

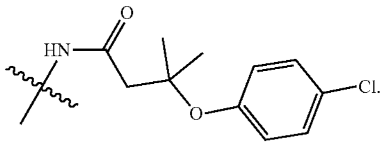 [SMILES: *NC(=O)CC(C)(C)Oc1ccc(Cl)cc1]

The "idebenonyl-derivative" is a group of the structure:

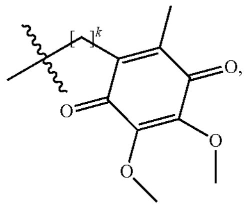

wherein k is an integer between 0 and 25.

In some embodiments, k is between 1 and 25, 1 and 20, 1 and 15, 1 and 10, 1 and 5, 5 and 25, 5 and 20, 5 and 10, 10 and 25 or between 10 and 20. In some embodiments, k is 5, 6, 7, 8, 9, 10, 11, 12, 13, 14 or 15. In some embodiments, k is 10.

The group "-pyridine-3-C(═O)—OH" is a niacin acid derivative, wherein the substitution on the pyridine ring may be at any position relative to the carboxylic acid group or to the ring nitrogen atom.

The group "—NR'R"R'"" designates an amine which may be a primary amine, a secondary amine, a tertiary amine or a quaternary amine Each of the R groups may be selected as disclosed herein. In some embodiments, each of R', R" and R'" is independently —H, —$C_1$-$C_5$alkyl, —$C_2$-$C_5$alkenyl, —$C_2$-$C_5$alkynyl, —C(═O)—$C_2$-$C_{25}$alkyl, —C(═O)—$C_2$-$C_{25}$alkenyl or $C_5$-$C_{25}$alkynyl. In cases where the group designates a charged nitrogen atom (an ammonium), the three R groups are presented and may be selected as indicated. In cases where the group designates an uncharged nitrogen atom, one of R', R" and R'" is absent and the remaining two groups may be each selected as indicated herein.

As recited herein, in a compound of formula (II), $R_5$ or $R_6$ or $R_7$ may be —C(═O)—O—$R_8$ or —C(═O)—NR'$R_8$, wherein $R_8$ is selected as above. Each of the groups selected for $R_8$ may be substituted or unsubstituted. In some embodiments, the groups selected for $R_8$, namely —$C_1$-$C_{25}$alkyl, —$C_2$-$C_{25}$alkenyl, —$C_2$-$C_{25}$alkynyl and —$C_6$-$C_{10}$aryl, may be substituted by at least one functionality selected from an hydroxyl (—OH), an amine (primary, secondary, tertiary or quaternary amine), a halide (selected F, Br, Cl and I), —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-aryl-Cl, idebenonyl-derivative, -pyridine-3-C(═O)—OH and —NR'R"R'".

In some embodiments, $R_5$ or $R_6$ or $R_7$ is —C(═O)—O—$R_8$ and $R_8$ is selected as above. In some embodiments, $R_8$ is —$C_1$-$C_{25}$alkyl. In some embodiments, the —$C_1$-$C_{25}$alkyl is selected from optionally substituted —$(CH_2)_8CH$═CH$(CH_2)_7CH_3$, —$(CH_2)_2$—, —$(CH_2)_{15}CH_3$, —$(CH_2)_{15}CH_3$ and —$(CH_2)_2CH$═CH($CH_2CH$═CH$)_5CH_2CH_3$. In some embodiments, the aforementioned groups are substituted by —NR'R"R'", wherein one of said R', R" and R'" is absent and the other of R', R" and R'" is selected from —H, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'" and —C(═O)—$OR_{10}$, as defined herein. In some embodiments, the group —NR'R"R'" is thus —NHR'" (R' absent and R"═H), wherein R'" is H, —C(═O)—, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'" or —C(═O)—$OR_{10}$. In some embodiments, R'" is —C(═O)—, —C(═O)—$C_1$-$C_{25}$alkyl, —C(═O)—O—$C_1$-$C_5$alkyl, —C(═O)—O—$C_1$-$C_5$alkenyl, or —C(═O)—O—$C_1$-$C_5$alkynyl. In some embodiments, R'" is —C(═O)— or —C(═O)—$C_1$-$C_{25}$alkyl.

In some embodiments, $R_5$ or $R_6$ or $R_7$ is —C(═O)—O—$R_8$ and $R_8$ is selected from $(CH_2)_8CH$═CH$(CH_2)_7CH_3$, —$(CH_2)_2$—, —$(CH_2)_{15}CH_3$, —$(CH_2)_{15}CH_3$, —$(CH_2)_2$—NHC(═O)$(CH_2)_7CH$═CH$(CH_2)_7CH_3$ and $(CH_2)_2CH$═CH($CH_2CH$═CH$)_5CH_2CH_3$.

In some embodiments, $R_5$ or $R_6$ or $R_7$ is —C(═O)—O—$(CH_2)_8CH$═CH$(CH_2)_7CH_3$, —C(═O)—O—$(CH_2)_2$—, —C(═O)—O—$(CH_2)_{15}CH_3$, —C(═O)—O—$(CH_2)_{15}CH_3$, —C(═O)—O—$(CH_2)_2$—NHC(═O)$(CH_2)_7CH$═CH$(CH_2)_7CH_3$ and —C(═O)—O—$(CH_2)_2CH$═CH($CH_2CH$═CH$)_5$—$CH_2CH_3$.

In some embodiments, $R_5$ or $R_6$ or $R_7$ is —C(═O)—NR'$R_8$ and $R_8$ is selected as above. In some embodiments, $R_8$ is —$C_1$-$C_{25}$alkyl. In some embodiments, the —$C_1$-$C_{25}$alkyl is selected from optionally substituted —$(CH_2)_8CH$═CH$(CH_2)_7CH_3$, —$(CH_2)_2$—, —$(CH_2)_{15}CH_3$, —$(CH_2)_{15}CH_3$ and $(CH_2)_2CH$═CH($CH_2CH$═CH$)_5CH_2CH_3$.

In some embodiments, $R_5$ or $R_6$ or $R_7$ is —C(═O)—NR'$R_8$ and $R_8$ is selected from $(CH_2)_8CH$═CH$(CH_2)_7CH_3$, —$(CH_2)_2$—, —$(CH_2)_{15}CH_3$, —$(CH_2)_{15}CH_3$, —$(CH_2)_2$—NHC(═O)$(CH_2)_7CH$═CH$(CH_2)_7CH_3$ and $(CH_2)_2CH$═CH($CH_2CH$═CH$)_5CH_2CH_3$. In some embodiments, R' is H.

In some embodiments, $R_5$ or $R_6$ or $R_7$ is —C(═O)—NH—$(CH_2)_8CH$═CH$(CH_2)_7CH_3$, —C(═O)—NH—$(CH_2)_2$—, —C(═O)—NH—$(CH_2)_{15}CH_3$, —C(═O)—NH—$(CH_2)_{15}CH_3$ and —C(═O)—NH—$(CH_2)_2$—NHC(═O)$(CH_2)_7CH$═CH$(CH_2)_7CH_3$ and —C(═O)—NH—$(CH_2)_2CH$═CH—($CH_2CH$═CH$)_5CH_2CH_3$.

In some embodiments, in a compound of formula (II), L is a nitrogen atom (or a nitrogen containing group of atoms) and each of $L_1$ and $L_2$ is a carbon atom (or a carbon containing group of atoms).

In some embodiments, L is a nitrogen atom (or a nitrogen containing group of atoms), each of $L_1$ and $L_2$ is a carbon atom (or a carbon containing group of atoms), the bond between N and L is a single bond, the bond between L and $L_1$ is a double bond, and the bond between $L_1$ and $L_2$ is a single bond.

In some embodiments, R5 is absent.

In some embodiments, the compound is of formula (III):

(III)

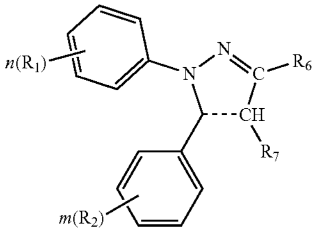

wherein each of $R_1$, $R_2$, n, m, $R_6$ and $R_7$ are as defined herein, and wherein --- designates a single or a double bond (in case it is a double bond, the carbon atom bearing variant R7 does not carry a bond to a hydrogen atom).

As indicated herein, each of $R_6$ and $R_7$, independently of the other, may be selected from —H, —$C_1$-$C_3$alkyl, —C(═O)—OH, —C(═O)—O—$R_8$, —C(═O)—NR'$R_8$, halide, —CN, —OH, and —NR'R"; or $R_6$ and $R_7$ together with the atoms to which they bond may form a 5-, 6-, 7- or 8-membered carbocyclic ring optionally containing between 1 and 3 heteroatoms selected from N, O and S. Substitution may be as indicated above.

In some embodiments, $R_7$ is H and $R_6$ is selected from —$C_1$-$C_3$alkyl, —C(═O)—O—$R_8$, —C(═O)—NR'—$R_8$, a halide, —CN, —OH, and —NR'R"; wherein $R_8$ is as defined herein.

In some embodiments, $R_6$ is —C(═O)—NR'$R_8$; and $R_8$ is as defined herein.

In some embodiments, $R_6$ is —C(═O)—NH$R_8$; and $R_8$ is as defined herein.

In some embodiments, the bond --- is a double bond.

In some embodiments, the bond --- is a single bond.

In some embodiments, the compound is of general formula (IV):

(IV)

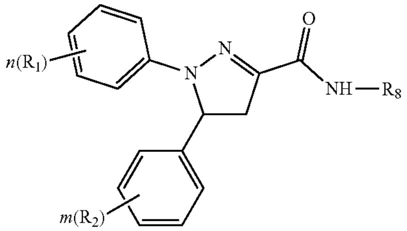

wherein each of $R_1$, $R_2$, n, m and $R_8$ is as defined herein.

In some embodiments, $R_8$ is a $C_1$-$C_{25}$alkyl, optionally substituted, as disclosed and selected herein.

In some embodiments, n is 2 and m is 1.

In some embodiments, $R_1$ and $R_2$ are each a halide.

In some embodiments, each of $R_1$ and $R_2$ is a chloride atom.

In some embodiments, the compound is of the formula (V):

(V)

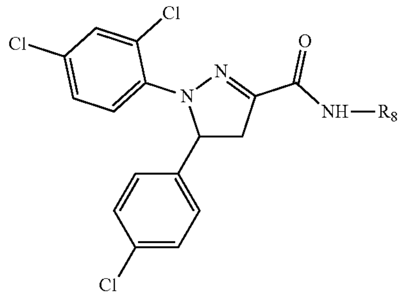

wherein $R_8$ is as defined herein.

In some embodiments, for a compound of formula (IV) and/or (V), $R_8$ may be:

—$C_1$-$C_{25}$alkyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(=O)—, —C(=O)—$C_1$-$C_{25}$alkyl, —C(=O)—O—$C_1$-$C_5$alkyl, —C(=O)—O—$C_1$-$C_5$alkenyl, —C(=O)—O—$C_1$-$C_5$alkynyl, —C(=O)—NR'R"R'", —C(=O)—NR'—C(=O)—$C_1$-$C_{25}$alkyl, —C(=O)—NR'—C(=O)—$C_1$-$C_{25}$alkenyl, —C(=O)—NR'—C(=O)—$C_1$-$C_{25}$alkynyl, —C(=O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(=O)—$C_1$-$C_{25}$alkyl, —NH—NH—C(=O)—$C_2$-$C_{25}$alkenyl, —NH—NH—C(=O)—$C_2$-$C_{25}$alkynyl, —NH—NH—C(=O)—$C_6$-$C_{10}$aryl, —NH—NH—C(=O)—$C_3$-$C_{10}$heteroaryl, —NH—$C_1$-$C_{25}$alkyl-C(=O)—OH, —NH—$C_2$-$C_{25}$alkenyl-C(=O)—OH, —NH—$C_2$-$C_{25}$alkynyl-C(=O)—OH, —NH—$C_1$-$C_{25}$alkyl-C(=O)—NR'R"R'", —NH—$C_2$-$C_{25}$alkenyl-C(=O)—NR'R"R'", —NH—$C_2$-$C_{25}$alkynyl-C(=O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(=O)—$C_1$-$C_{25}$alkyl, —NH—$C_2$-$C_{25}$alkenyl-NH—C(=O)—$C_1$-$C_{25}$alkyl, —NH—$C_2$-$C_{25}$alkynyl-NH—C(=O)—$C_1$-$C_{25}$alkyl, —NH—$C_1$-$C_{25}$alkyl-NH—C(=O)—$C_6$-$C_{10}$aryl, —NH—$C_2$-$C_{25}$alkenyl-NH—C(=O)—$C_6$-$C_{10}$aryl, —NH—$C_2$-$C_{25}$alkynyl-NH—C(=O)—$C_6$-$C_{10}$aryl, —NH—$C_1$-$C_{25}$alkyl-NH—C(=O)—$C_3$-$C_{10}$heteroaryl, —NH—$C_2$-$C_{25}$alkenyl-NH—C(=O)—$C_3$-$C_{10}$heteroaryl, —NH—$C_2$-$C_{25}$alkynyl-NH—C(=O)—$C_3$-$C_{10}$heteroaryl, —NH—$C_1$-$C_{25}$alkylene-C(=O)—NR'R"R'", —NH—$C_2$-$C_{25}$alkenylene-C(=O)—NR'R"R'", —NH—$C_2$-$C_{25}$alkynylene-C(=O)—NR'R"R'", —NH—$C_1$-$C_{25}$alkylene-C(=O)—O—$C_1$-$C_{25}$alkyl, —NH—$C_2$-$C_{25}$alkenylene-C(=O)—O—$C_1$-$C_{25}$alkyl, —NH—$C_2$-$C_{25}$alkynylene-C(=O)—O—$C_1$-$C_{25}$alkyl, —NHC(=O)$C_1$-$C_{25}$alkyl, —NHC(=O)$C_2$-$C_{25}$alkenyl, —NHC(=O)$C_2$-$C_{25}$alkynyl, —NHC(=O)$C_1$-$C_{25}$alkylene-NR'R"R'", —NHC(=O)$C_2$-$C_{25}$alkenylene-NR'R"R'", —NHC(=O)$C_2$-$C_{25}$alkynylene-NR'R"R'", —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C$(CH_3)_2$—O-aryl-Cl, —NHC(=O)$CH_2$C$(CH_3)_2$—O-aryl-Cl, idebenonyl-derivative, -pyridine-3-C(=O)—OH and —NR'R"R'"; or —$C_2$-$C_{25}$alkenyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(=O)—, —C(=O)—$C_1$-$C_{25}$alkyl, —C(=O)—O—$C_1$-$C_5$alkyl, —C(=O)—O—$C_1$-$C_5$alkenyl, —C(=O)—O—$C_1$-$C_5$alkynyl, —C(=O)—NR'R"R'", —C(=O)—NR'—C(=O)—$C_1$-$C_{25}$alkyl, —C(=O)—NR—C(=O)—$C_1$-$C_{25}$alkenyl, —C(=O)—NR'—C(=O)—$C_1$-$C_{25}$alkynyl, —C(=O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(=O)—$C_1$-$C_{25}$alkyl, —NH—NH—C(=O)—$C_2$-$C_{25}$alkenyl, —NH—NH—C(=O)—$C_2$-$C_{25}$alkynyl, —NH—NH—C(=O)—$C_6$-$C_{10}$aryl, —NH—NH—C(=O)—$C_3$-$C_{10}$heteroaryl, —NH—$C_1$-$C_{25}$alkyl-C(=O)—OH, —NH—$C_2$-$C_{25}$alkenyl-C(=O)—OH, —NH—$C_2$-$C_{25}$alkynyl-C(=O)—OH, —NH—$C_1$-$C_{25}$alkyl-C(=O)—NR'R"R'", —NH—$C_2$-$C_{25}$alkenyl-C(=O)—NR'R"R'", —NH—$C_2$-$C_{25}$alkynyl-C(=O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(=O)—$C_1$-$C_{25}$alkyl, —NH—$C_2$-$C_{25}$alkenyl-NH—C(=O)—$C_1$-$C_{25}$alkyl, —NH—$C_2$-$C_{25}$alkynyl-NH—C(=O)—$C_1$-$C_{25}$alkyl, —NH—$C_1$-$C_{25}$alkyl-NH—C(=O)—$C_6$-$C_{10}$aryl, —NH—$C_2$-$C_{25}$alkenyl-NH—C(=O)—$C_6$-$C_{10}$aryl, —NH—$C_2$-$C_{25}$alkynyl-NH—C(=O)—$C_6$-$C_{10}$aryl, —NH—$C_1$-$C_{25}$alkyl-NH—C(=O)—$C_3$-$C_{10}$heteroaryl, —NH—$C_2$-$C_{25}$alkenyl-NH—C(=O)—$C_3$-$C_{10}$heteroaryl, —NH—$C_2$-$C_{25}$alkynyl-NH—C(=O)—$C_3$-$C_{10}$heteroaryl, —NH—$C_1$-$C_{25}$alkylene-C(=O)—NR'R"R'", —NH—$C_2$-$C_{25}$alkenylene-C(=O)—NR'R"R'", —NH—$C_2$-$C_{25}$alkynylene-C(=O)—NR'R"R'", —NH—$C_1$-$C_{25}$alkylene-C(=O)—O—$C_1$-$C_{25}$alkyl, —NH—$C_2$-$C_{25}$alkenylene-C(=O)—O—$C_1$-$C_{25}$alkyl, —NH—$C_2$-$C_{25}$alkynylene-C(=O)—O—$C_1$-$C_{25}$alkyl, —NHC(=O)$C_1$-$C_{25}$alkyl, —NHC(=O)$C_2$-$C_{25}$alkenyl, —NHC(=O)$C_2$-$C_{25}$alkynyl, —NHC(=O)$C_1$-$C_{25}$alkylene-NR'R"R'", NHC(=O)$C_2$-$C_{25}$alkenylene-NR'R"R'", —NHC(=O)$C_2$-$C_{25}$alkynylene-NR'R"R'", —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C$(CH_3)_2$—O-aryl-Cl, —NHC(═O)$CH_2C(CH_3)_2$—O-aryl-Cl, idebenonyl-derivative, -pyridine-3-C(═O)—OH and —NR'R"R'"; or —$C_2$-$C_{25}$alkynyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)$C(CH_3)_2$—O-aryl-Cl, —NHC(═O)$CH_2C(CH_3)_2$—O-aryl-Cl, idebenonyl-derivative, -pyridine-3-C(═O)—OH and —NR'R"R'"; or —$C_6$-$C_{10}$aryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)$C(CH_3)_2$—O-aryl-Cl, —NHC(═O)$CH_2C(CH_3)_2$—O-aryl-Cl, idebenonyl-derivative, -pyridine-3-C(═O)—OH and —NR'R"R'"; or —$C_3$-$C_{10}$heteroaryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—

NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)$C(CH_3)_2$—O-aryl-Cl, —NHC(═O)$CH_2C(CH_3)_2$—O-aryl-Cl, idebenonyl-derivative, -pyridine-3-C(═O)—OH and —NR'R"R'".

In some embodiments, in a compound of formula (II), L is a nitrogen atom, each of $L_1$ and $L_2$ is a carbon atom, the bond between N and L is a single bond, the bond between L and $L_1$ is a double bond, the bond between $L_1$ and $L_2$ is a single bond and the bond between $L_2$ and C is a double bond.

In some embodiments, the compound is of the general formula (VI):

(VI)

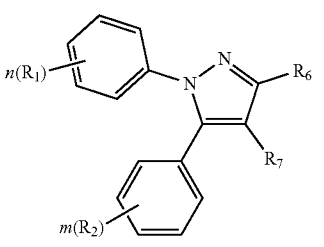

wherein each of $R_1$, $R_2$, n, m, $R_6$ and $R_7$ is as defined herein.

In some embodiments, $R_6$ is selected from —$C_1$-$C_3$alkyl, —C(═O)—O—$R_8$, —C(═O)—NR'—$R_8$, a halide, —CN, —OH, and —NR'R";

$R_7$ is a $C_1$-$C_3$alkyl;

$R_8$ is as defined herein.

In some embodiments, $R_6$ is —C(═O)—NR'—$R_8$; and $R_8$ is a $C_1$-$C_{25}$alkyl.

In some embodiments, the compound is of general formula (VII):

(VII)

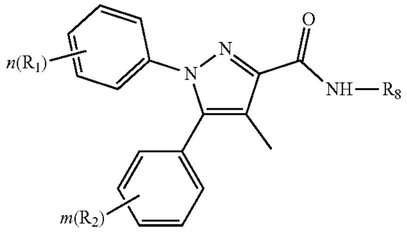

wherein each of $R_1$, $R_2$, n, m and $R_8$ is as defined herein.

In some embodiments, for a compound of formula (VII), $R_8$ may be:

—$C_1$-$C_{25}$alkyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)$C(CH_3)_2$—O-aryl-Cl, —NHC(═O)$CH_2C(CH_3)_2$—O-aryl-Cl, idebenonyl-derivative, -pyridine-3-C(═O)—OH and —NR'R"R'"; or —$C_2$-$C_{25}$alkenyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(=O)—, —C(=O)—$C_1$-$C_{25}$alkyl, —C(=O)—O—$C_1$-$C_5$alkyl, —C(=O)—O—$C_1$-$C_5$alkenyl, —C(=O)—O—$C_1$-$C_5$alkynyl, —C(=O)—NR'R"R'", —C(=O)—NR'—C(=O)—$C_1$-$C_{25}$alkyl, —C(=O)—NR'—C(=O)—$C_1$-$C_{25}$alkenyl, —C(=O)—NR'—C(=O)—$C_1$-$C_{25}$alkynyl, —C(=O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(=O)—$C_1$-$C_{25}$alkyl, —NH—NH—C(=O)—$C_2$-$C_{25}$alkenyl, —NH—NH—C(=O)—$C_2$-$C_{25}$alkynyl, —NH—NH—C(=O)—$C_6$-$C_{10}$aryl, —NH—NH—C(=O)—$C_3$-$C_{10}$heteroaryl, —NH—$C_1$-$C_{25}$alkyl-C(=O)—OH, —NH—$C_2$-$C_{25}$alkenyl-C(=O)—OH, —NH—$C_2$-$C_{25}$alkynyl-C(=O)—OH, —NH—$C_1$-$C_{25}$alkyl-C(=O)—NR'R"R'", —NH—$C_2$-$C_{25}$alkenyl-C(=O)—NR'R"R'", —NH—$C_2$-$C_{25}$alkynyl-C(=O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(=O)—$C_1$-$C_{25}$alkyl, —NH—$C_2$-$C_{25}$alkenyl-NH—C(=O)—$C_1$-$C_{25}$alkyl, —NH—$C_2$-$C_{25}$alkynyl-NH—C(=O)—$C_1$-$C_{25}$alkyl, —NH—$C_1$-$C_{25}$alkyl-NH—C(=O)—$C_6$-$C_{10}$aryl, —NH—$C_2$-$C_{25}$alkenyl-NH—C(=O)—$C_6$-$C_{10}$aryl, —NH—$C_2$-$C_{25}$alkynyl-NH—C(=O)—$C_6$-$C_{10}$aryl, —NH—$C_1$-$C_{25}$alkyl-NH—C(=O)—$C_3$-$C_{10}$heteroaryl, —NH—$C_2$-$C_{25}$alkenyl-NH—C(=O)—$C_3$-$C_{10}$heteroaryl, —NH—$C_2$-$C_{25}$alkynyl-NH—C(=O)—$C_3$-$C_{10}$heteroaryl, —NH—$C_1$-$C_{25}$alkylene-C(=O)—NR'R"R'", —NH—$C_2$-$C_{25}$alkenylene-C(=O)—NR'R"R'", —NH—$C_2$-$C_{25}$alkynylene-C(=O)—NR'R"R'", —NH—$C_1$-$C_{25}$alkylene-C(=O)—O—$C_1$-$C_{25}$alkyl, —NH—$C_2$-$C_{25}$alkenylene-C(=O)—O—$C_1$-$C_{25}$alkyl, —NH—$C_2$-$C_{25}$alkynylene-C(=O)—O—$C_1$-$C_{25}$alkyl, —NHC(=O)$C_1$-$C_{25}$alkyl, —NHC(=O)$C_2$-$C_{25}$alkenyl, —NHC(=O)$C_2$-$C_{25}$alkynyl, —NHC(=O)$C_1$-$C_{25}$alkylene-NR'R"R'", —NHC(=O)$C_2$-$C_{25}$alkenylene-NR'R"R'", —NHC(=O)$C_2$-$C_{25}$alkynylene-NR'R"R'", —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C$(CH_3)_2$—O-aryl-Cl, —NHC(=O)$CH_2$C$(CH_3)_2$—O-aryl-Cl, idebenonyl-derivative, -pyridine-3-C(=O)—OH and —NR'R"R'"; or —$C_2$-$C_{25}$alkynyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(=O)—, —C(=O)—$C_1$-$C_{25}$alkyl, —C(=O)—O—$C_1$-$C_5$alkyl, —C(=O)—O—$C_1$-$C_5$alkenyl, —C(=O)—O—$C_1$-$C_5$alkynyl, —C(=O)—NR'R"R'", —C(=O)—NR'—C(=O)—$C_1$-$C_{25}$alkyl, —C(=O)—NR—C(=O)—$C_1$-$C_{25}$alkenyl, —C(=O)—NR'—C(=O)—$C_1$-$C_{25}$alkynyl, —C(=O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(=O)—$C_1$-$C_{25}$alkyl, —NH—NH—C(=O)—$C_2$-$C_{25}$alkenyl, —NH—NH—C(=O)—$C_2$-$C_{25}$alkynyl, —NH—NH—C(=O)—$C_6$-$C_{10}$aryl, —NH—NH—C(=O)—$C_3$-$C_{10}$heteroaryl, —NH—$C_1$-$C_{25}$alkyl-C(=O)—OH, —NH—$C_2$-$C_{25}$alkenyl-C(=O)—OH, —NH—$C_2$-$C_{25}$alkynyl-C(=O)—OH, —NH—$C_1$-$C_{25}$alkyl-C(=O)—NR'R"R'", —NH—$C_2$-$C_{25}$alkenyl-C(=O)—NR'R"R'", —NH—$C_2$-$C_{25}$alkynyl-C(=O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(=O)—$C_1$-$C_{25}$alkyl, —NH—$C_2$-$C_{25}$alkenyl-NH—C(=O)—$C_1$-$C_{25}$alkyl, —NH—$C_2$-$C_{25}$alkynyl-NH—C(=O)—$C_1$-$C_{25}$alkyl, —NH—$C_1$-$C_{25}$alkyl-NH—C(=O)—$C_6$-$C_{10}$aryl, —NH—$C_2$-$C_{25}$alkenyl-NH—C(=O)—$C_6$-$C_{10}$aryl, —NH—$C_2$-$C_{25}$alkynyl-NH—C(=O)—$C_6$-$C_{10}$aryl, —NH—$C_1$-$C_{25}$alkyl-NH—C(=O)—$C_3$-$C_{10}$heteroaryl, —NH—$C_2$-$C_{25}$alkenyl-NH—C(=O)—$C_3$-$C_{10}$heteroaryl, —NH—$C_2$-$C_{25}$alkynyl-NH—C(=O)—$C_3$-$C_{10}$heteroaryl, —NH—$C_1$-$C_{25}$alkylene-C(=O)—NR'R"R'", —NH—$C_2$-$C_{25}$alkenylene-C(=O)—NR'R"R'", —NH—$C_2$-$C_{25}$alkynylene-C(=O)—NR'R"R'", —NH—$C_1$-$C_{25}$alkylene-C(=O)—O—$C_1$-$C_{25}$alkyl, —NH—$C_2$-$C_{25}$alkenylene-C(=O)—O—$C_1$-$C_{25}$alkyl, —NH—$C_2$-$C_{25}$alkynylene-C(=O)—O—$C_1$-$C_{25}$alkyl, —NHC(=O)$C_1$-$C_{25}$alkyl, —NHC(=O)$C_2$-$C_{25}$alkenyl, —NHC(=O)$C_2$-$C_{25}$alkynyl, —NHC(=O)$C_1$-$C_{25}$alkylene-NR'R"R'", —NHC(=O)$C_2$-$C_{25}$alkenylene-NR'R"R'", —NHC(=O)$C_2$-$C_{25}$alkynylene-NR'R"R'", —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C$(CH_3)_2$—O-aryl-Cl, —NHC(=O)$CH_2$C$(CH_3)_2$—O-aryl-Cl, idebenonyl-derivative, -pyridine-3-C(=O)—OH and —NR'R"R'"; or —$C_6$-$C_{10}$aryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(=O)—, —C(=O)—$C_1$-$C_{25}$alkyl, —C(=O)—O—$C_1$-$C_5$alkyl, —C(=O)—O—$C_1$-$C_5$alkenyl, —C(=O)—O—$C_1$-$C_5$alkynyl, —C(=O)—NR'R"R'", —C(=O)—NR'—C(=O)—$C_1$-$C_{25}$alkyl, —C(=O)—NR'—C(=O)—$C_1$-$C_{25}$alkenyl, —C(=O)—NR'—C(=O)—$C_1$-$C_{25}$alkynyl, —C(=O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(=O)—$C_1$-$C_{25}$alkyl, —NH—NH—C(=O)—$C_2$-$C_{25}$alkenyl, —NH—NH—C(=O)—$C_2$-$C_{25}$alkynyl, —NH—NH—C(=O)—$C_6$-$C_{10}$aryl, —NH—NH—C(=O)—$C_3$-$C_{10}$heteroaryl, —NH—$C_1$-$C_{25}$alkyl-C(=O)—OH, —NH—$C_2$-$C_{25}$alkenyl-C(=O)—OH, —NH—$C_2$-$C_{25}$alkynyl-C(=O)—OH, —NH—$C_1$-$C_{25}$alkyl-C(=O)—NR'R"R'", —NH—$C_2$-$C_{25}$alkenyl-C(=O)—NR'R"R'", —NH—$C_2$-$C_{25}$alkynyl-C(=O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'"; or —$C_3$-$C_{10}$heteroaryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'".

In some embodiments, compounds of formulae herein (all formulae recited generically or specifically herein) exclude compounds wherein $R_8$ is $C_7$-$C_{12}$alkyl.

In some embodiments, $R_8$ is a $C_1$-$C_{25}$alkyl.

In some embodiments, $R_8$ is 2,2,6,6-tetramethylpiperidin-1-ol-4-yl.

In some embodiments, the compound is of the general formula (VIII):

(VIII)

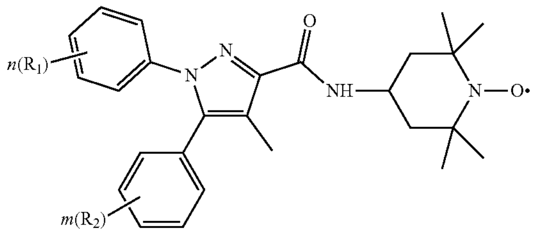

In some embodiments, n is 2 and m is 1.

In some embodiments, $R_1$ and $R_2$ are each a halide.

In some embodiments, each of $R_1$ and $R_2$ is a chloride atom.

In some embodiments, the compound is of the formula (IX):

(IX)

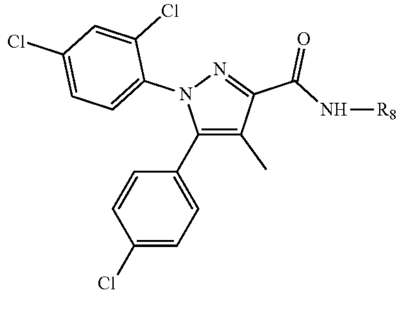

wherein $R_8$ is as defined herein.

In some embodiments, for a compound of formula (IX), $R_8$ may be:

—$C_1$-$C_{25}$alkyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R"', —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R"', —NH—$C_2$-$C_{25}$alkenyl-C(═O)—NR'R"R"', —NH—$C_2$-$C_{25}$alkynyl-C(═O)—NR'R"R"', —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R"', —NH—$C_2$-$C_{25}$alkenylene-C(═O)—NR'R"R"', —NH—$C_2$-$C_{25}$alkynylene-C(═O)—NR'R"R"', —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R"', —NHC(═O)$C_2$-$C_{25}$alkenylene-NR'R"R"', —NHC(═O)$C_2$-$C_{25}$alkynylene-NR'R"R"', —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R"'; or —$C_2$-$C_{25}$alkenyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R"', —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R"', —NH—$C_2$-$C_{25}$alkenyl-C(═O)—NR'R"R"', —NH—$C_2$-$C_{25}$alkynyl-C(═O)—NR'R"R"', —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R"', —NH—$C_2$-$C_{25}$alkenylene-C(═O)—NR'R"R"', —NH—$C_2$-$C_{25}$alkynylene-C(═O)—NR'R"R"', —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R"', —NHC(═O)$C_2$-$C_{25}$alkenylene-NR'R"R"', —NHC(═O)$C_2$-$C_{25}$alkynylene-NR'R"R"', —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R"'; or —$C_2$-$C_{25}$alkynyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R"', —C(═O)—NR'—C(═O)—$C_1$-$C_{25}$alkyl, —C(═O)—NR—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R"', —NH—$C_2$-$C_{25}$alkenyl-C(═O)—NR'R"R"', —NH—$C_2$-$C_{25}$alkynyl-C(═O)—NR'R"R"', —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'"; or —$C_6$-$C_{10}$aryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_1$-$C_{25}$alkenyl-C(═O)—NR'R"R'", —NH—$C_1$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_1$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'"; or —$C_3$-$C_{10}$heteroaryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-

$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'".

In some embodiments, $R_8$ is 2,2,6,6-tetramethylpiperidin-1-ol-4-yl.

In some embodiments, the compound is of the formula (X):

(X)

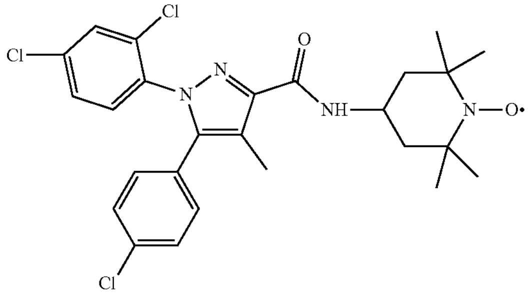

In some embodiments, in a compound of formula (I):

each of $R_1$ and $R_2$, independently of the other is a group selected from H, a halide and —CN;

each of n and m, independently of the other, is an integer between 0 and 5, designating the number of substituents on the ring;

X is selected from a nitrogen atom (or a nitrogen containing group) and CH; or X—$R_4$ may optionally be C═$R_4$;

and $R_3$ is H or a carbon containing group and $R_4$ is a nitrogen containing group.

In some embodiments, X is CH and $R_4$ is a carbon containing group having between 1 and 3 carbon atoms.

In some embodiments, $R_3$ is H.

In some embodiments, the compound is of the general formula (XI):

(XI)

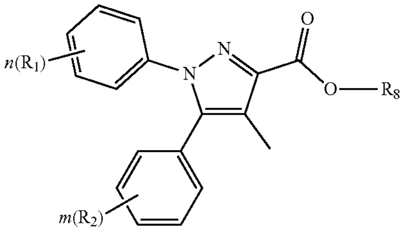

wherein each of $R_1$, $R_2$, n, m and $R_8$ is as defined herein, optionally excluding compounds wherein $R_8$ is $C_7$-$C_{12}$alkyl.

In some embodiments, for a compound of formula (XI), $R_8$ may be:

—$C_1$-$C_{25}$alkyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'"; or —$C_2$-$C_{25}$alkenyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'"; or —$C_2$-$C_{25}$alkynyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'"; or —$C_6$-$C_{10}$aryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C (=O)—O—$C_1$-$C_{25}$alkyl, —NHC(=O)$C_1$-$C_{25}$alkyl, —NHC(=O)$C_2$-$C_{25}$alkenyl, —NHC(=O)$C_2$-$C_{25}$alkynyl, —NHC(=O)$C_1$-$C_{25}$alkylene-NR'R"R'", —NHC(=O)$C_2$-$C_{25}$alkenylene-NR'R"R'", —NHC(=O)$C_2$-$C_{25}$alkynylene-NR'R"R'", —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C$(CH_3)_2$—O-aryl-Cl, —NHC(=O)$CH_2C(CH_3)_2$—O-aryl-Cl, idebenonyl-derivative, -pyridine-3-C(=O)—OH and —NR'R"R'"; or —$C_3$-$C_{10}$heteroaryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(=O)—, —C(=O)—$C_1$-$C_{25}$alkyl, —C(=O)—O—$C_1$-$C_5$alkyl, —C(=O)—O—$C_1$-$C_5$alkenyl, —C(=O)—O—$C_1$-$C_5$alkynyl, —C(=O)—NR'R"R'", —C(=O)—NR'—C(=O)—$C_1$-$C_{25}$alkyl, —C(=O)—NR'—C(=O)—$C_1$-$C_{25}$alkenyl, —C(=O)—NR'—C(=O)—$C_1$-$C_{25}$alkynyl, —C(=O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(=O)—$C_1$-$C_{25}$alkyl, —NH—NH—C(=O)—$C_2$-$C_{25}$alkenyl, —NH—NH—C(=O)—$C_2$-$C_{25}$alkynyl, —NH—NH—C(=O)—$C_6$-$C_{10}$aryl, —NH—NH—C(=O)—$C_3$-$C_{10}$heteroaryl, —NH—$C_1$-$C_{25}$alkyl-C(=O)—OH, —NH—$C_2$-$C_{25}$alkenyl-C(=O)—OH, —NH—$C_2$-$C_{25}$alkynyl-C(=O)—OH, —NH—$C_1$-$C_{25}$alkyl-C(=O)—NR'R"R'", —NH—$C_2$-$C_{25}$alkenyl-C(=O)—NR'R"R'", —NH—$C_2$-$C_{25}$alkynyl-C(=O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(=O)—$C_1$-$C_{25}$alkyl, —NH—$C_2$-$C_{25}$alkenyl-NH—C(=O)—$C_1$-$C_{25}$alkyl, —NH—$C_2$-$C_{25}$alkynyl-NH—C(=O)—$C_1$-$C_{25}$alkyl, —NH—$C_1$-$C_{25}$alkyl-NH—C(=O)—$C_6$-$C_{10}$aryl, —NH—$C_2$-$C_{25}$alkenyl-NH—C(=O)—$C_6$-$C_{10}$aryl, —NH—$C_2$-$C_{25}$alkynyl-NH—C(=O)—$C_6$-$C_{10}$aryl, —NH—$C_1$-$C_{25}$alkyl-NH—C(=O)—$C_3$-$C_{10}$heteroaryl, —NH—$C_2$-$C_{25}$alkenyl-NH—C(=O)—$C_3$-$C_{10}$heteroaryl, —NH—$C_2$-$C_{25}$alkynyl-NH—C(=O)—$C_3$-$C_{10}$heteroaryl, —NH—$C_1$-$C_{25}$alkylene-C(=O)—NR'R"R'", —NH—$C_2$-$C_{25}$alkenylene-C(=O)—NR'R"R'", —NH—$C_2$-$C_{25}$alkynylene-C(=O)—NR'R"R'", —NH—$C_1$-$C_{25}$alkylene-C(=O)—O—$C_1$-$C_{25}$alkyl, —NH—$C_2$-$C_{25}$alkenylene-C(=O)—O—$C_1$-$C_{25}$alkyl, —NH—$C_2$-$C_{25}$alkynylene-C(=O)—O—$C_1$-$C_{25}$alkyl, —NHC(=O)$C_1$-$C_{25}$alkyl, —NHC(=O)$C_2$-$C_{25}$alkenyl, —NHC(=O)$C_2$-$C_{25}$alkynyl, —NHC(=O)$C_1$-$C_{25}$alkylene-NR'R"R'", —NHC(=O)$C_2$-$C_{25}$alkenylene-NR'R"R'", —NHC(=O)$C_2$-$C_{25}$alkynylene-NR'R"R'", —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C$(CH_3)_2$—O-aryl-Cl, —NHC(=O)$CH_2C(CH_3)_2$—O-aryl-Cl, idebenonyl-derivative, -pyridine-3-C(=O)—OH and —NR'R"R'".

In some embodiments, $R_8$ is a $C_1$-$C_{25}$alkyl.

In some embodiments, $R_8$ is 2,2,6,6-tetramethylpiperidin-1-ol-4-yl.

In some embodiments, the compound is of the general formula (XII):

(XII)

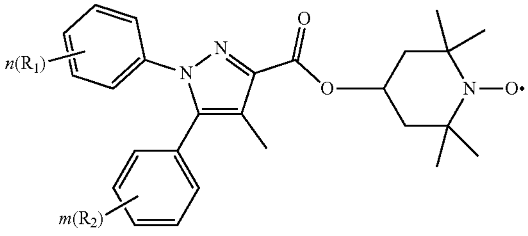

In some embodiments, in a compound of formula (XI), $R_8$ is an idebenonyl derivative.

In some embodiments, the compound is of the formula (XIII):

(XIII)

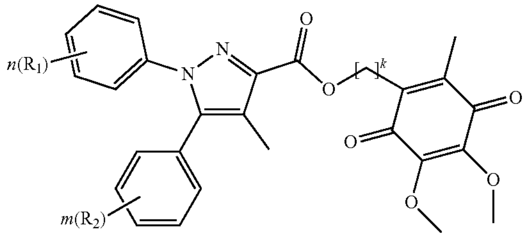

wherein each of $R_1$, $R_2$, n and m are as defined above and wherein k is an integer between 0 to 25.

In some embodiments, n is 2 and m is 1.

In some embodiments, $R_1$ and $R_2$ are each a halide.

In some embodiments, each of $R_1$ and $R_2$ is a chloride atom.

In some embodiments, the compound is of the general formula (XIV):

(XIV)

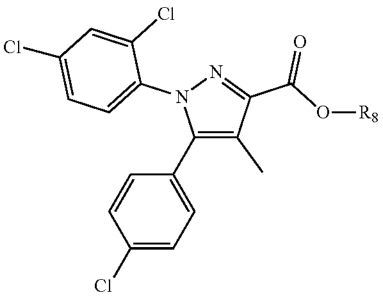

wherein $R_8$ is as defined herein.

In some embodiments, for a compound of formula (XIV), $R_8$ may be:

—$C_1$-$C_{25}$alkyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'"; or —$C_2$-$C_{25}$alkenyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'"; or —$C_2$-$C_{25}$alkynyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—

NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'"; or —$C_6$-$C_{10}$aryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'"; or —$C_3$-$C_{10}$heteroaryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC $(=O)C_2$-$C_{25}$alkynylene-NR'R"R"', —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C$(CH_3)_2$—O-aryl-Cl, —NHC(=O)$CH_2C(CH_3)_2$—O-aryl-Cl, idebenonyl-derivative, -pyridine-3-C(=O)—OH and —NR'R"R"'.

In some embodiments, $R_8$ is 2,2,6,6-tetramethylpiperidin-1-ol-4-yl.

In some embodiments, the compound is of the formula (XV):

(XV)

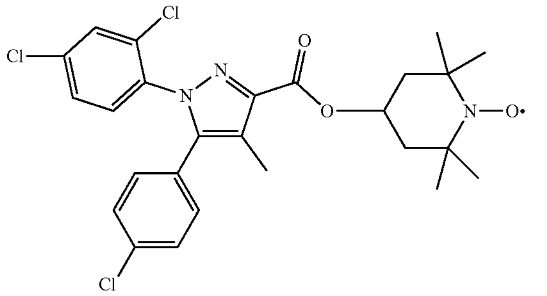

In some embodiments, $R_8$ is an idebenonyl derivative.

In some embodiments, the compound is of the formula (XVI):

(XVI)

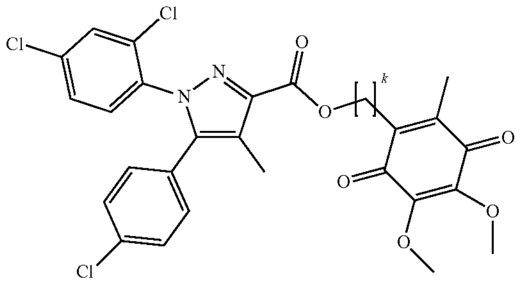

wherein k is as defined above.

In some embodiments, in a compound of formula (IV), $R_8$ is $C_1$-$C_{25}$alkyl optionally substituted by at least one functionality selected from —C(=O)—, —C(=O)—$C_1$-$C_{25}$alkyl, —C(=O)—O—$C_1$-$C_5$alkyl, —C(=O)—O—$C_1$-$C_5$alkenyl, —C(=O)—O—$C_1$-$C_5$alkynyl, —C(=O)—NR'R"R"', —C(=O)—$OR_{10}$, wherein each of R', R", R"' and $R_{10}$ is as defined above.

In some embodiments, the at least one functionality is selected from —C(=O)—NR'R"R"', —C(=O)—$C_1$-$C_{25}$alkyl and —C(=O)—$OR_{10}$, wherein each of R', R", R"' and $R_{10}$ is as defined above.

In some embodiments, R' is H, R" is absent and R"' is $R_{11}$, wherein $R_{11}$ is selected from H or a $C_1$-$C_{25}$alkyl, $C_2$-$C_{25}$alkenyl, $C_2$-$C_{25}$alkynyl, $C_6$-$C_{10}$aryl, each of which being optionally substituted by at least one functionality selected from an hydroxyl, an amine, a halide, $C_1$-$C_5$alkyl, $C_2$-$C_5$alkenyl, $C_2$-$C_5$alkynyl, —C(=O)—, —C(=O)—$C_1$-$C_{25}$alkyl, —C(=O)—O—$C_1$-$C_5$alkyl, —C(=O)—O—$C_1$-$C_5$alkenyl, —C(=O)—O—$C_1$-$C_5$alkynyl, —C(=O)—NR'R"R"', —C(=O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(=O)$CH_2$C$(CH_3)_2$—O-Aryl-$C_1$, idebenonyl-derivative, -pyridine-3-C(=O)—OH and —NR'R"R"', and wherein R', R", R"' and $R_{10}$ are as defined above.

In some embodiments, the compound is of the general formula (XVII):

(XVII)

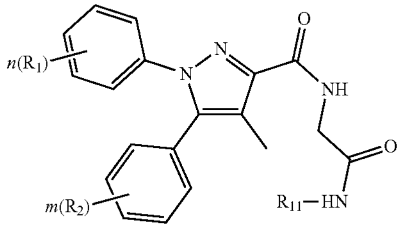

wherein each of $R_1$, $R_2$, n, m and $R_{11}$ is as defined herein.

In some embodiments, n is 2 and m is 1.

In some embodiments, $R_1$ and $R_2$ are each a halide.

In some embodiments, each of $R_1$ and $R_2$ is a chloride atom.

In some embodiments, the compound is of the general formula (XVIII):

(XVIII)

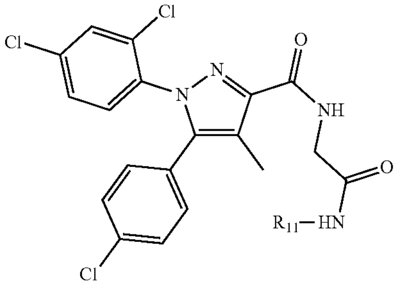

wherein $R_{11}$ is as defined herein.

In some embodiments, $R_{11}$ is selected from H or a $C_1$-$C_{25}$alkyl, $C_2$-$C_{25}$alkenyl, $C_2$-$C_{25}$alkynyl, $C_6$-$C_{10}$aryl, each of which being optionally substituted by at least one functionality selected from an hydroxyl, an amine, a halide, $C_1$-$C_5$alkyl, $C_2$-$C_5$alkenyl, $C_2$-$C_5$alkynyl, —C(=O)—, —C(=O)—$C_1$-$C_{25}$alkyl, —C(=O)—O—$C_1$-$C_5$alkyl, —C(=O)—O—$C_1$-$C_5$alkenyl, —C(=O)—O—$C_1$-$C_5$alkynyl, —C(=O)—NR'R"R"', —C(=O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(=O)$CH_2$C$(CH_3)_2$—O-Aryl-$C_1$, idebenonyl-derivative, -pyridine-3-C(=O)—OH and —NR'R"R"'.

In some embodiments, in a compound of formula (XI), $R_8$ is —$C_1$-$C_{25}$alkyl optionally substituted by at least one functionality selected from —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—$OR_{10}$, wherein each of R', R", R'" and $R_{10}$ is as defined above.

In some embodiments, the at least one functionality is selected from —C(═O)—NR'R"R'", —C(═O)—$C_1$-$C_{25}$alkyl and —C(═O)—$OR_{10}$, wherein each of R', R", R'" and $R_{10}$ is as defined above.

In some embodiments, the compound is of the general formula (XIX):

(XIX)

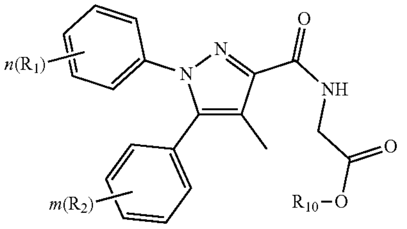

wherein each of $R_1$, $R_2$, n, m and $R_{10}$ is as defined herein.

In some embodiments, $R_{10}$ is selected from H, —$C_1$-$C_{25}$alkyl, —$C_2$-$C_{25}$alkenyl, —$C_2$-$C_{25}$alkynyl, —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-aryl-Cl, idebenonyl-derivative, -pyridine-3-C(═O)—OH and —NR'R"R'";

each of R', R" and R'" is independently selected from —H, $C_1$-$C_5$alkyl, $C_2$-$C_5$alkenyl, $C_2$-$C_5$alkynyl, —C(═O)—$C_2$-$C_{25}$alkyl, —C(═O)—$C_2$-$C_{25}$alkenyl and $C_5$-$C_{25}$alkynyl; or wherein one of R', R" and R'" is absent.

In some embodiments, n is 2 and m is 1.

In some embodiments, $R_1$ and $R_2$ are each a halide.

In some embodiments, each of $R_1$ and $R_2$ is a chloride atom.

In some embodiments, the compound is of the general formula (XX):

(XX)

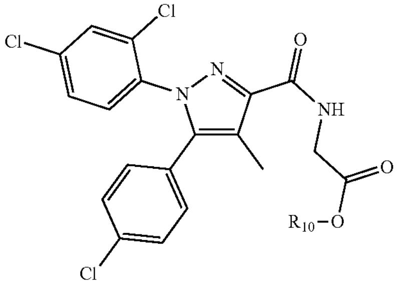

wherein $R_{10}$ is as defined herein.

In some embodiments, $R_{10}$ is selected from —H, —$C_1$-$C_{25}$alkyl, —$C_2$-$C_{25}$alkenyl, —$C_2$-$C_{25}$alkynyl, —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-aryl-Cl, idebenonyl-derivative, -pyridine-3-C(═O)—OH and —NR'R"R'";

each of R', R" and R'" is independently selected from —H, $C_1$-$C_5$alkyl, $C_2$-$C_5$alkenyl, $C_2$-$C_5$alkynyl, —C(═O)—$C_2$-$C_{25}$alkyl, —C(═O)—$C_2$-$C_{25}$alkenyl and $C_5$-$C_{25}$alkynyl; or wherein one of R', R" and R'" is absent.

In some embodiments, in a compound of formula (IV), $R_8$ is $C_1$-$C_{25}$alkyl optionally substituted by at least one functionality selected from an hydroxyl, an amine, —$OR_{10}$, and a halide.

In some embodiments, the at least one functionality is a hydroxyl, an amine or —$OR_{10}$, wherein the amine having the structure —NR'R"R'", wherein each of R', R", R'" and $R_{10}$ is as defined above.

In some embodiments, R' is H, R" is absent and R'" is $R_{11}$, wherein $R_{11}$ is selected from —H, a —$C_1$-$C_{25}$alkyl, —$C_2$-$C_{25}$alkenyl, —$C_2$-$C_{25}$alkynyl, —$C_6$-$C_{10}$aryl, each of which being optionally substituted by at least one functionality selected from an hydroxyl, an amine, a halide, $C_1$-$C_5$alkyl, $C_2$-$C_5$alkenyl, $C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—OR 0, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2$C$(CH_3)_2$—O-Aryl-$C_1$, idebenonyl-derivative, -pyridine-3-C(═O)—OH and —NR'R"R'", and wherein R', R", R'" and $R_{10}$ are as defined above.

In some embodiments, the compound is of the general formula (XXI):

(XXI)

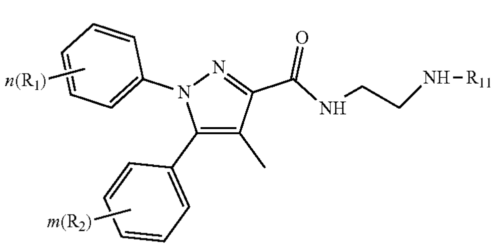

wherein each of $R_1$, $R_2$, n, m and $R_{11}$ is as defined herein.

In some embodiments, $R_{11}$ is selected from H or a $C_1$-$C_{25}$alkyl, $C_2$-$C_{25}$alkenyl, $C_2$-$C_{25}$alkynyl, $C_6$-$C_{10}$aryl, each of which being optionally substituted by at least one functionality selected from an hydroxyl, an amine, a halide, $C_1$-$C_5$alkyl, $C_2$-$C_5$alkenyl, $C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-Aryl-$C_1$, idebenonyl-derivative, -pyridine-3-C(═O)—OH and —NR'R"R'".

In some embodiments, R' is H, R" is absent and R'" is $R_{11}$, wherein $R_{11}$ is —NHC(═O)$CH_2C(CH_3)_2$—O-Aryl-Cl.

In some embodiments, the compound is of the general formula (XXII):

(XXII)

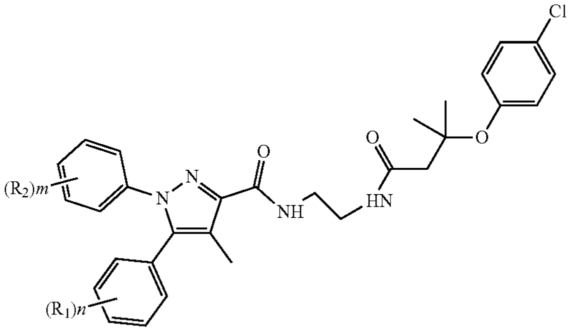

wherein each of $R_1$, $R_2$, n and m is as defined herein.

In some embodiments, n is 2 and m is 1.

In some embodiments, $R_1$ and $R_2$ are each a halide.

In some embodiments, each of $R_1$ and $R_2$ is a chloride atom.

In some embodiments, the compound is of the general formula (XXIII):

(XXIII)

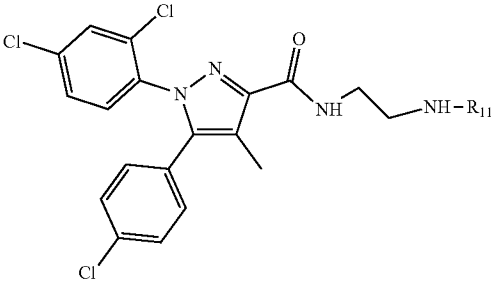

wherein $R_{11}$ is as defined herein.

In some embodiments, $R_{11}$ is selected from H or a $C_1$-$C_{25}$alkyl, $C_2$-$C_{25}$alkenyl, $C_2$-$C_{25}$alkynyl, $C_6$-$C_{10}$aryl, each of which being optionally substituted by at least one functionality selected from an hydroxyl, an amine, a halide, $C_1$-$C_5$alkyl, $C_2$-$C_5$alkenyl, $C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-Aryl-Cl, idebenonyl-derivative, -pyridine-3-C(═O)—OH and —NR'R"R'".

In some embodiments, the compound is of the formula (XXIV):

(XXIV)

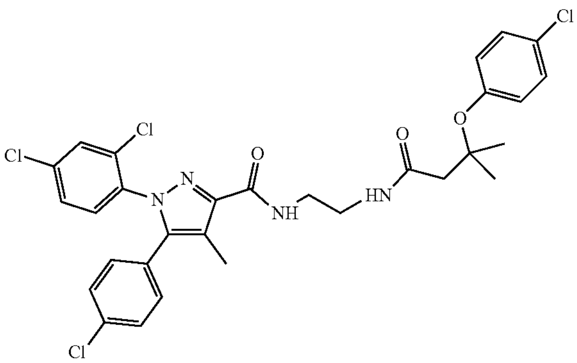

In some embodiments, in a compound of formula (XI), $R_8$ is $C_1$-$C_{25}$alkyl optionally substituted by at least one functionality selected from an hydroxyl, an amine, —$OR_{10}$, and a halide.

In some embodiments, the at least one functionality is a hydroxyl, an amine or —$OR_{10}$, wherein the amine having the structure NR'R"R'", wherein each of R', R", R'" and $R_{10}$ is as defined above.

In some embodiments, the compound is of the general formula (XXV):

(XXV)

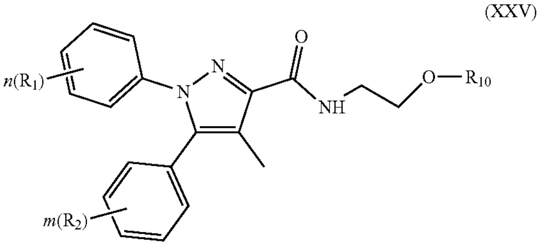

wherein each of $R_1$, $R_2$, n, m and $R_{10}$ is as defined herein.

In some embodiments, $R_{10}$ is selected from H, —$C_1$-$C_{25}$alkyl, —$C_2$-$C_{25}$alkenyl, —$C_2$-$C_{25}$alkynyl, —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-aryl-Cl, idebenonyl-derivative, -pyridine-3-C(═O)—OH and —NR'R"R'";

each of R', R" and R'" is independently selected from —H, $C_1$-$C_5$alkyl, $C_2$-$C_5$alkenyl, $C_2$-$C_5$alkynyl, —C(═O)—$C_2$-$C_{25}$alkyl, —C(═O)—$C_2$-$C_{25}$alkenyl and $C_5$-$C_{25}$alkynyl; or wherein one of R', R" and R'" is absent.

In some embodiments, n is 2 and m is 1.

In some embodiments, $R_1$ and $R_2$ are each a halide.

In some embodiments, each of $R_1$ and $R_2$ is a chloride atom.

In some embodiments, the compound is of the general formula (XXVI):

(XXVI)

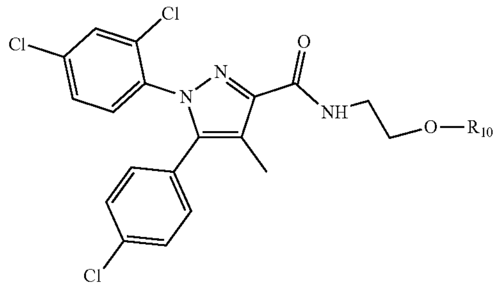

wherein $R_{10}$ is as defined herein.

In some embodiments, $R_{10}$ is selected from H, $—C_1-C_{25}$alkyl, $—C_2-C_{25}$alkenyl, $—C_2-C_{25}$alkynyl, $—C_6-C_{10}$aryl, each of which being optionally substituted by at least one functionality selected from an hydroxyl, an amine, a halide, $—C_1-C_5$alkyl, $—C_2-C_5$alkenyl, $—C_2-C_5$alkynyl, —C(═O)—, $—C(═O)—C_1-C_{25}$alkyl, $—C(═O)—O—C_1-C_5$alkyl, $—C(═O)—O—C_1-C_5$alkenyl, $—C(═O)—O—C_1-C_5$alkynyl, —C(═O)—NR'R"R'", $—O—C_1-C_5$alkyl, $—O—C_1-C_5$alkenyl, $—O—C_1-C_5$alkynyl, —S—, $—S—C_1-C_5$alkyl, $—S—C_1-C_5$alkenyl, $—S—C_1-C_5$alkynyl, $—ONO_2$, $—NO_2$, 2,2,6,6-tetramethylpiperidin-1-ol-4-yl, $—NHC(═O)CH_2C(CH_3)_2—O$-aryl-Cl, idebenonyl-derivative, -pyridine-3-C(═O)—OH and —NR'R"R'";

each of R', R" and R'" is independently selected from —H, $C_1-C_5$alkyl, $C_2-C_5$alkenyl, $C_2-C_5$alkynyl, $—C(═O)—C_2-C_{25}$alkyl, $—C(═O)—C_2-C_{25}$alkenyl and $C_5-C_{25}$alkynyl; or wherein one of R', R" and R'" is absent.

In some embodiments, the compound is of the general formula (XXVII):

(XXVII)

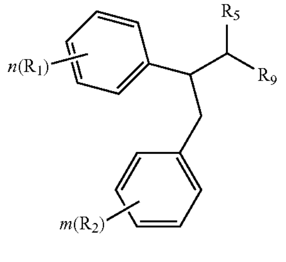

wherein each of $R_1$, $R_2$, n, m is as defined herein; $R_5$ is absent or selected from H, $—C_1-C_3$alkyl, $—C(═O)—O—R_8$, $—C(═O)—NR'—R_8$, halide, CN, and OH; and $R_9$ is selected from $—C(═O)—O—R_8$, $—C(═O)—NR'—R_8$, $—NH—C(═O)—O—R_8$, $—NH—C(═O)—NR'—R_8$, $—O—C(═O)—O—R_8$ and $—O—C(═O)—NR'—R_8$; $R_8$ is as defined herein.

In some embodiments, $R_5$ is a $—C_1-C_3$alkyl and $R_9$ is selected from $—C(═O)—C_1-C_{25}$alkyl, $—C(═O)—O—R_8$, $—C(═O)—NR'—R_8$, $—NH—C(═O)—O—R_8$, $—NH—C(═O)—NR'—R_8$, $—O—C(═O)—O—R_8$ and $—O—C(═O)—NR'—R_8$; $R_8$ is as defined herein.

In some embodiments, $R_9$ is $—NH—C(═O)—O—R_8$, $—NH—C(═O)—NR'—R_8$, $—O—C(═O)—O—R_8$ or $—O—C(═O)—NR'—R_8$; $R_8$ is as defined herein.

In some embodiments, $R_9$ is $—NH—C(═O)—O—R_8$ or $—O—C(═O)—O—R_8$; $R_8$ is as defined herein.

In some embodiments, the compound is of the general formula (XXVIII):

(XXVIII)

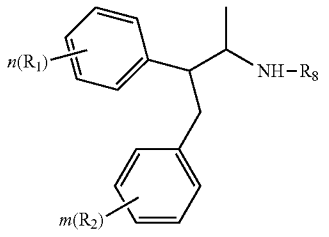

wherein each of $R_1$, $R_2$, n, m and $R_8$ is as defined herein.

In some embodiments, $R_8$ is $—C_1-C_{25}$alkyl.

In some embodiments, $R_8$ is $—C_2-C_{25}$alkenyl.

In some embodiments, $R_8$ is $—C_2-C_{25}$alkynyl.

In some embodiments, $R_8$ is $—C_6-C_{10}$aryl.

In some embodiments, $R_8$ is $C_3-C_{10}$heteroaryl.

In some embodiments, $R_8$ is $—C_1-C_{25}$alkyl substituted by at least one functionality selected from an hydroxyl, an amine, a halide, $—ONO_2$, $—NO_2$, —S—, $—S—C_1-C_5$alkyl, $—S—C_1-C_5$alkenyl, $—S—C_1-C_5$alkynyl, —C(═O)—, $—C(═O)—C_1-C_{25}$alkyl, $—C(═O)—O—C_1-C_5$alkyl, $—C(═O)—O—C_1-C_5$alkenyl, $—C(═O)—O—C_1-C_5$alkynyl, —C(═O)—NR'R"R'", $—C(═O)—NR'—C(═O)—C_1-C_{25}$alkyl, $—C(═O)—NR'—C(═O)—C_1-C_{25}$alkenyl, $—C(═O)—NR—C(═O)—C_1-C_{25}$alkynyl, $—C(═O)—OR_{10}$, $—O—C_1-C_5$alkyl, $—O—C_1-C_5$alkenyl, $—O—C_1-C_5$alkynyl, $—NH—NH_2$, $—NH—NH—C(═O)—C_1-C_{25}$alkyl, $—NH—NH—C(═O)—C_2-C_{25}$alkenyl, $—NH—NH—C(═O)—C_2-C_{25}$alkynyl, $—NH—NH—C(═O)—C_6-C_{10}$aryl, $—NH—NH—C(═O)—C_3-C_{10}$heteroaryl, $—NH—C_1-C_{25}$alkyl-C(═O)—OH, $—NH—C_2-C_{25}$alkenyl-C(═O)—OH, $—NH—C_2-C_{25}$alkynyl-C(═O)—OH, $—NH—C_1-C_{25}$alkyl-C(═O)—NR'R"R'", $—NH—C_2-C_{25}$alkenyl-C(═O)—NR'R"R'", $—NH—C_2-C_{25}$alkynyl-C(═O)—NR'R"R'", $—NH—C_1-C_{25}$alkyl-$NH_2$, $—NH—C_2-C_{25}$alkenyl-$NH_2$, $—NH—C_2-C_{25}$alkynyl-$NH_2$, $—NH—C_1-C_{25}$alkyl-$NH—C(═O)—C_1-C_{25}$alkyl, $—NH—C_2-C_{25}$alkenyl-$NH—C(═O)—C_1-C_{25}$alkyl, $—NH—C_2-C_{25}$alkynyl-$NH—C(═O)—C_1-C_{25}$alkyl, $—NH—C_1-C_{25}$alkyl-$NH—C(═O)—C_6-C_{10}$aryl, $—NH—C_2-C_{25}$alkenyl-$NH—C(═O)—C_6-C_{10}$aryl, $—NH—C_2-C_{25}$alkynyl-$NH—C(═O)—C_6-C_{10}$aryl, $—NH—C_1-C_{25}$alkyl-$NH—C(═O)—C_3-C_{10}$heteroaryl, $—NH—C_2-C_{25}$alkenyl-$NH—C(═O)—C_3-C_{10}$heteroaryl, $—NH—C_2-C_{25}$alkynyl-$NH—C(═O)—C_3-C_{10}$heteroaryl, $—NH—C_1-C_{25}$alkylene-C(═O)—NR'R"R'", $—NH—C_2-C_{25}$alkenylene-C(═O)—NR'R"R'", $—NH—C_2-C_{25}$alkynylene-C(═O)—NR'R"R'", $—NH—C_1-C_{25}$alkylene-$C(═O)—O—C_1-C_{25}$alkyl, $—NH—C_2-C_{25}$alkenylene-$C(═O)—O—C_1-C_{25}$alkyl, $—NH—C_2-C_{25}$alkynylene-$C(═O)—O—C_1-C_{25}$alkyl, $—NHC(═O)C_1-C_{25}$alkyl, $—NHC(═O)C_2-C_{25}$alkenyl, $—NHC(═O)C_2-C_{25}$alkynyl, $—NHC(═O)C_1-C_{25}$alkylene-NR'R"R'", $—NHC(═O)C_2-C_{25}$alkenylene-NR'R"R'", $—NHC(═O)C_2-C_{25}$alkynylene-NR'R"R'", $—NHC(═O)C_1-C_{25}$alkylene-OH, $—NHC(═O)C_2-C_{25}$alkenylene-OH, $—NHC(═O)C_2-C_{25}$alkynylene-OH, $—NHC(═O)C_6-C_{10}$aryl, $—NHC(═O)C_3-C_{10}$heteroaryl, $—NHC(═O)C_1-C_{25}$alkylene-$C_6-C_{10}$aryl, $—NHC(═O)C_2-C_{25}$alkenylene-$C_6-C_{10}$aryl, $—NHC(═O)C_2-C_{25}$alkynylene-$C_6-C_{10}$aryl, —NHC(═O)

$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'".

In some embodiments, $R_8$ is —$C_2$-$C_{25}$alkenyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'".

In some embodiments, $R_8$ is —$C_2$-$C_{25}$alkynyl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'".

In some embodiments, $R_8$ is —$C_6$-$C_{10}$aryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'".

In some embodiments, $R_8$ is $C_3$-$C_{10}$heteroaryl substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C($CH_3$)$_2$—O-aryl-Cl, —NHC(═O)$CH_2$C($CH_3$)$_2$—O-aryl-Cl, idebenonyl-derivative, -pyridine-3-C(═O)—OH and —NR'R"R'".

In some embodiments, each of n and m is 1.

In some embodiments, $R_1$ is CN and $R_2$ is a halide.

In some embodiments, $R_2$ is a chloride atom.

In some embodiments, the compound is of the formula (XXIX):

(XXIX)

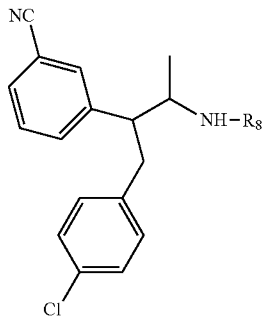

wherein $R_8$ is as defined herein.

In some embodiments, in a compound of formula (I) each of $R_1$ and $R_2$, independently of the other is a group selected from H, a halide and —CN;

each of n and m, independently of the other, is an integer between 0 and 5, designating the number of substituents on the ring;

X is CH, $CH_2$ or wherein the group C—$R_4$ is C═$R_4$;

$R_3$ is H or a carbon containing group having between 1 and 3 carbon atoms, further optionally substituted;

$R_4$ is a nitrogen atom or a nitrogen containing group, or a carbon containing group having between 1 and 3 carbon atoms, further optionally substituted;

or $R_3$ and $R_4$ together with the atoms to which they are bonded (carbon atom and X, respectively) form a 5- or 6-membered carbocyclic ring optionally containing between 1 and 3 heteroatoms selected from N, O and S.

In some embodiments, X—$R_4$ is C═$R_4$ and $R_4$ is a nitrogen atom.

In some embodiments, $R_3$ is a carbon containing group and $R_4$ is a nitrogen containing group.

In some embodiments, $R_3$ and $R_4$ together with the atoms to which they are bonded form a 5-membered carbocyclic ring optionally containing 1 or 2 nitrogen atoms.

In some embodiments, the compound is of the general formula (XXX):

(XXX)

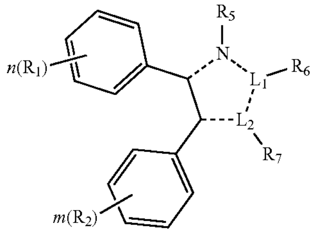

wherein one of $L_1$ and $L_2$ is a nitrogen atom and the other of $L_1$ and $L_2$ is a carbon atom (being selected from C, CH or $CH_2$);

each of $R_5$, $R_6$ and $R_7$, independently of the other, may be absent or selected from —H, $C_1$-$C_3$alkyl, —C(═O)—O—$R_8$, —C(═O)—NR'—$R_8$, halide, CN, OH, and NR'R";

and wherein $R_8$, R', R" and R'" is as defined above. and wherein each bond between C—N, N-$L_1$, $L_1$-$L_2$ and $L_2$-C (designated ---) is a single or double bond.

In some embodiments, $L_1$ is nitrogen atom and $L_2$ is a carbon atom.

In some embodiments, $L_1$ is a nitrogen and $L_2$ is a carbon atom, the bond between C and N is a double bond, the bond between N and $L_1$ is a single bond, and the bond between $L_1$ and $L_2$ is a single bond.

In some embodiments, the compound is of formula (XXXI):

(XXXI)

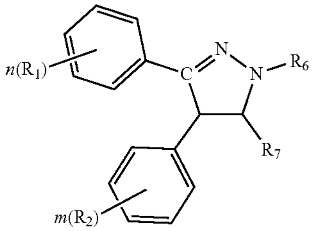

wherein each of $R_1$, $R_2$, n, m, $R_6$ and $R_7$ are as defined herein.

In some embodiments, $R_7$ is H and $R_6$ is selected from —$C_1$-$C_3$alkyl, —C(═O)—O—$R_8$, —C(═O)—NR'—$R_8$, a halide, —CN, —OH, and —NR'R"; and wherein $R_8$ is as defined above.

In some embodiments, $R_6$ is a substituted —$C_1$-$C_3$alkyl and $R_7$ is H.

In some embodiments, the compound is of the formula (XXXII):

(XXXII)

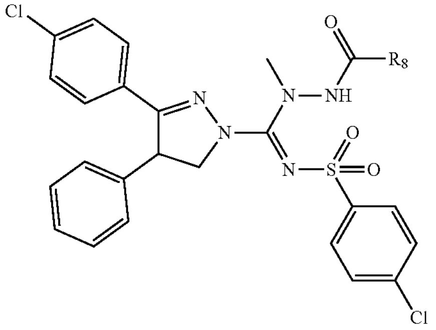

wherein $R_8$ is as defined herein.

In some embodiments, the compound is of the formula (XXXIII):

(XXXIII)

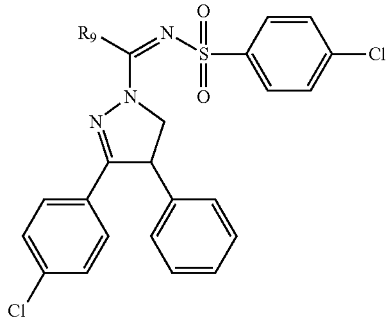

wherein $R_9$ is selected from O—$R_8$ and —NR'—$R_8$; $R_8$ is as defined herein.

In some embodiments, the compound is of the formula (XXXIV):

(XXXIV)

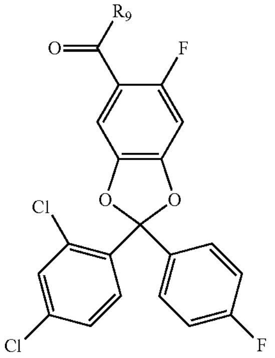

wherein $R_9$ is selected from —O—$R_8$ and —NR'—$R_8$; wherein each of R' and $R_8$ is as defined herein.

In some embodiments, the compound is of the formula (XXXV):

(XXXV)

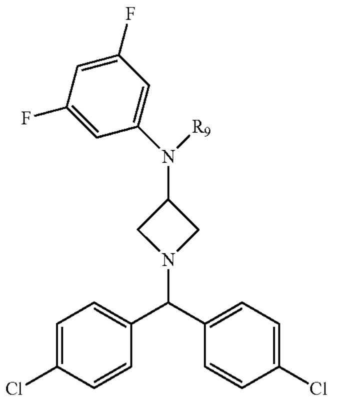

wherein $R_9$ is selected from —O—$R_8$ and —NR'—$R_8$; wherein each of R' and $R_8$ is as defined herein.

In some embodiments, the compound is of the formula (XXXVI):

(XXXVI)

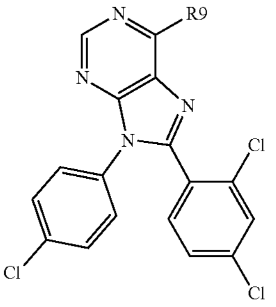

wherein $R_9$ is selected from —O—$_8$ and —NR'—$R_8$; wherein each of R' and $R_8$ is as defined herein.

As stated herein, the invention provides a compound that is of the general formula (II), as defined herein. In other words, the compound is of the formula:

(II)

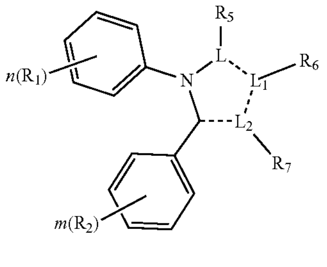

wherein one of L, $L_1$ and $L_2$ is a nitrogen atom and the others of L, $L_1$ and $L_2$ are each a carbon atom (being selected from C, CH or $CH_2$);

each of $R_5$, $R_6$ and $R_7$, independently of the other, may be selected from —H, —C(═O)—OH, —C(═O)—O—$R_8$, —C(═O)—NR'$R_8$, halide, —CN, —OH, and —NR'R"; or one of R5 and R6 or R6 and R7 together with the atoms to which they bond may form a 5-, 6-, 7- or 8-membered carbocyclic ring optionally containing between 1 and 3 heteroatoms selected from N, O and S;

the 5-, 6-, 7- or 8-membered carbocyclic ring is further optionally substituted by at least one functionality B selected from —H, —$C_1$-$C_{25}$alkyl, —$C_2$-$C_{25}$alkenyl, —$C_2$-$C_{25}$alkynyl, —$C_6$-$C_{10}$aryl, an hydroxyl, an amine, a halide, —$ONO_2$, —$NO_2$, —S—, —S—$C_1$-$C_5$alkyl, —S—$C_2$-$C_5$alkenyl, —S—$C_2$-$C_5$alkynyl, —C(═O)—, —C(═O)—$C_1$-$C_{25}$alkyl, —C(═O)—O—$C_1$-$C_5$alkyl, —C(═O)—O—$C_2$-$C_5$alkenyl, —C(═O)—O—$C_2$-$C_5$alkynyl, —C(═O)—NR'R"R'", —C(═O)—NR'—C(═O)—$C_1$-$C_{25}$alkyl, —C(═O)—NR'—C(═O)—$C_2$-$C_{25}$alkenyl, —C(═O)—NR'—C(═O)—$C_2$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'";

the 5-, 6-, 7- or 8-membered carbocyclic ring may be optionally substituted by at least one functionality B selected from structures (A) through (H):

(A)

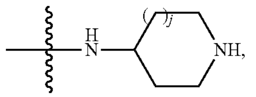

(B)

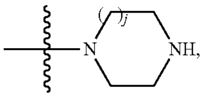

(C)

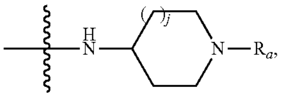

(D)

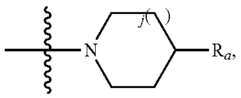

(E)

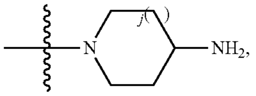

(F)

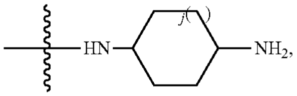

(G)

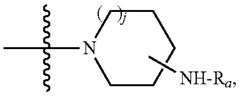

and (H)

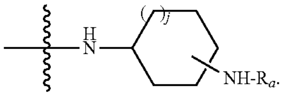

wherein in each functionality (A) through (H), the wavy line indicates point or bond of connectivity, j is 0 or 1 and Ra is selected from H, —$C_1$-$C_{25}$alkyl, —$C_2$-$C_{25}$alkenyl, —$C_2$-$C_{25}$alkynyl, C(═O)—$C_6$-$C_{10}$aryl and C(═O)—$C_3$-$C_{10}$heteroaryl, wherein in functionalities (G) and (H) the pendant —NH—Ra group may appear between 1 and 11 times at any position along the carbocycle (in some embodiments, it may be positioned at a ring atom once removed, twice removed or three times removed from the existing group or endocyclic N atom; in some embodiments, the position of the functionality is 1, 2 or 1, 3 or 1, 4, wherein 1 designates the position of the existing group or the endocyclic N atom);

one of $R_5$, $R_6$ and $R_7$ may be absent;

$R_8$ is selected from H, —$C_1$-$C_{25}$alkyl, —$C_2$-$C_{25}$alkenyl, —$C_2$-$C_{25}$alkynyl, —$C_6$-$C_{10}$aryl and $C_3$-$C_{10}$heteroaryl, each of which being optionally substituted by at least one functionality selected from an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2$C$(CH_3)_2$—O-aryl-Cl, idebenonyl-derivative, -pyridine-3-C(═O)—OH and —NR'R"R'";

$R_{10}$ is selected from —H, —$C_1$-$C_{25}$alkyl, —$C_2$-$C_{25}$alkenyl, —$C_2$-$C_{25}$alkynyl, —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NWR"R'", —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2$C$(CH_3)_2$—O-aryl-Cl, idebenonyl-derivative, -pyridine-3-C(═O)—OH and —NR'R"R'";

each of R', R" and R'" is independently selected from —H, $C_1$-$C_5$alkyl, $C_2$-$C_5$alkenyl, $C_2$-$C_5$alkynyl, —C(═O)—$C_2$-$C_{25}$alkyl, —C(═O)—$C_2$-$C_{25}$alkenyl and $C_5$-$C_{25}$alkynyl; or wherein one of R', R" and R'" is absent; and wherein each bond between N-L, L-$L_1$, $L_1$-$L_2$ and $L_2$-C (designated ---) is a single or double bond.

In some embodiments, in a compound of formula (II), $L_2$ is a nitrogen atom and each of L and L is a carbon atom. In some embodiments, $R_7$ is absent and $R_5$ and $R_6$ together with the atoms to which they bond form a 5-, 6-, 7- or 8-membered carbocyclic ring optionally containing between 1 and 3 heteroatoms selected from N, O and S. In some embodiments, the compound is of the formula (XXXVII):

(XXXVII)

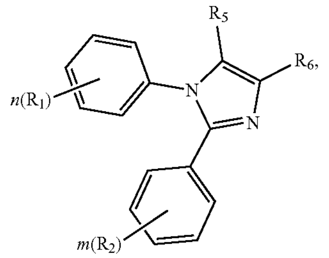

wherein each of $R_1$, $R_2$, $R_5$, $R_6$, n and m is as defined above.

In some embodiments, $R_5$ and $R_6$ together with the atoms to which they bond may form a 5-, 6-, 7- or 8-membered carbocyclic ring optionally containing between 1 and 3 heteroatoms selected from N, O and S.

In some embodiments, the compound is of formula (XXXVIII):

(XXXVIII)

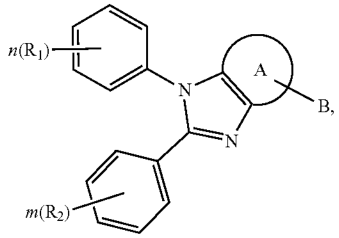

wherein each of $R_1$, $R_2$ and m is as defined above, ring A is a 5-, 6-, 7- or 8-membered carbocyclic ring optionally containing between 1 and 3 heteroatoms selected from N, O and S, and further optionally substituted by a group B selected from —H, —$C_1$-$C_{25}$alkyl, —$C_2$-$C_{25}$alkynyl, —$C_6$-$C_{10}$aryl, an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(=O)—, —C(=O)—$C_1$-$C_{25}$alkyl, —C(=O)—O—$C_1$-$C_5$alkyl, —C(=O)—O—$C_2$-$C_5$alkenyl, —C(=O)—O—$C_2$-$C_5$alkynyl, —C(=O)—NR'R"R'", —C(=O)—NR'—C(=O)—$C_1$-$C_{25}$alkyl, —C(=O)—NR'—C(=O)—$C_2$-$C_{25}$alkenyl, —C(=O)—NR'—C(=O)—$C_2$-$C_{25}$alkynyl, —C(=O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(=O)—$C_1$-$C_{25}$alkyl, —NH—NH—C(=O)—$C_2$-$C_{25}$alkenyl, —NH—NH—C(=O)—$C_2$-$C_{25}$alkynyl, —NH—NH—C(=O)—$C_6$-$C_{10}$aryl, —NH—NH—C(=O)—$C_3$-$C_{10}$heteroaryl, —NH—$C_1$-$C_{25}$alkyl-C(=O)—OH, —NH—$C_2$-$C_{25}$alkenyl-C(=O)—OH, —NH—$C_2$-$C_{25}$alkynyl-C(=O)—OH, —NH—$C_1$-$C_{25}$alkyl-C(=O)—NR'R"R'", —NH—$C_2$-$C_{25}$alkenyl-C(=O)—NR'R"R'", —NH—$C_2$-$C_{25}$alkynyl-C(=O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(=O)—$C_1$-$C_{25}$alkyl, —NH—$C_2$-$C_{25}$alkenyl-NH—C(=O)—$C_1$-$C_{25}$alkyl, —NH—$C_2$-$C_{25}$alkynyl-NH—C(=O)—$C_1$-$C_{25}$alkyl, —NH—$C_1$-$C_{25}$alkyl-NH—C(=O)—$C_6$-$C_{10}$aryl, —NH—$C_2$-$C_{25}$alkenyl-NH—C(=O)—$C_6$-$C_{10}$aryl, —NH—$C_2$-$C_{25}$alkynyl-NH—C(=O)—$C_6$-$C_{10}$aryl, —NH—$C_1$-$C_{25}$alkyl-NH—C(=O)—$C_3$-$C_{10}$heteroaryl, —NH—$C_2$-$C_{25}$alkenyl-NH—C(=O)—$C_3$-$C_{10}$heteroaryl, —NH—$C_2$-$C_{25}$alkynyl-NH—C(=O)—$C_3$-$C_{10}$heteroaryl, —NH—$C_1$-$C_{25}$alkylene-C(=O)—NR'R"R'", —NH—$C_2$-$C_{25}$alkenylene-C(=O)—NR'R"R'", —NH—$C_2$-$C_{25}$alkynylene-C(=O)—NR'R"R'", —NH—$C_1$-$C_{25}$alkylene-C(=O)—O—$C_1$-$C_{25}$alkyl, —NH—$C_2$-$C_{25}$alkenylene-C(=O)—O—$C_1$-$C_{25}$alkyl, —NH—$C_2$-$C_{25}$alkynylene-C(=O)—O—$C_1$-$C_{25}$alkyl, —NHC(=O)$C_1$-$C_{25}$alkyl, —NHC(=O)$C_2$-$C_{25}$alkenyl, —NHC(=O)$C_2$-$C_{25}$alkynyl, —NHC(=O)$C_1$-$C_{25}$alkylene-NR'R"R'", —NHC(=O)$C_2$-$C_{25}$alkenylene-NR'R"R'", —NHC(=O)$C_2$-$C_{25}$alkynylene-NR'R"R'", —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C$(CH_3)_2$—O-aryl-Cl, —NHC(=O)$CH_2$C$(CH_3)_2$—O-aryl-Cl, idebenonyl-derivative, -pyridine-3-C(=O)—OH and —NR'R"R'";

the 5-, 6-, 7- or 8-membered carbocyclic ring may be optionally substituted by at least one functionality B selected from structures (A) through (H):

(A)

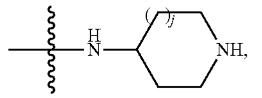

(B)

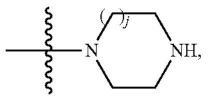

(C)

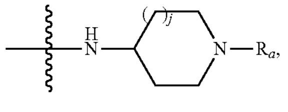

(D)

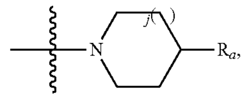

(E)

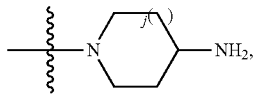

-continued (F)

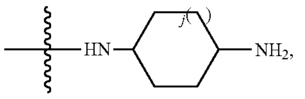

(G)

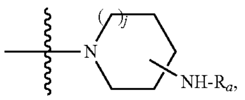

and (H)

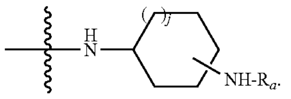

wherein in each functionality (A) through (H), the wavy line indicates point or bond of connectivity, j is 0 or 1 and Ra is selected from H, —$C_1$-$C_{25}$alkyl, —$C_2$-$C_{25}$alkenyl, —$C_2$-$C_{25}$alkynyl, C(═O)—$C_6$-$C_{10}$aryl and C(═O)—$C_3$-$C_{10}$heteroaryl, wherein in functionalities (G) and (H) the pendant —NH—Ra group may appear between 1 and 11 times at any position along the carbocycle (in some embodiments, it may be positioned at a ring atom once removed, twice removed or three times removed from the existing group or endocyclic N atom; in some embodiments, the position of the functionality is 1, 2 or 1, 3 or 1, 4, wherein 1 designates the position of the existing group or the endocyclic N atom).

In some embodiments, ring A is a 5-membered ring. In some embodiments, the ring is a heterocyclic ring comprising one or more heteroatom selected from N, O and S.

In some embodiments, ring A is a 6-membered ring. In some embodiments, the ring is a heterocyclic ring comprising one or more heteroatom selected from N, O and S. in some embodiments, the ring is an atromatic ring or a heteroaryl ring.

In some embodiments, ring A is a 7-membered ring. In some embodiments, the ring is a heterocyclic ring comprising one or more heteroatom selected from N, O and S.

In some embodiments, ring A comprises one or more double bonds.

In some embodiments, the compound is a compound of the formula (XXXIX):

(XXXIX)

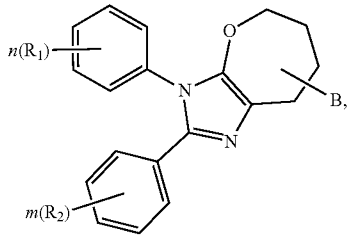

wherein each of $R_1$, $R_2$, n, m and B is as defined above.

In some embodiments, the compound is a compound of formula (XXXX):

(XXXX)

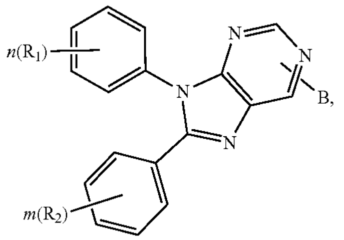

wherein wherein each of $R_1$, $R_2$, n, m and B is as defined above.

In some embodiments, the compound if a compound of formula (XXXXI):

(XXXXI)

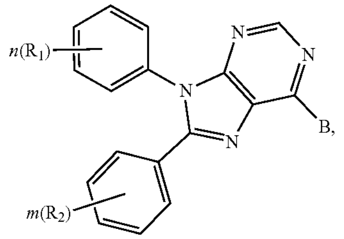

wherein wherein each of $R_1$, $R_2$, n, m and B is as defined above.

In some embodiments, the compound of formula (II) is a compound having the structure of formula (XXXXII):

(XXXXII)

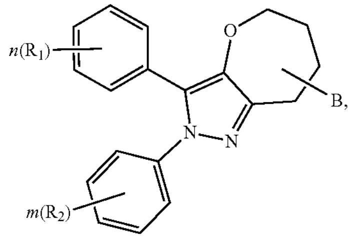

wherein each of $R_1$, $R_2$, m and B is as defined above.

In some embodiments of compounds of the invention, n is 2 and m is 1, or m is 2 and n is 1, or each of m and n is either 2 or 1. In some embodiments, $R_1$ and $R_2$ are each a halide. In some embodiments, each of $R_1$ and $R_2$ is a chloride atom.

In some embodiments of compounds of the invention, n and m together represent 2 or 3 halide atoms. In some embodiments, the halide atoms are each a chloride atom.

In some embodiments, the following compounds of the invention are provided:
A
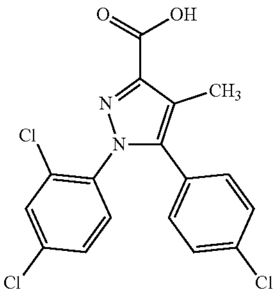
B
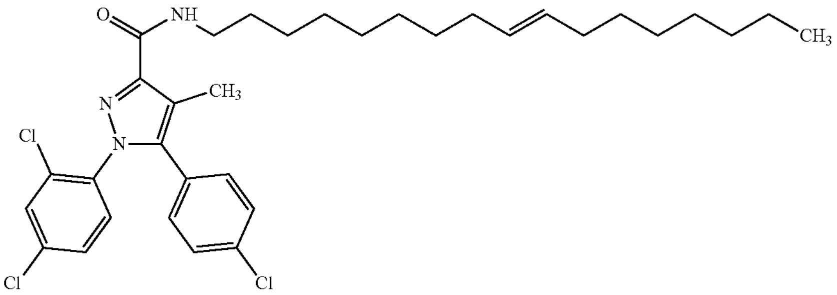
C
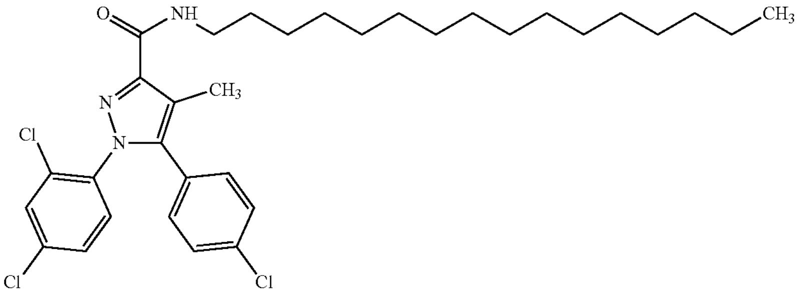
D
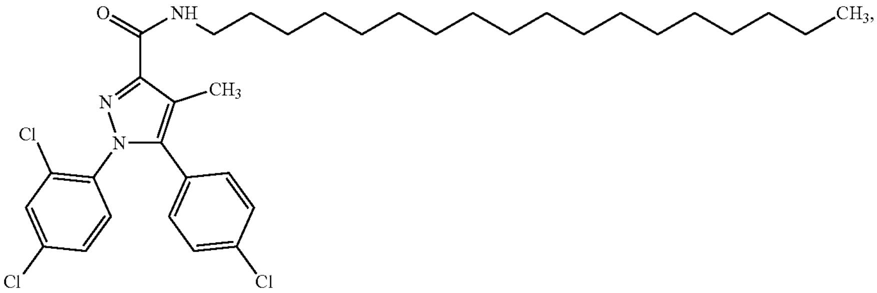
BNS-002
E
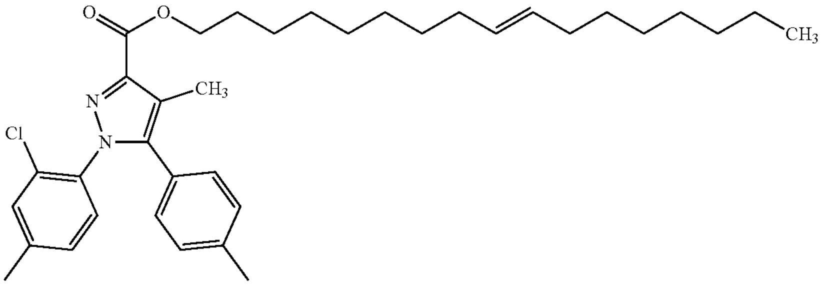

-continued
F
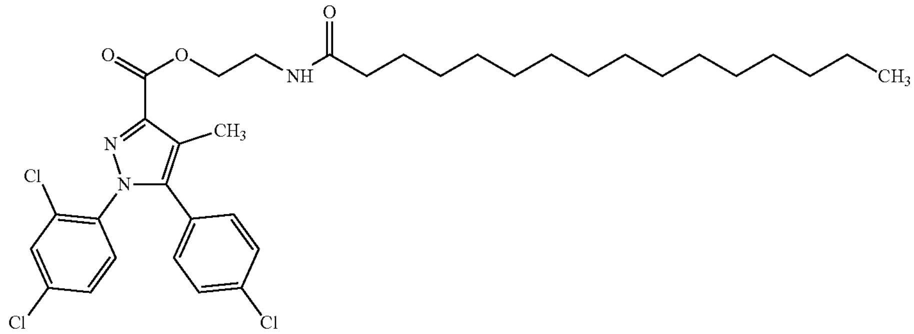
G
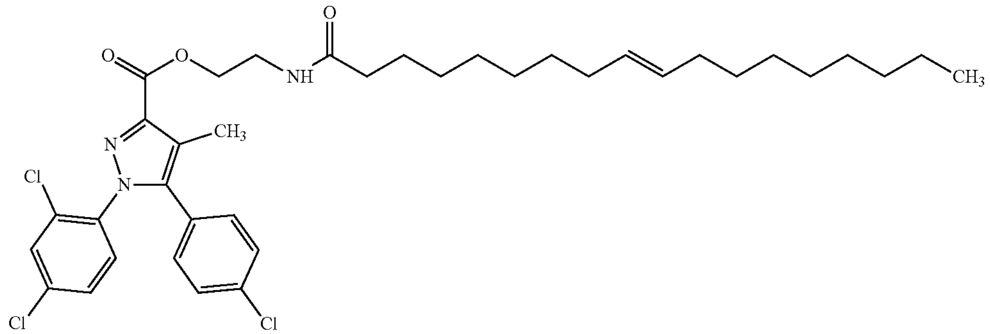
H
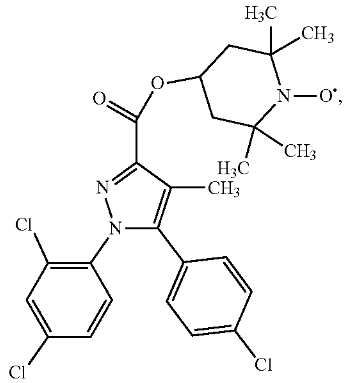
EST
I
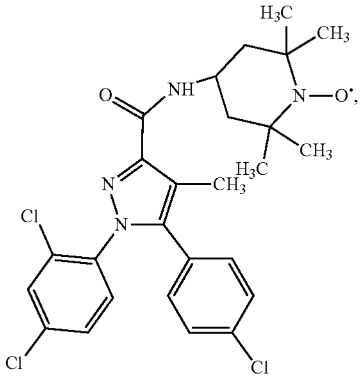
TMP
J
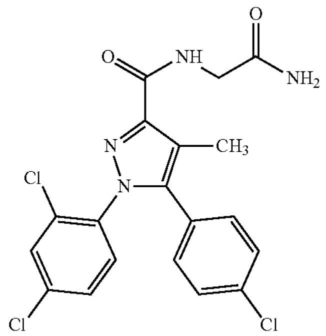
K
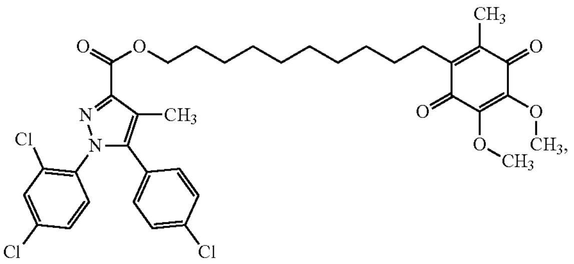
IDB -continued
L
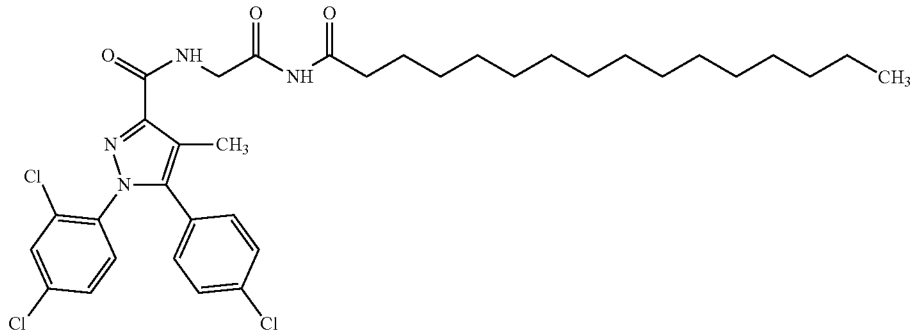
M
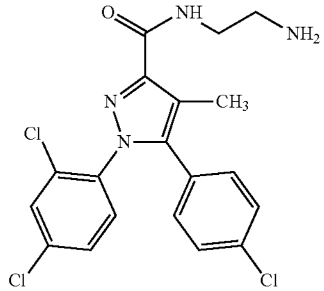
N
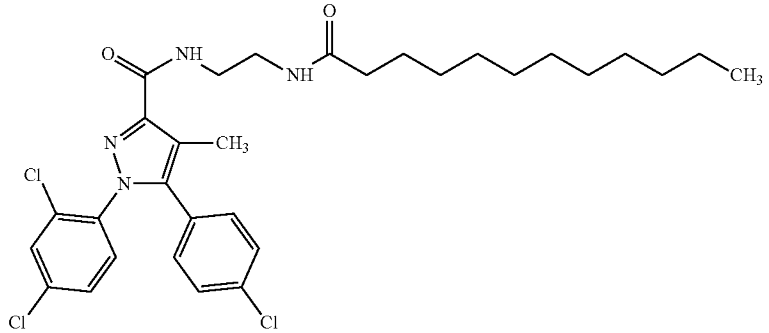
O
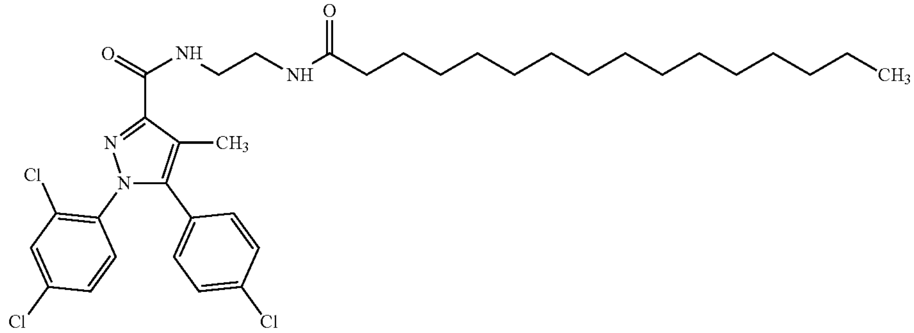
P
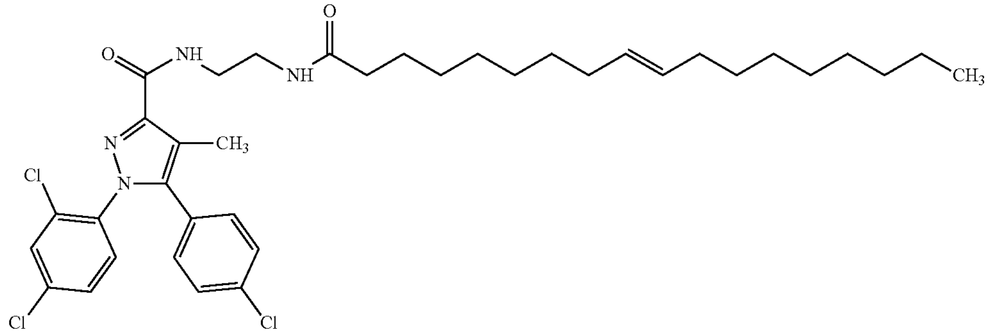

-continued
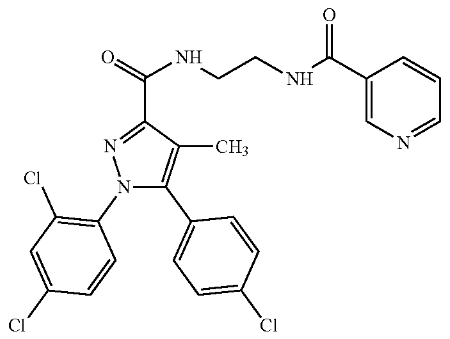
Q
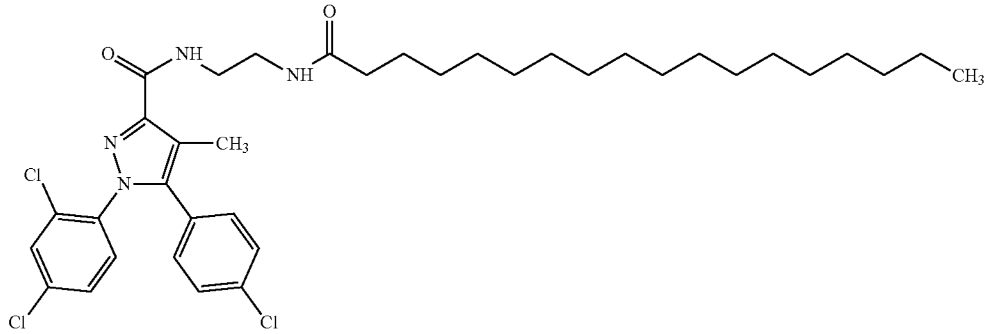
R
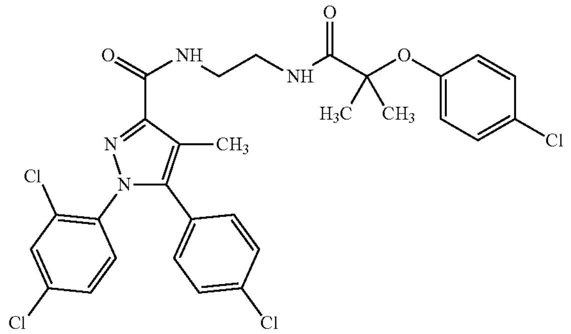
S
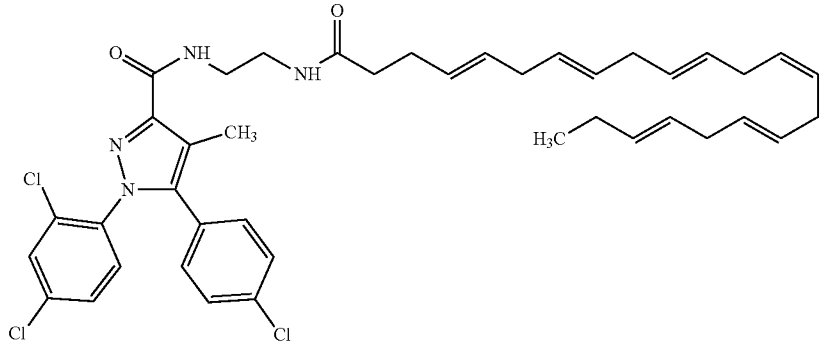
T

-continued
U
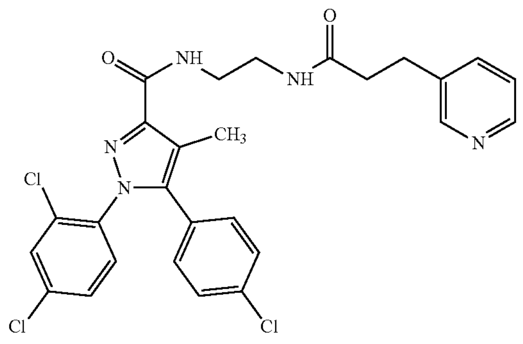
V
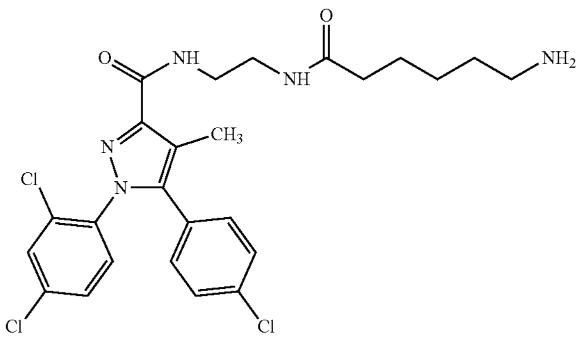
W
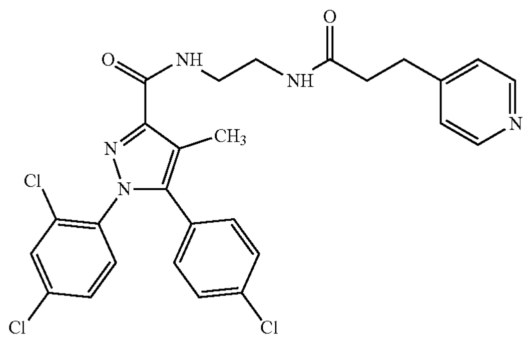
X
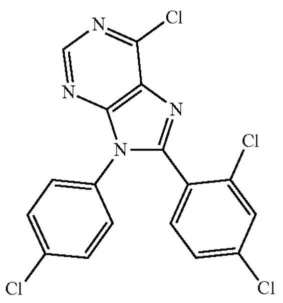
Z
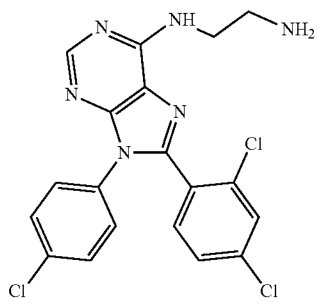
Y
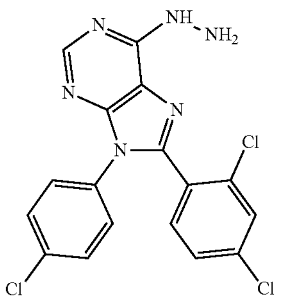
AA
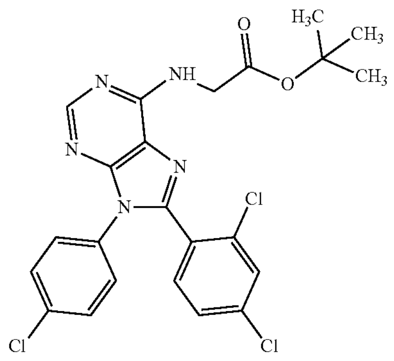
AB
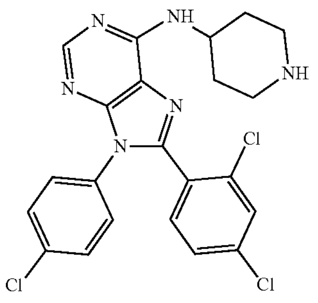

-continued
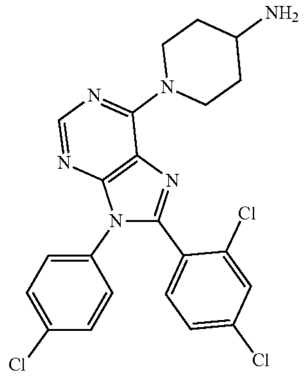
AC
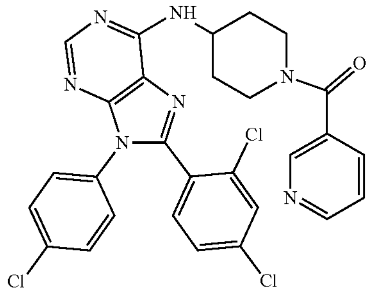
AD
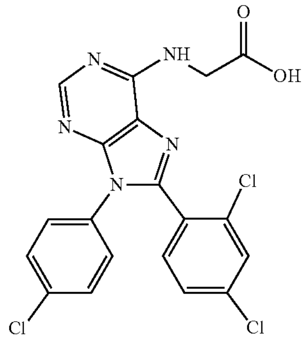
AE
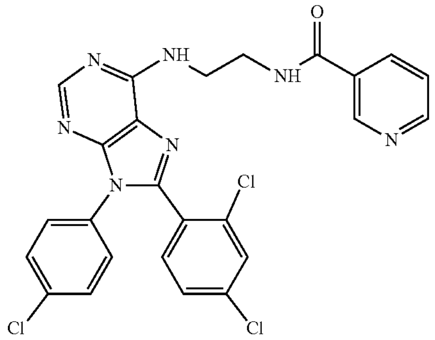
AF
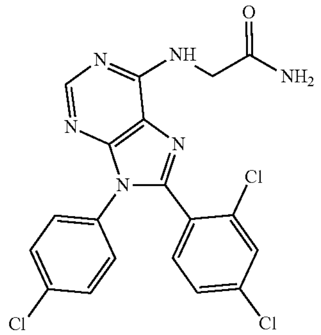
AG
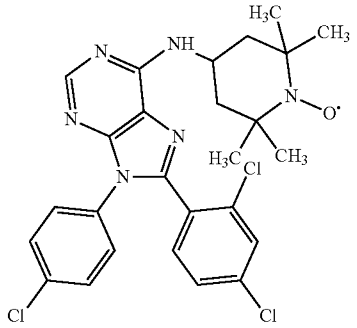
AH
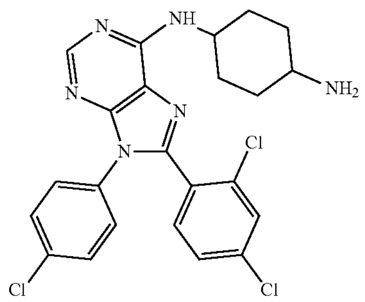
AJ
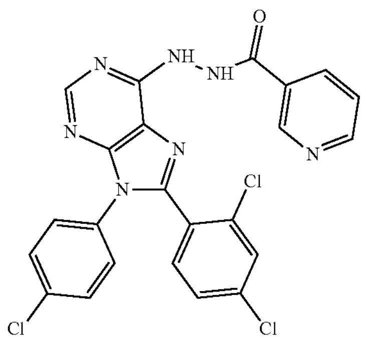
AI -continued
AK
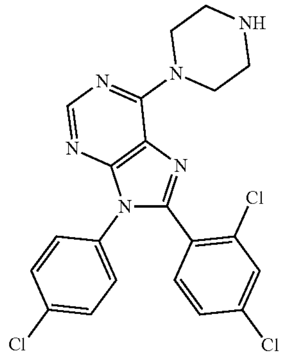
AL
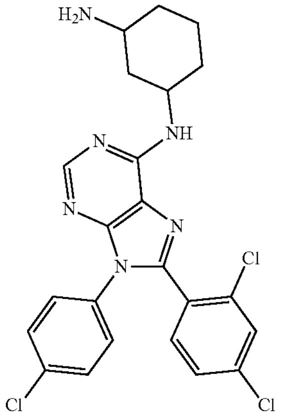
AM
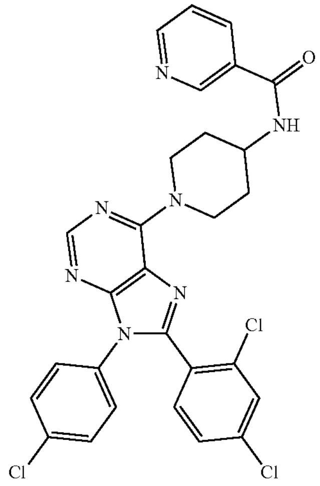
AN
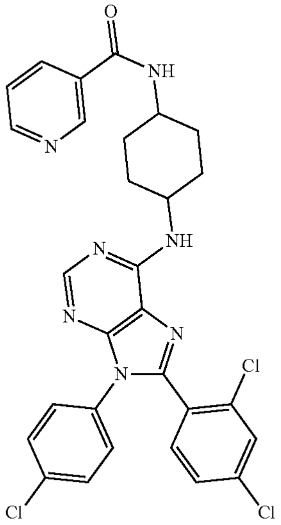
AO
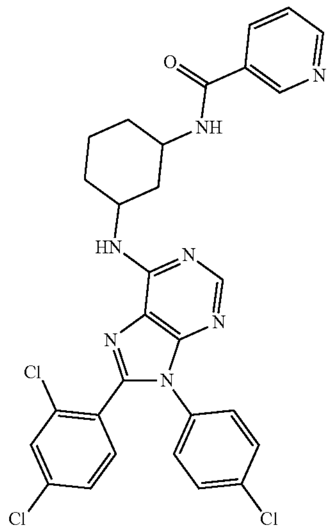
AP
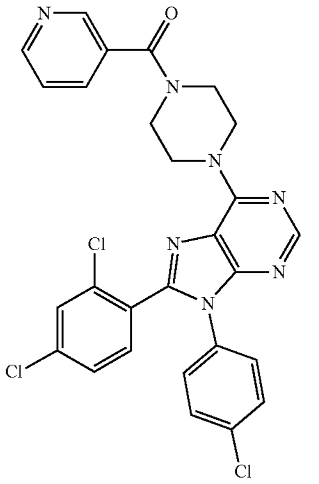

-continued
AQ
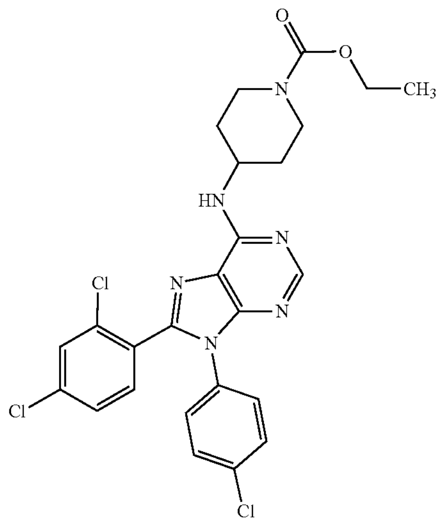
AR
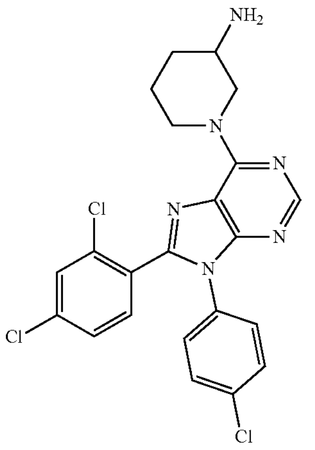
AS
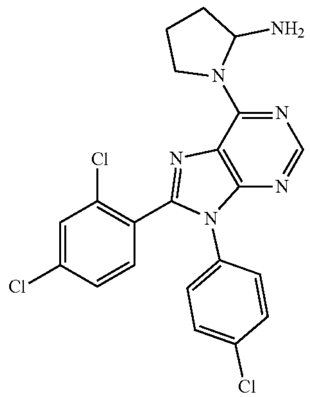
AT
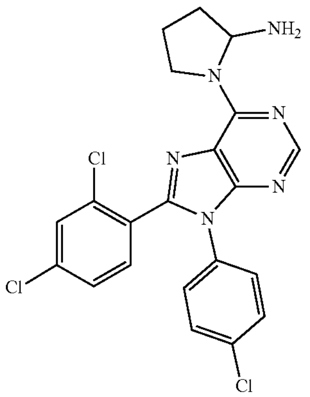
AU
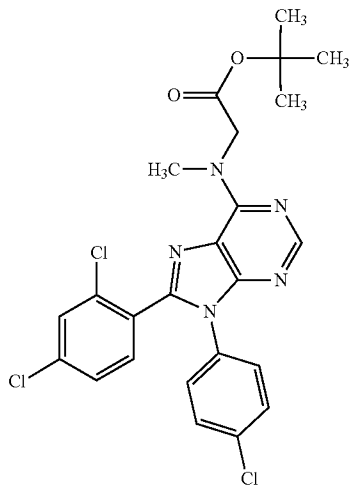
AV
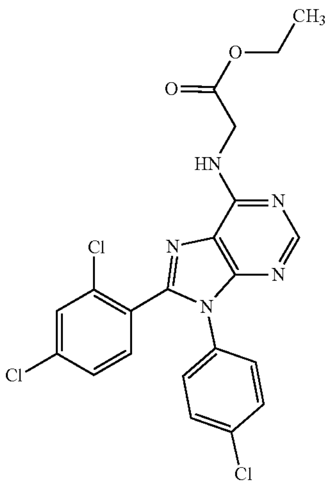

-continued

AX

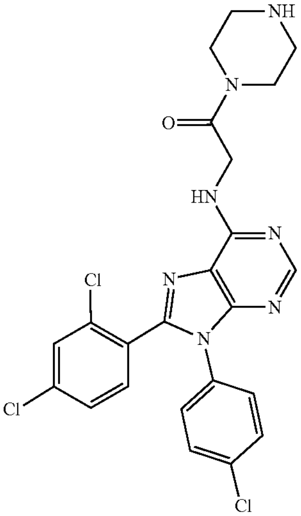

AQ

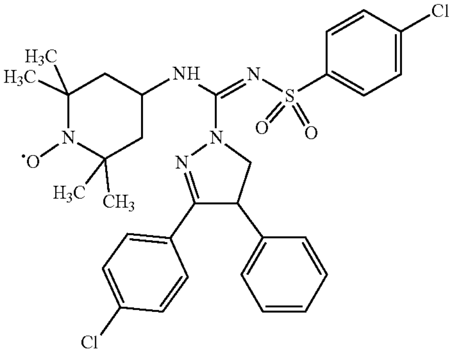

AY

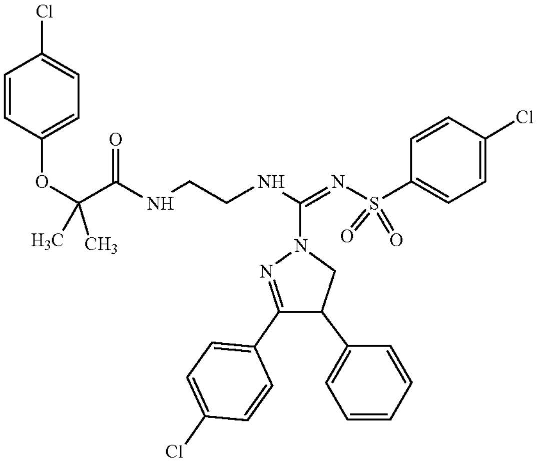

AZ

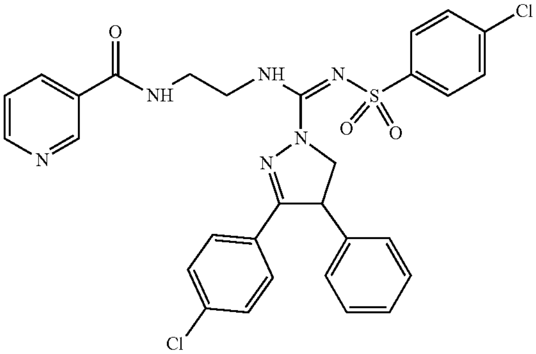

and

BB

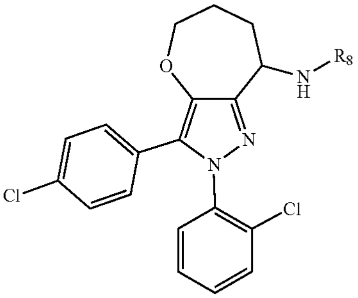

In some embodiments, in each compound of the invention, $R_8$ is a lipophilic moiety.

Compounds of the invention may be used as modulators of peripheral cannabinoid receptors, including peripherally restricted $CB_1$ receptors and $CB_2$ receptors. In some embodiments, the compounds are modulators (e.g., inhibiting) of a peripherally restricted CB1 receptor. In some embodiments, the compounds are neutral antagonists or inverse agonists. In some embodiments, the compounds are modulators (e.g., activating) of $CB_2$ receptors.

As used herein, the expression "peripherally restricted $CB_1$ receptor blocker" refers to agents/materials according to the invention that are antagonists or blockers of $CB_1$ receptors present in peripheral organs and tissues, including the adipose tissues, the liver, skeletal muscles, pancreatic β-cells and the kidneys, without causing centrally-mediated side effects. In other words, these blockers or antagonists retain the therapeutic benefits of globally acting $CB_1$ receptor blockers without causing CNS-mediated side effect.

A "$CB_1$ receptor blocker" or antagonist is a compound according to the invention, which in most general terms partially or fully blocks, inhibits, or neutralizes a biological function of a peripheral $CB_1$ receptor. By partially or fully blocking, inhibiting, or neutralizing a biological function of the receptor, prevention or treatment of a variety of metabolic syndromes can be achieved. These metabolic syndromes include obesity, insulin resistance, diabetes, coronary heart disease, fatty liver, hepatic cirrhosis, chronic kidney disease and cancer.

The invention further provides a compound of formula (I) as a peripherally restricted $CB_1$ receptor inverse agonist.

The invention further provide a composition comprising a compound of the invention. In some embodiments, the composition is a pharmaceutical composition in a form suitable for administration to a human or animal subject. As used herein, the "pharmaceutical composition" comprises a therapeutically effective amount of a compound of the invention, optionally together with suitable additives such as diluents, preservatives, solubilizers, emulsifiers, adjuvant and/or carriers. The compositions may be liquids or lyophilized or otherwise dried formulations and include diluents of various buffer content (e.g.; Tris-HCL, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), and others.

Compositions suitable for oral administration can comprise of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions or self-emulsifying formulations. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers. Tablet forms can include one or more of lactose, sucrose, mannitol, corn starch, potato starch, alginic acid, microcrystalline cellulose, acacia, gelatin, guar gum, colloidal silicon dioxide, croscarmellose sodium talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Compositions suitable for parenteral administration include sterile nanoemulsions, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives.

Compounds of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid.

Compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, $4^{th}$ ed., pages 622-630 (1986).

In some embodiments, the composition is suitable for oral administration.

In other embodiments, the composition is suitable for IV (intravenous) or IM (intramuscular) administration.

In some embodiments, the composition is a self-emulsifying oil formulation comprising nanocarriers according to the invention.

In another one of its aspects, the invention provides a nanocarrier comprising at least one compound according to the invention.

The nanocarrier may be a nanoparticle, a nanocapsule or mixtures thereof. A "nanocarrier" of the invention is a particulate material that is biocompatible and sufficiently resistant to chemical and/or physical destruction, such that a sufficient amount of the nanocarriers remain substantially intact after administration into the human or animal body and for sufficient time to be able to reach the desired target tissue (or organ). Generally, the nanocarriers are of average diameters of up to 700 nm.

Depending on various parameters associated with a compound of the invention (e.g. solubility, molecular weight, polarity, electrical charge, reactivity, chemical stability, biological activity, and others), the compound may be contained (encapsulated) in nanocapsules (NCs), and/or embedded in a matrix making-up nanoparticle (NPs). For the chosen application, the nanocarrier may therefore be in the form of core/shell (termed hereinafter also as nanocapsule), having a polymeric shell and a core containing at least one compound of the invention.

Alternatively, the nanoparticles may be of a substantially uniform composition not featuring a distinct core/shell structure. These nanocarriers are herein referred to as nanoparticles (NPs).

In some embodiments, the average diameter of the nanocarrier is between about 100 and 200 nm. In some embodiments, the average diameter is between about 200 and 300 nm. In some embodiments, the average diameter is between about 300 and 400 nm, the average diameters between 400 and 500 nm. In some embodiments, the average diameter is between about 600 and 700 nm.

In some other embodiments, the average diameter of the nanocarrier is between about 50 and 700 nm. In other embodiments, the average diameter is between about 50 and 500 nm. In other embodiments, the average diameter is between about 50 and 400 nm. In further embodiments, the average diameter is between about 50 and 300 nm. In further embodiments, the average diameter is between about 50 and 200 nm. In further embodiments, the average diameter is between about 50 and 100 nm.

Materials suitable for forming nanocarriers, e.g., nanocapsules and/or nanoparticles according to the invention, are polyesters including polylactic acid (PLA), polyglycolic acid (PGA), polyhydroxybutyrate and polycaprolactone), poly(orthoesters), polyanhydrides, polyamino acid, poly(alkyl cyanoacrylates), polyphophazenes, copolymers of (PLA/PGA) and asparate or polyethylene-oxide (PEO).

In some embodiments, the nanocarrier is a nanoparticle, the nanoparticle comprising a first matrix, wherein a compound of the invention is embedded within the matrix. In other embodiments, the nanocarrier is a nanocapsule, the nanocapsule comprising a first shell encapsulating the compound of the invention or a composition comprising the compound.

The nanocarriers may be further enveloped by another encapsulation layer, thereby forming a double-layered protection. Thus, in some embodiments, the nanocarrier is further encapsulated within a second shell layer, which may comprise the same or different material than that of the first shell layer. In some embodiments, the nanocarrier is further embedded within a second matrix, the first and second matrices may be comprised of the same or different materials.

In order to increase the amount of active compound reaching the target tissue or organ, it is sometimes desired to provide a product comprising a plurality of nanocarriers packed in a single encasing. Therefore, in another aspect, there is provided a nano- or a microcapsule comprising a plurality of nanocarriers of the invention.

According to another aspect, there is provided a nano- or microparticle comprising a plurality of nanocarriers of the invention. Such nano- or microparticles may endow long-acting dosage forms when administered parenterally, or may be used as powders for oral, inhalation or pulmonary delivery of compounds of the invention. In some embodiments, the nano- or microparticle, that comprises a plurality of nanocarriers of the invention, may be formed of a hydrophobic polymer.

Compounds of formula (I) as well as formulations or compositions comprising them may also be used in methods of preventing or treating metabolic syndromes. Accordingly, the invention further provides uses of compounds of the invention in methods of therapeutic prevention or treatment of diseases and disorders associated with $CB_1$ receptor activity, e.g., metabolic syndromes, as defined herein.

The invention further provides methods of prevention and treatment of metabolic diseases and disorders that comprise administering to a human or animal subject an amount of a compound of the invention. The compound may be:

- a highly lipophilic derivative of cannabinoid having a Log P (partition coefficient between n-octanol and water) value ranging from 3 and 17;
- a compound of the general formula (I) and any derived formula, as defined herein.

As noted hereinabove, the metabolic diseases or disorders or syndromes may be selected from obesity, insulin resistance, diabetes, coronary heart disease, liver cirrhosis and cancer.

Thus, the invention provides a method of treating a subject to reduce body fat, or to reduce body weight, or to treat insulin resistance, or to treat diabetes, or to reduce or control high blood pressure, or to improve a poor lipid profile with elevated LDL cholesterol, low HDL cholesterol, and elevated triglycerides, or to treat fatty liver disease, or to ameliorate chronic kidney disease, or to treat a metabolic syndrome as herein defined, the method comprising administering to the subject a compound of the invention. The compound may be in a form suitable for oral, parenteral, subcutaneous, intravenous, intramuscular or interperitoneal administration.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3A-E).

DETAILED DESCRIPTION OF EMBODIMENTS

Figure 1A:
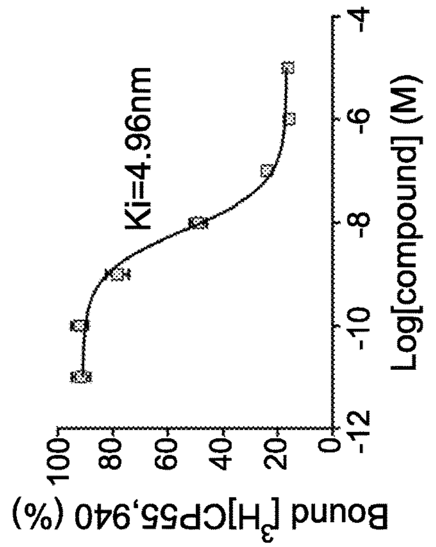
FIGS. 1A-C depict the results of radioligand displacement assays. BNS-002 is more lipid soluble than rimonabant (estimated partition coefficient [log P], 17 vs. 6.4 for rimonabant) but retains high affinity and selectivity for $CB_1$ receptor. In radioligand displacement assays, BNS-002 has a Ki of 4.96 nM for $CB_1$ receptor, which is similar to that of rimonabant (FIG. 1A). Like rimonabant, BNS-002 reduces GTPγS binding in mouse brain membranes (FIG. 1B) and is able to ameliorate the action of the potent $CB_1$ receptor agonist HU-210 (FIG. 1C), suggesting that it is an inverse agonist.

As disclosed herein, "EST" is herein identified compound "I". "TMP" is herein identified compound "H". "IDB" is herein identified compound "K". "BNS-002" is herein identified compound "D".

Synthesis and characterization of 5-(4-chlorophenyl)-1-(2,4-dichlorophenyl)-4-methyl-N-octadecyl-1H-pyrazole-3-carboxamide (BNS-002)

Synthesis procedure. A solution of Ethyl chloroformate (0.25 mL, 2.6 mmol) in dichloromethane (10 mL) were added to a 5-(4-chlorophenyl)-1-(2,4-dichlorophenyl)-4-methyl-1H-pyrazole-3-carboxylic acid (1 g, 2.6 mmol) in dry THF (150 mL). The mixture was added to a solution of stearylamine (0.7 g, 2.6 mmol) and triethylamine (0.38 ml, 2.8 mmol) in dry THF (200 mL). The addition performed slowly and in drop-wise at room temperature, rate 10 ml/min. The reaction mixture was stirred at room temperature over 4 hours. A pale-yellow solution and a white precipitate were formed. The mixture was filtered on white paper filter and washed with dry THF (50 ml). Following filtration, the THF was evaporated, and the crude was dissolved in hexane (150 ml), poured into separatory funnel, washed with DDW (100 ml) three times. The hexane layer was collected and dried over anhydrous sodium sulfate, filtered through white paper filter, and removed via evaporation forming a pale-yellow liquid. A 70% yield before column chromatography was obtained. The precipitate was dissolved again in 10 ml of dichloromethane and incorporated with silica powder (silica gel 60), dried and load to pre-prepared silica column (radius 5 cm, length 25 cm). The separation and the purification were completed as follows: 2 fold volumes of column capacity were washed with hexane; followed by 2 volumes of column capacity with hexane.

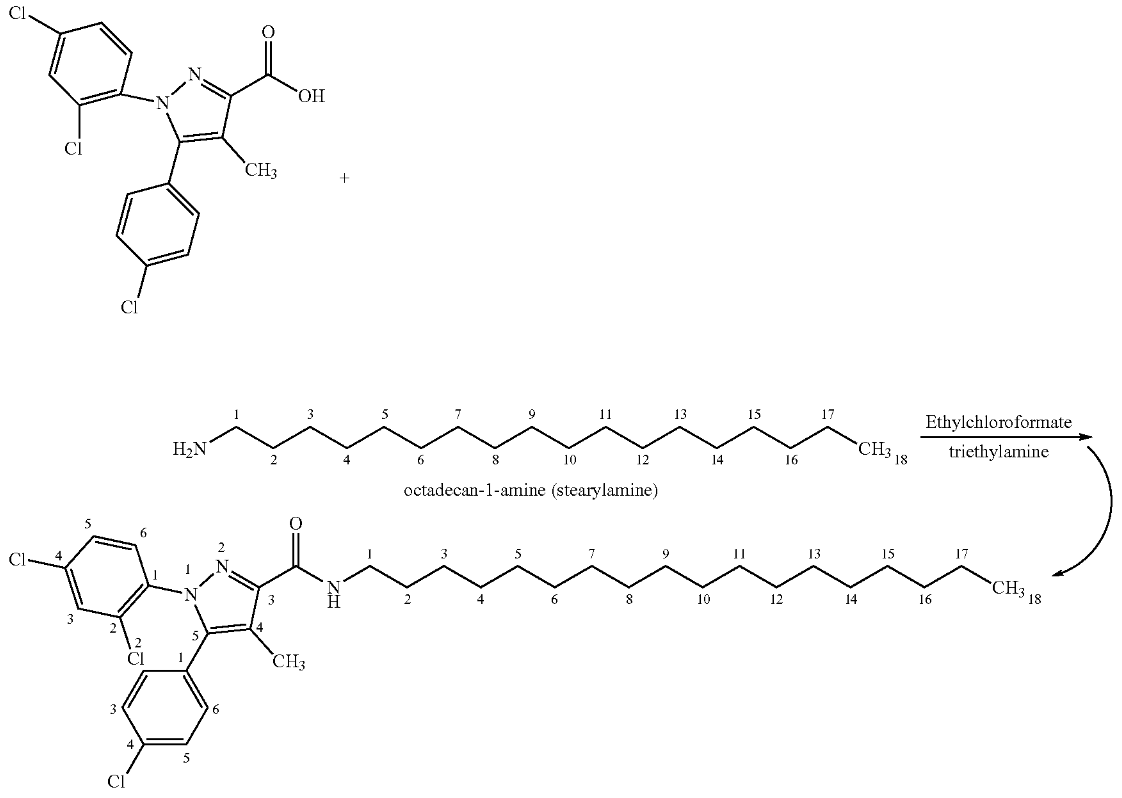

5-(4-chlorophenyl)-1-(2,4-dichlorophenyl)-4-methyl-N-octadecyl-1H-pyrazole-3-carboxamide (BNS-002)

Characterization. The LC-MS and the H-NMR spectrum confirmed the structure of the title compound. The HPLC shows purity above 98%.

Compounds having longer or shorter alkyl chains may be similarly prepared. Non-limiting examples of such compounds include:

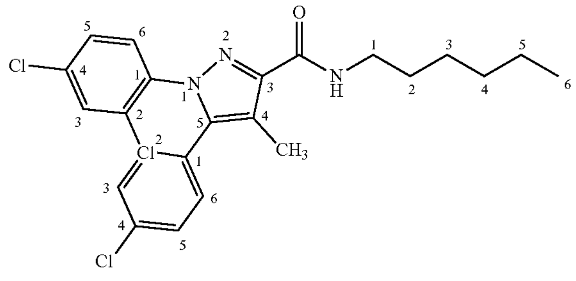

5-(4-chlorophenyl)-1-(2,4-dichlorophenyl)-N-hexyl-4-methyl-1H-pyrazole-3-carboxamide

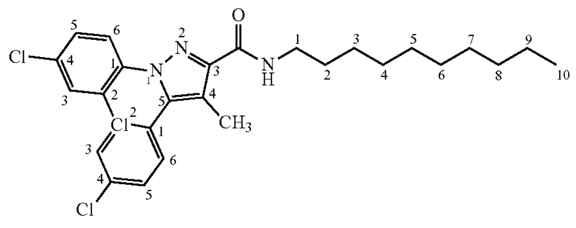

5-(4-chlorophenyl)-N-decyl-1-(2,4-dichlorophenyl)-4-methyl-1H-pyrazole-3-carboxamide

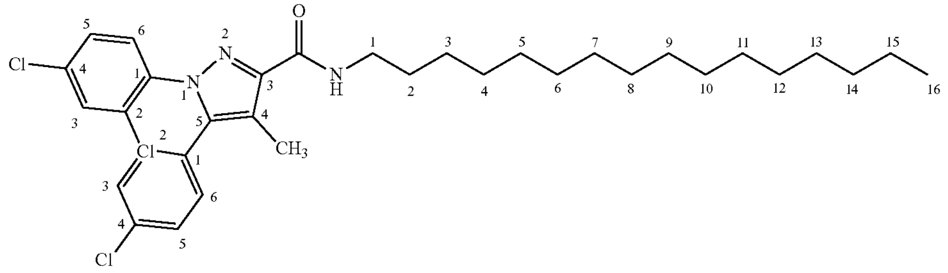

5-(4-chlorophenyl)-1-(2,4-dichlorophenyl)-N-hexadecyl-4-methyl-1H-pyrazole-3-carboxamide

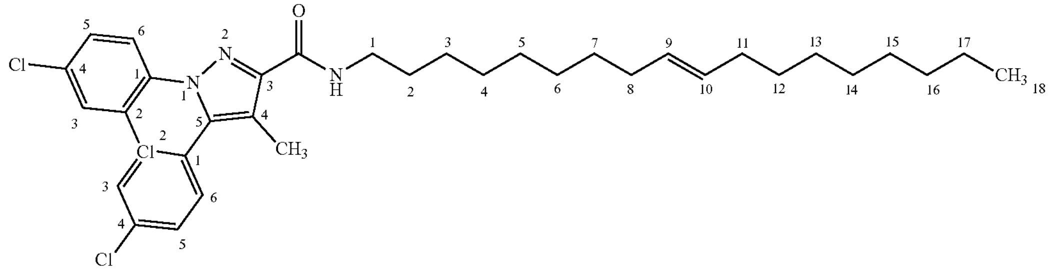

(E)-5-(4-chlorophenyl)-1-(2,4-dichlorophenyl)-4-methyl-N-(octadec-9-en-1-yl)-1H-pyrazole-3-carboxamide Radioligand binding assays. BNS-002 binding to $CB_1$ receptor was assessed in competition displacement assays using [$^3$H]CP-55,940 as the radioligand and crude membranes from mouse brain for $CB_1$ receptor. All data were in triplicates with Ki values determined from three independent experiments.

[$^{35}$S]GTPγS binding. Mouse brains were dissected and P2 membranes prepared and resuspended at ~6 μg protein/μL in 1 ml assay buffer (50 mM Tris HCl, 9 mM MgCl2, 0.2 mM EGTA, 150 mM NaCl; pH 7.4). Ligand-stimulated [$^{35}$S]GTPγS binding was assayed as described previously (Tam et at, JCI 2010). Briefly, membranes (10 μg protein) were incubated in assay buffer containing 100 μM GDP, 0.05 nM [$^{35}$S]GTPγS, test compounds at 1 nM-1 μM, and 1.4 mg/mL fatty acid-free BSA in siliconized glass tubes. Bound ligand was separated from free by vacuum filtration. Non-specific binding was determined using 10 μM GTPS. Basal binding was assayed in the absence of the ligand and in the presence of GDP.

Tissue levels of antagonists. Mice received a single dose (3 or 10 mg/kg ip) of BNS-002 or rimonabant and were sacrificed 1 hour later. Blood was collected, and the mice were perfused with phosphate buffered saline for 1 min to remove drug from the intravascular space before removing the brain and liver. Drug levels in tissue homogenates and plasma were determined by using LC-MS/MS.

Locomotor activity. Locomotor activity was quantified by the number of disruptions of infrared XYZ beam arrays with a beam spacing of 0.25 cm in the Promethion High-Definition Behavioral Phenotyping System (Sable Instruments, Inc., Las Vegas, NV, USA).

Mice. The experimental protocol used was approved by the Institutional Animal Care and Use Committee of the Hebrew University, which is an AAALAC International accredited institute. Male 6 week old C57Bl/6J mice were obtained from Harlan Laboratories. Mice were maintained under a 12-h light/dark cycle and fed ad libitum. To generate diet-induced obesity, C57Bl6/J mice were fed either a high-fat diet (HFD) (60% of calories from fat, 20% from protein, and 20% from carbohydrates; Research Diet, D12492) or a standard laboratory diet (STD, 14% fat, 24% protein, 62% carbohydrates; NIH-31 rodent diet) for 14 weeks.

HFD-fed obese mice received vehicle (1% Tween80, 4% DMSO, 95% Saline), BNS-002, IDB or rimonabant daily for 7-28 days by intraperitoneal (ip) injections of 10, 15, 20, and 30 mg/kg as indicated in the figures. Age-matched control mice on STD received vehicle daily. Body weight and food intake were monitored daily. Total body fat and lean masses were determined by EchoMRI-100H™ (Echo Medical Systems LLC, Houston, TX, USA). 24 h urine was collected one week before euthanasia using mouse metabolic cages (CCS2000 Chiller System, Hatteras Instruments, NC, USA). At weeks 20 mice were euthanized by a cervical dislocation under anesthesia, the kidneys, brain, liver, fat pads, and muscles were removed and weighed, and samples were either snap-frozen or fixed in buffered 4% formalin Trunk blood was collected for determining the biochemical parameters.

Multi-parameter metabolic assessment. Metabolic profile of the mice was assessed by using the Promethion High-Definition Behavioral Phenotyping System (Sable Instruments, Inc., Las Vegas, NV, USA). Data acquisition and instrument control were performed using MetaScreen software version 2.2.18.0, and the obtained raw data were processed using ExpeData version 1.8.4 using an analysis script detailing all aspects of data transformation. Mice with free access to food and water were subjected to a standard 12 h light/12 h dark cycle, which consisted of a 48 h acclimation period followed by 24 h of sampling. Respiratory gases were measured by using the GA-3 gas analyzer (Sable Systems, Inc., Las Vegas, NV, USA) using a pull-mode, negative-pressure system. Air flow was measured and controlled by FR-8 (Sable Systems, Inc., Las Vegas, NV, USA), with a set flow rate of 2000 mL/min. Water vapor was continuously measured and its dilution effect on $O_2$ and $CO_2$ was mathematically compensated. Effective mass was calculated by [body mass]$^{0.75}$. Fat oxidation (FO) and carbohydrate oxidation (CHO) were calculated as FO=1.69×$VO_2$−1.69×$VCO_2$ and CHO=4.57×$VCO_2$−3.23×$VO_2$ and expressed as g/d/kg$^{eff.Mass}$.

Glucose tolerance (ipGTT) test and insulin sensitivity tests (ipIST). Mice that fasted overnight were injected with glucose (1.5 g/kg, ip), followed by a tail blood collection at 0, 15, 30, 45, 60, 90, and 120 minutes. Blood glucose levels were determined using the Elite glucometer (Bayer, Pittsburgh, PA). On the following day, mice were fasted for 6 h before receiving insulin (0.75 U/kg, i.p.; Eli Lilly, DC, USA or Actrapid® vial, novo nordisk A/S, Denmark), and blood glucose levels were determined at the same intervals as above.

Blood and urine biochemistry. Serum and urine levels of creatinine as well as serum levels of ALT, AST, ALP, HDL, LDL, TG and cholesterol were determined by using the Cobas C-111 chemistry analyzer (Roche, Switzerland). Creatinine clearance was calculated using urine and serum creatinine levels (CCr mL/h=Urine creatinine mg/dL×Urine volume/Serum creatinine mg/dL×24 hrs). Serum insulin levels were measured by an ELISA kit (Crystal Chem, Inc., Downers Grove, IL, USA). Fasting blood glucose was measured using the Elite glucometer (Bayer, Pittsburgh, PA).

Histopathological Analyses. 5 μm paraffin-embedded liver sections from 5 animals per group were stained with hematoxylin-eosin staining. Liver images were captured with a Zeiss AxioCam ICc5 color camera mounted on a Zeiss Axio Scope.A1 light microscope and taken from 10 random 40× fields of each animal.

Figure 1B:
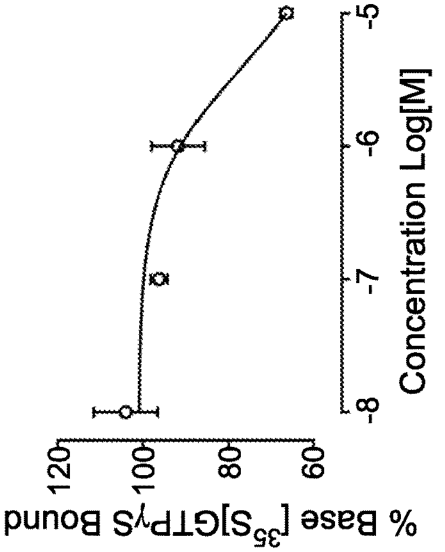
Figure 1C:
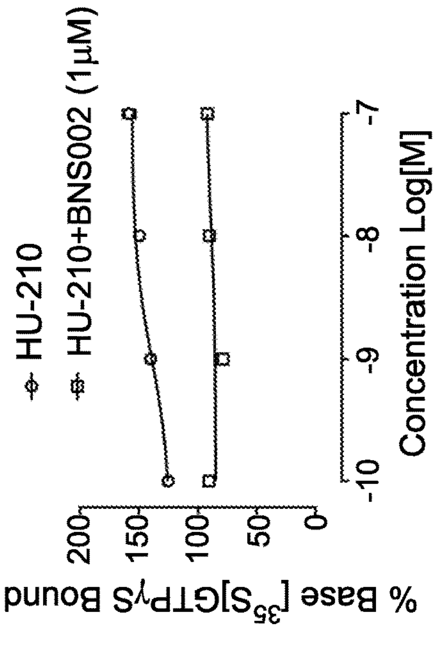

Results:

BNS-002 is more lipid soluble than rimonabant (estimated partition coefficient [log P], 17 vs. 6.4 for rimonabant) but retains high affinity and selectivity for CB1 receptor. In radioligand displacement assays, BNS-002 has a Ki of 4.96 nM for CB1 receptor, which is similar to that of rimonabant (FIG. 1A). Like rimonabant, BNS-002 reduces GTPγS binding in mouse brain membranes (FIG. 1B) and is able to ameliorate the action of the potent CB1 receptor agonist HU-210 (FIG. 1C), suggesting that it is an inverse agonist.

Figure 2A:
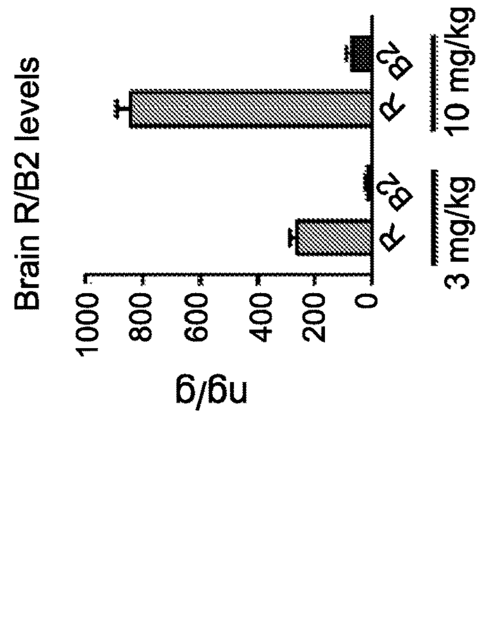
FIGS. 2A-B demosnstare reduced brain penetrance of BSN002. BSN002 displays markedly reduced brain penetrance, as reflected by its reduced brain levels and increased serum levels following an administration of the compound in two different doses (3 and 10 mg/kg, ip).
Figure 2B:
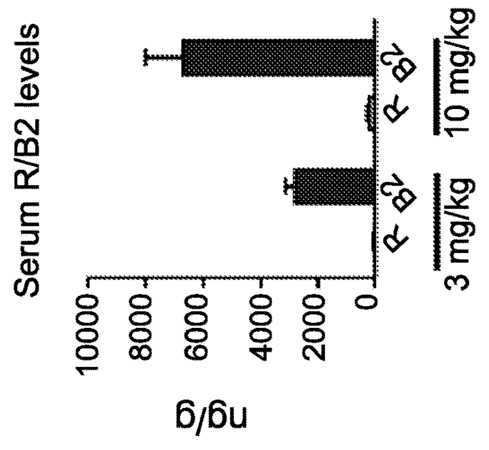
Figures 3A, 3B, 3C:
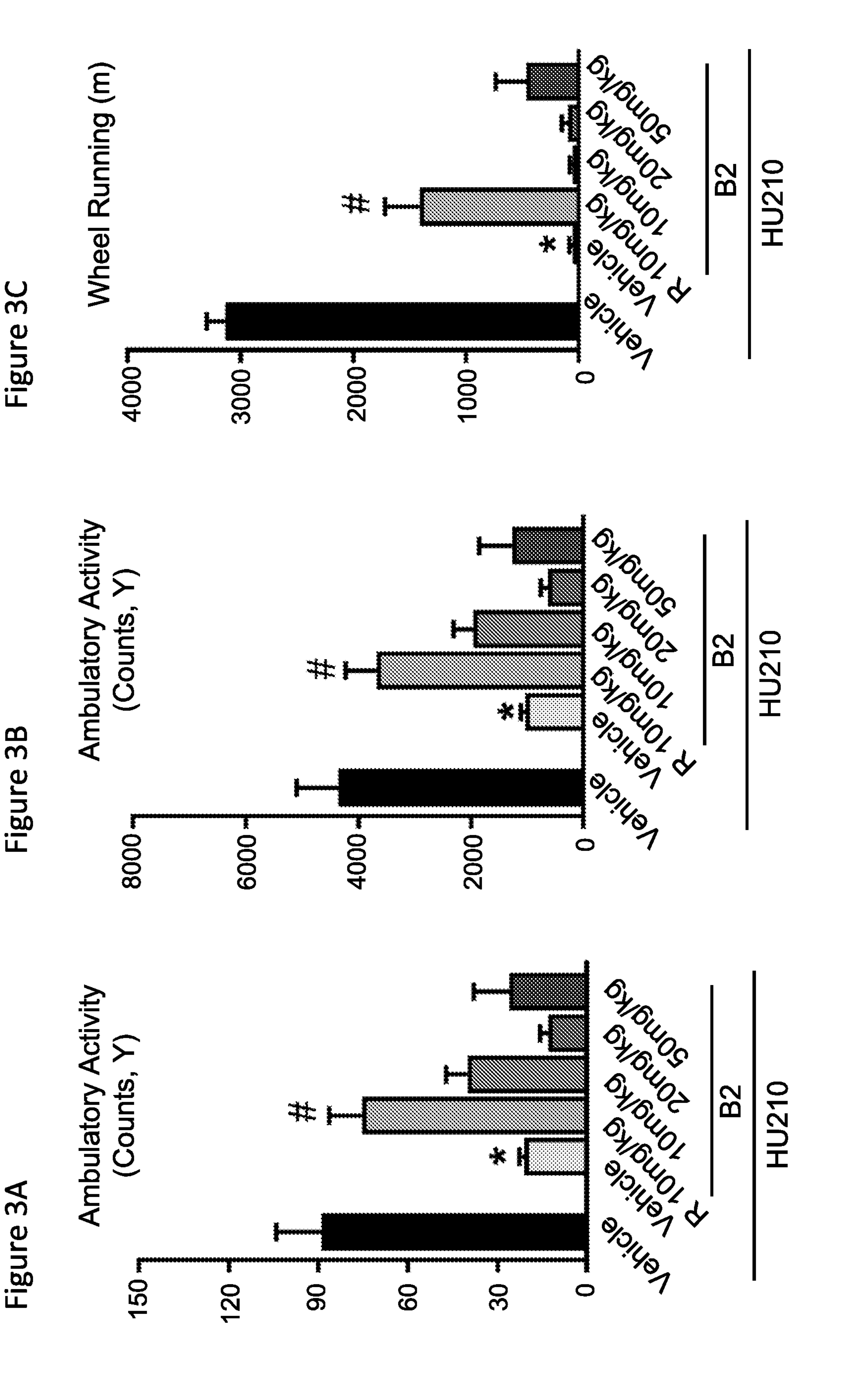
FIGS. 3A-E provide comparison of the effects of BNS002 and rimonabant on ambulation. Whether the reduced brain penetrance of BNS-002 is associated with an attenuation of behavioral effects was tested. To that end, the effects of BNS-002 and rimonabant were evaluated in antagonizing cannabinoid-induced hypomotility. The marked increase in immobility induced in mice by the cannabinoid agonist HU-210 (30 μg/kg, ip) was completely blocked by rimonabant (10 mg/kg, ip) but was unaffected by a similar dose and even higher doses of BNS-002 (10, 20, and 50 mg/kg.
Figure 3D:
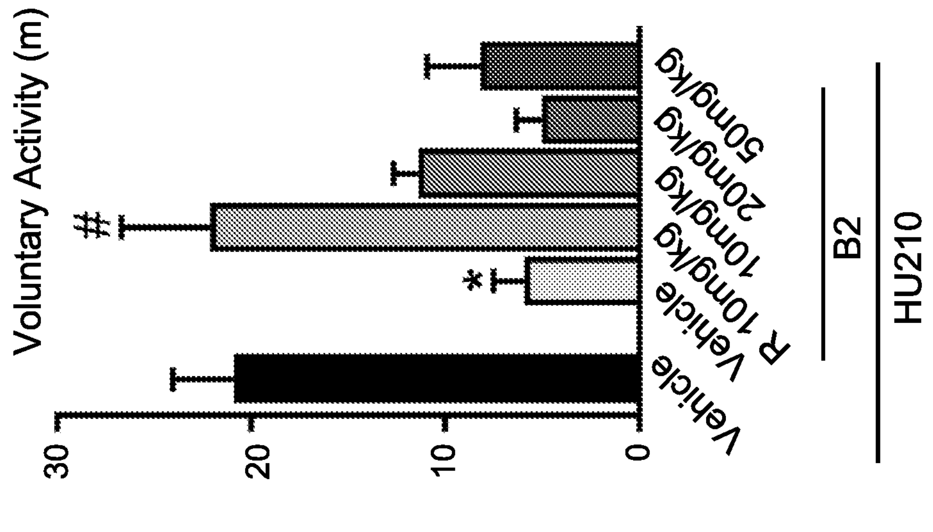
Figure 3E:
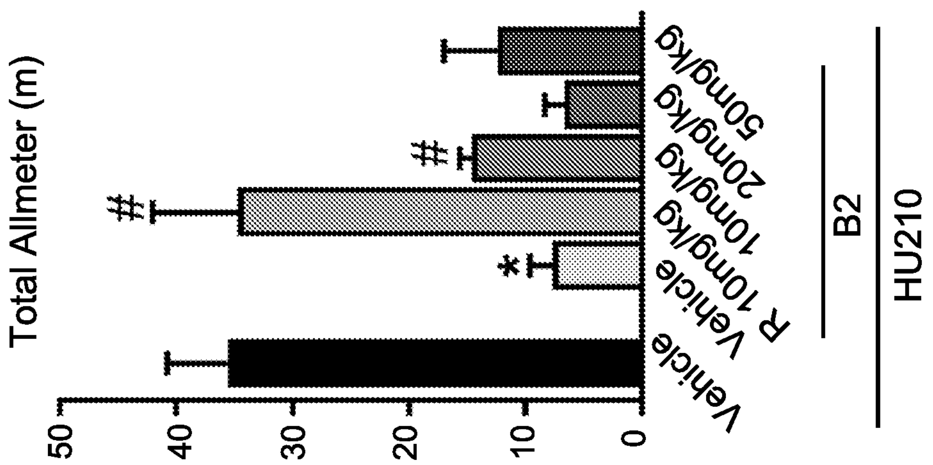
Figure 4A:
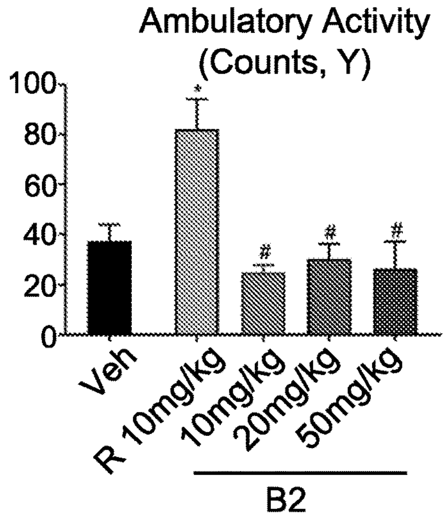
FIGS. 4A-D show the increased activity profile of rimonabant as compared with BNS002. Rimonabant (10 mg/kg, ip), but not BNS-002 (at 10, 20 and 50 mg/kg, ip), induced a marked increase in the activity profile in mice (FIGS. 4A-D).
Figure 4B:
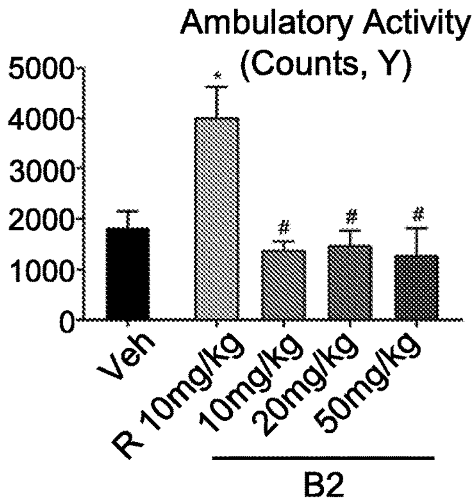
Figure 4C:
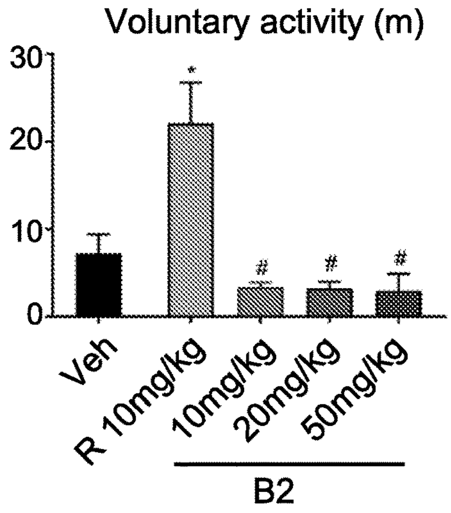
Figure 4D:
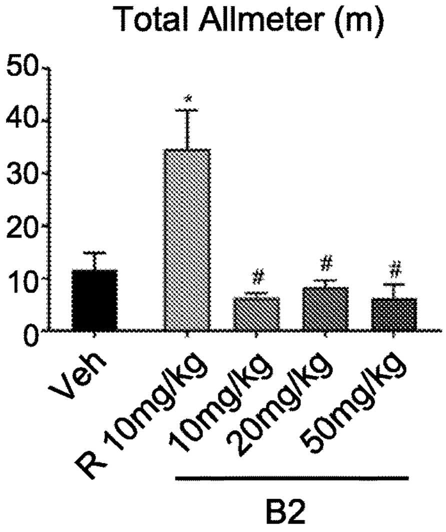

Importantly, BSN002 displays markedly reduced brain penetrance, as reflected by its reduced brain levels and increased serum levels following an administration of the compound in two different doses (3 and 10 mg/kg, ip; FIGS. 2A-B).

Next the inventors tested whether the reduced brain penetrance of BNS-002 is associated with an attenuation of behavioral effects. To that end, we compared the effects of BNS-002 and rimonabant in antagonizing cannabinoid-induced hypomotility. The marked increase in immobility induced in mice by the cannabinoid agonist HU-210 (30 μg/kg, ip) was completely blocked by rimonabant (10 mg/kg, ip) but was unaffected by a similar dose and even higher doses of BNS-002 (10, 20, and 50 mg/kg; FIGS. 3A-E).

In addition, rimonabant (10 mg/kg, ip), but not BNS-002 (at 10, 20 and 50 mg/kg, ip), also induced a marked increase in the activity profile in mice (FIGS. 4A-D).

Figure 5A:
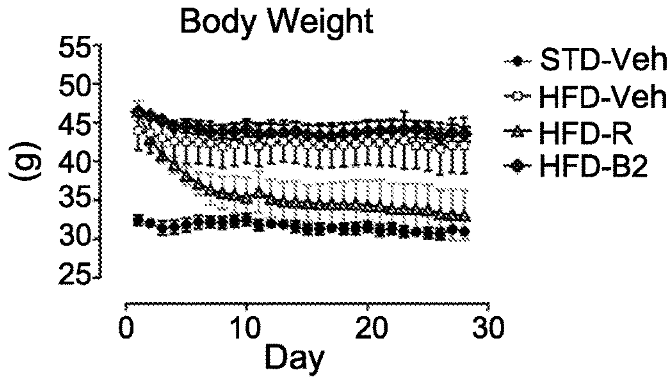
FIGS. 5A-B show the metabolic profile of BNS002 and rimonabant. The metabolic profile of BNS-002 and rimonabant was examined in mice with diet-induced obesity (DIO). Male C57BL/6 mice fed a high-fat diet (HFD) for 14 weeks became obese and were then started on daily ip injections of vehicle, rimonabant, or BNS002 (both at 10 mg/kg/d) for an additional 28 days. Age- and sex-matched mice on standard chow served as controls. The overweight and increased adiposity of mice on HFD were significantly reduced by rimonabant only (FIGS. 5A-B).
Figure 5B:
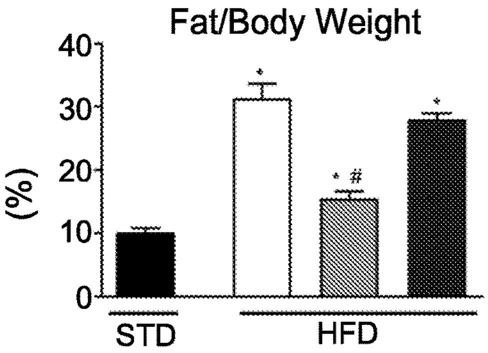

The metabolic profile of BNS-002 and rimonabant was next examined in mice with diet-induced obesity (DIO). Male C57BL/6 mice fed a high-fat diet (HFD) for 14 weeks became obese and were then started on daily ip injections of vehicle, rimonabant, or AM6545 (both at 10 mg/kg/d) for an additional 28 days. Age- and sex-matched mice on standard chow served as controls. The overweight and increased adiposity of mice on HFD were significantly reduced by rimonabant only (FIGS. 5A-B).

Figure 6A:
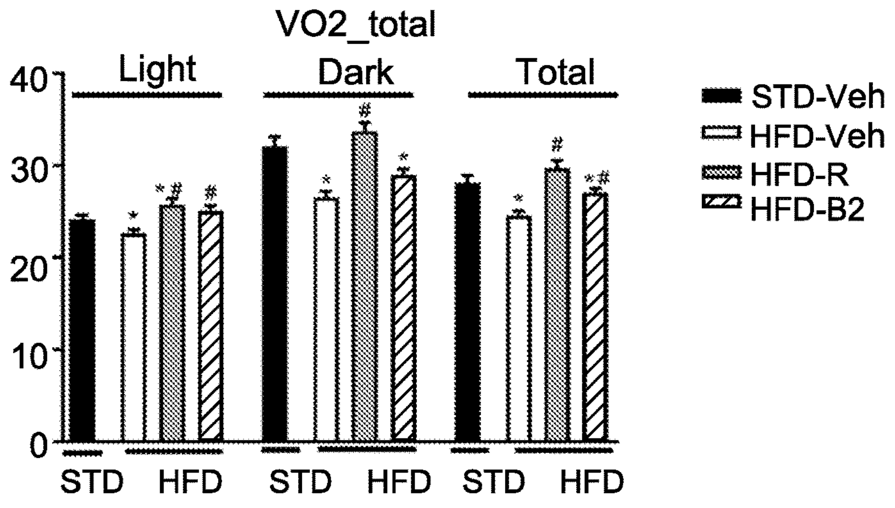
FIGS. 6A-C show that both rimonanbant and BNS002 upregulate HFD-induced reduction in $VO_2$, total energy expenditure, and fat oxidation, as measured by using an indirect calorimetry assessment.
Figure 6B:
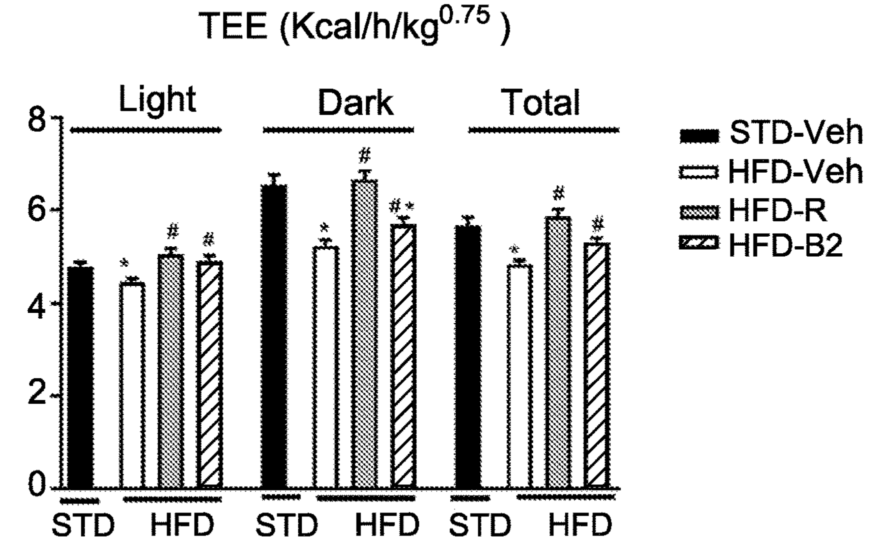
Figure 6C:
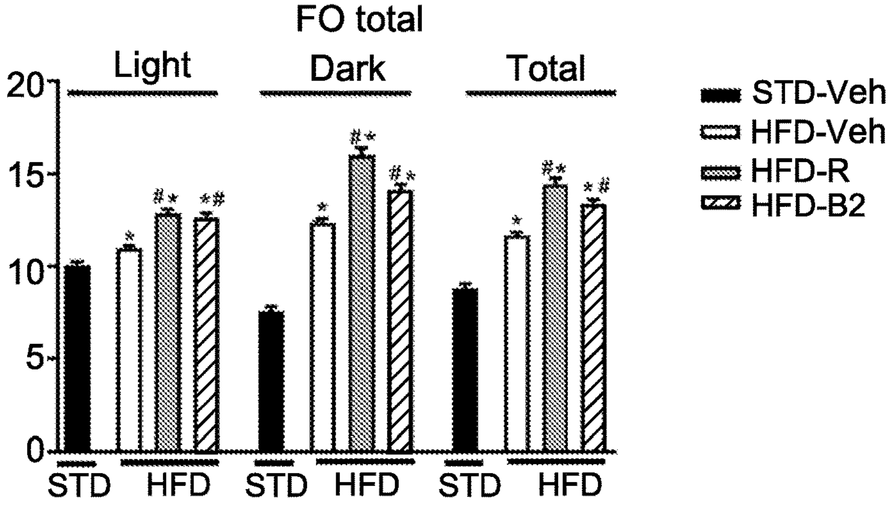

Yet, significant increase in the metabolic profile of the DIO mice treated with both antagonists was demonstrated using an indirect calorimetry assessment. As shown in FIGS. 6A-C, both rimonabant and BNS-002 were able to upregulate the HFD-induced reduction in $VO_2$, total energy expenditure, and fat oxidation.

Figures 7A, 7B, 8A, 8B, 8C:
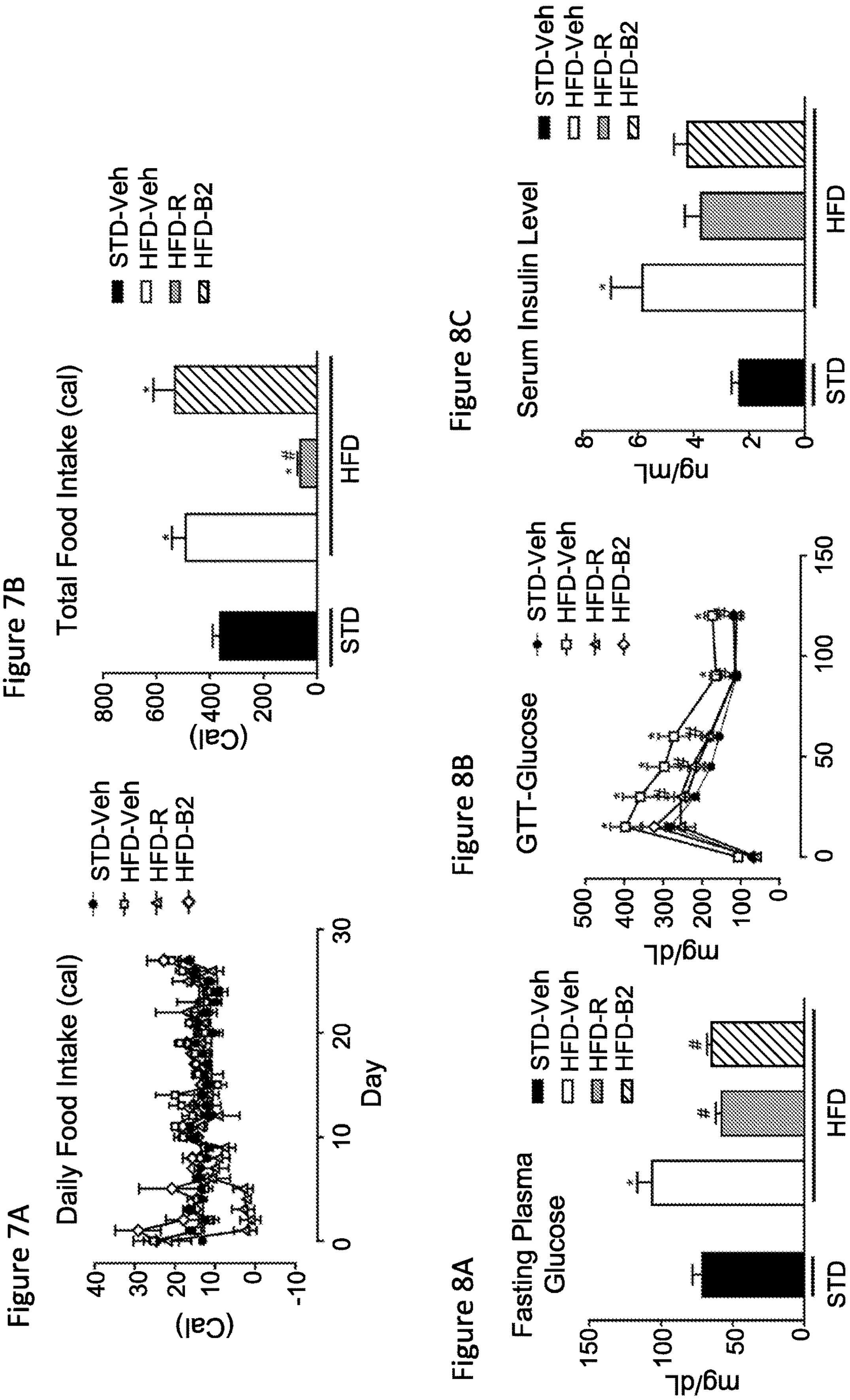
FIGS. 7A-B demonstrate the efficacy of rimonabant over BNS002 in reducing food intake. The greater efficacy of rimonabant over BNS-002 in reducing body weight is probably related to its ability to reduce total caloric intake (FIGS. 7A-B).
FIGS. 8A-C show the efficacy of rimonabant and BNS-002 in ameliorating HFD-induced hyperglycemia and glucose tolerance. HFD-induced hyperglycemia and glucose intolerance were completely reversed by BNS-002 in a similar fashion as rimonabant (FIGS. 8A-B). A trend toward reduction in serum insulin levels was also documented by both compounds (FIG. 8C).

The greater efficacy of rimonabant over BNS-002 in reducing body weight is probably related to its ability to reduce total caloric intake (FIGS. 7A-B).

Nevertheless, HFD-induced hyperglycemia and glucose intolerance were completely reversed by BNS-002 in a similar fashion as rimonabant (FIGS. 8A-B). A trend toward reduction in serum insulin levels was also documented by both compounds (FIG. 8C).

Figure 9:
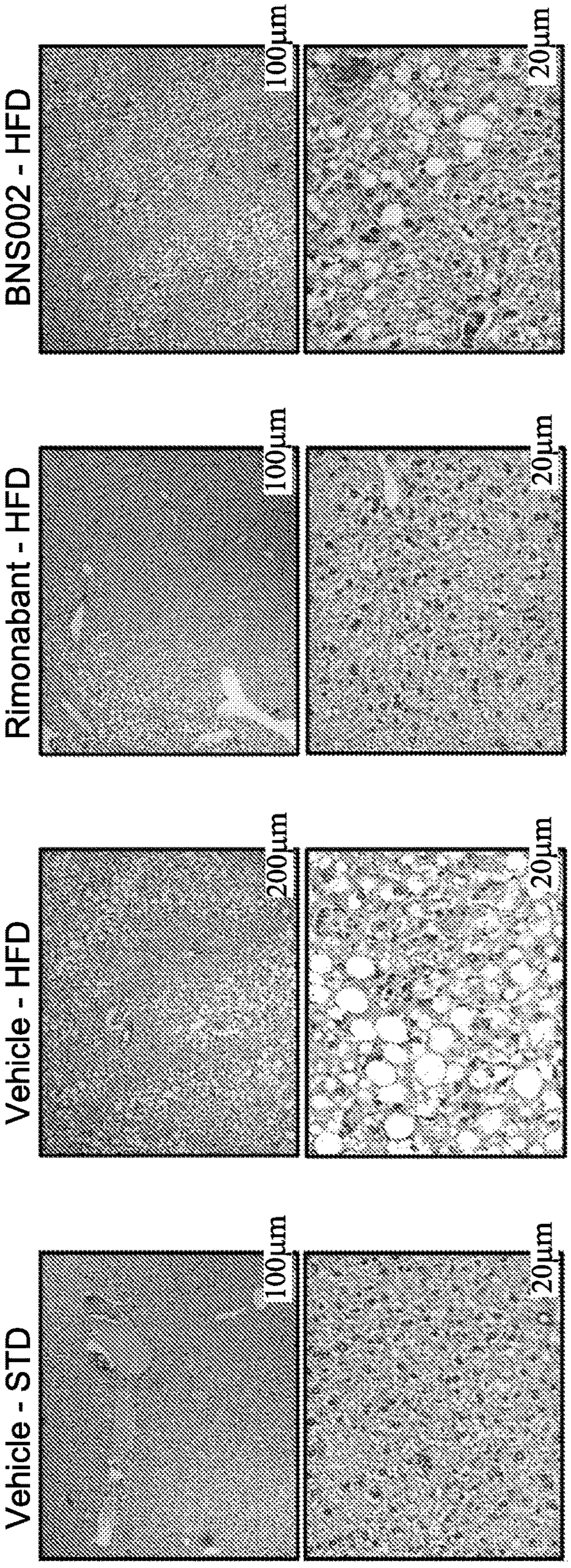
FIG. 9 shows the efficacy of rimonabant and BNS-002 in reversing HFD-induced hepatic steatosis. HFD-induced hepatic steatosis, as reflected in elevated fat vacuoles in the liver, was completely reversed by rimonabant and partially by BNS-002.

Moreover, HFD-induced hepatic steatosis, as reflected in elevated fat vacuoles in the liver, was completely reversed by rimonabant and partially by BNS-002 (FIG. 9).

In addition, HFD-induced kidney hyperfiltration was completely normalized by BNS-002 (FIG. 10), suggesting increased ability of the novel compound to ameliorate obesity-induced kidney dysfunction.

Figure 11A:
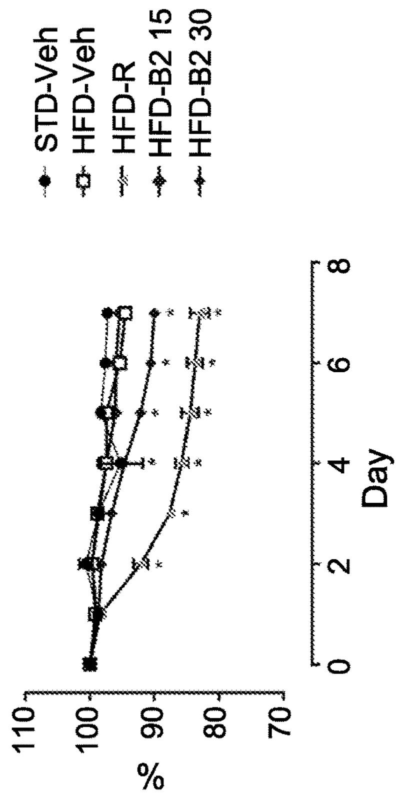
FIGS. 11A-B demonstrate the efficacy of higher doses of BNS002 in DIO mice. The efficacy of higher doses of BNS-002 (15 and 30 mg/kg, ip for 7 days) was next tested in DIO mice in comparison with rimonabant (10 mg/kg/d). Age- and sex-matched mice on standard chow served as controls. The overweight of mice on HFD were significantly reduced by rimonabant and BNS-002 at a dose of 30 mg/kg (FIGS. 11A and 11B), whereas no effect on body weight reduction was observed in the group treated with BNS-002 at 15 mg/kg.
Figure 11B:
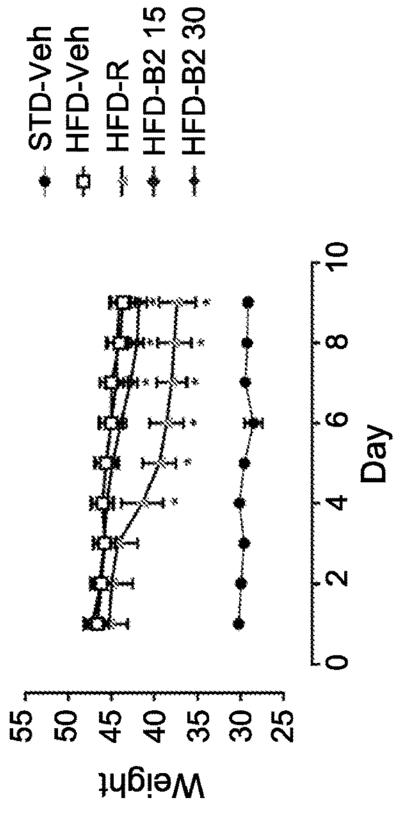

The efficacy of higher doses of BNS-002 (15 and 30 mg/kg, ip for 7 days) was next tested in DIO mice in comparison with rimonabant (10 mg/kg/d). Age- and sex-matched mice on standard chow served as controls. The overweight of mice on HFD were significantly reduced by rimonabant and BNS-002 at a dose of 30 mg/kg (FIGS. 11A and 11B), whereas no effect on body weight reduction was observed in the group treated with BNS-002 at 15 mg/kg.

Synthesis and characterization of 5-(4-chlorophenyl)-1-(2,4-dichlorophenyl)-4-methyl-N-(2,2,6,6-tetramethyl-1-oxo-1-piperidin-4-yl)-1H-pyrazole-3-carboxamide (BB1+TMP)

Synthesis procedure. N,N'-Dicyclohexylcarbodiimide (DCC, 1.08 g, 5.24 mmol) was added to 5-(4-chlorophenyl)-1-(2,4-dichlorophenyl)-4-methyl-1H-pyrazole-3-carboxylic acid (BB1, 1 g, 2.26 mmol) in $CH_2Cl_2$ (70 ml). The resultant mixture was stirred for 10 min and then, 4-Amino TEMPO (free radical) (TMP, 0.45 g, 2.62 mmol) was added. The reaction mixture was stirred at room temperature over 24 h. An orange solution and a white precipitate were formed. The mixture was filtered on white paper filter and washed with $CH_2Cl_2$ (50 ml). Following filtration, the $CH_2Cl_2$ was evaporated, and the crude was dissolved in $CH_2Cl_2$ again (50 ml). An orange solution and a white precipitate were formed. The mixture was filtered on white paper filter and washed with $CH_2Cl_2$ (50 ml). Following filtration, the $CH_2Cl_2$ was evaporated.

A 74% yield before column chromatography was obtained. The orange viscous oil was dissolved again in 10 ml of $CH_2Cl_2$ and incorporated with silica powder (silica gel 60), dried and load to pre-prepared silica column (radius 5 cm, length 25 cm). The separation and the purification were completed as follows: 2 fold volumes of column capacity were washed with hexane; followed by 2 volumes of column capacity with hexane:ethyl acetate (90:10) and ended after 4 volumes of column capacity with hexane:ethyl acetate (80:20).

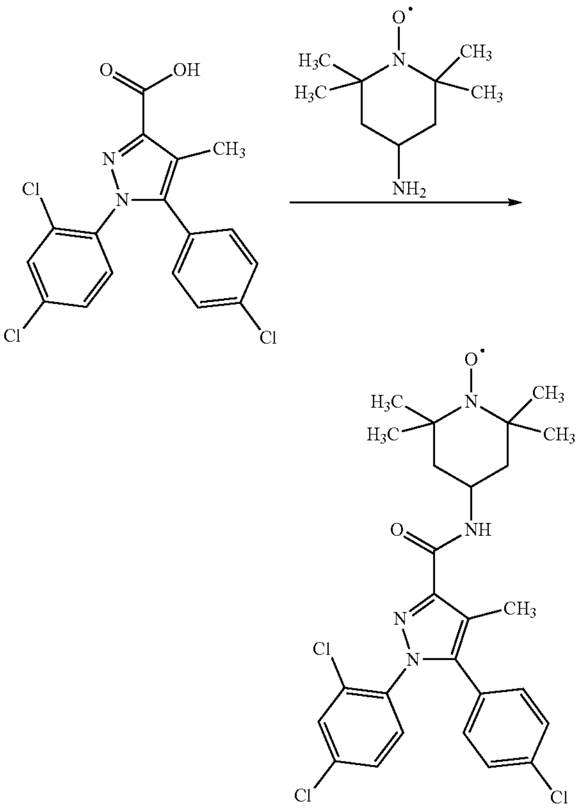

Characterization. The LC-MS and the Elemental analysis confirmed the structure of the title compound. The HPLC shows purity above 98%.
Elemental Analysis

TABLE 1

| Batch Sample | Code Sample | % C | % H | % N |
|---|---|---|---|---|
| 6-6956 | BB1 + TMP | 58.31<br>57.27 | 5.23<br>5.44 | 10.46<br>9.91 |

Synthesis and characterization of 2,2,6,6-tetramethyl-1-piperidin-4-yl 5-(4-chlorophenyl)-1-(2,4-dichlorophenyl)-4-methyl-1H-pyrazole-3-carboxylate (BB1+EST)

Synthesis procedure. N,N'-Dicyclohexylcarbodiimide (DCC, 1.08 g, 5.24 mmol) was added to 5-(4-chlorophenyl)-1-(2,4-dichlorophenyl)-4-methyl-1H-pyrazole-3-carboxylic acid (BB1, 1 g, 2.26 mmol) in $CH_2Cl_2$ (70 ml). The resultant mixture was stirred for 10 min and then, 4-Hydroxy TEMPO (free radical) (EST, 0.45 g, 2.62 mmol) was added. The reaction mixture was stirred at room temperature over 24 h. An orange solution and a white precipitate were formed. The mixture was filtered on white paper filter and washed with $CH_2Cl_2$ (50 ml). Following filtration, the $CH_2Cl_2$ was evaporated, and the crude was dissolved in $CH_2Cl_2$ again (50 ml). An orange solution and a white precipitate were formed. The mixture was filtered on white paper filter and washed with $CH_2Cl_2$ (50 ml). Following filtration, the $CH_2Cl_2$ was evaporated.

A 70% yield before column chromatography was obtained. The orange viscous oil was dissolved again in 10 ml of $CH_2Cl_2$ and incorporated with silica powder (silica gel 60), dried and load to pre-prepared silica column (radius 5 cm, length 25 cm). The separation and the purification were completed as follows: 2 fold volumes of column capacity were washed with hexane; followed by 2 volumes of column capacity with hexane:ethyl acetate (90:10) and ended after 4 volumes of column capacity with hexane:ethyl acetate (80:20).

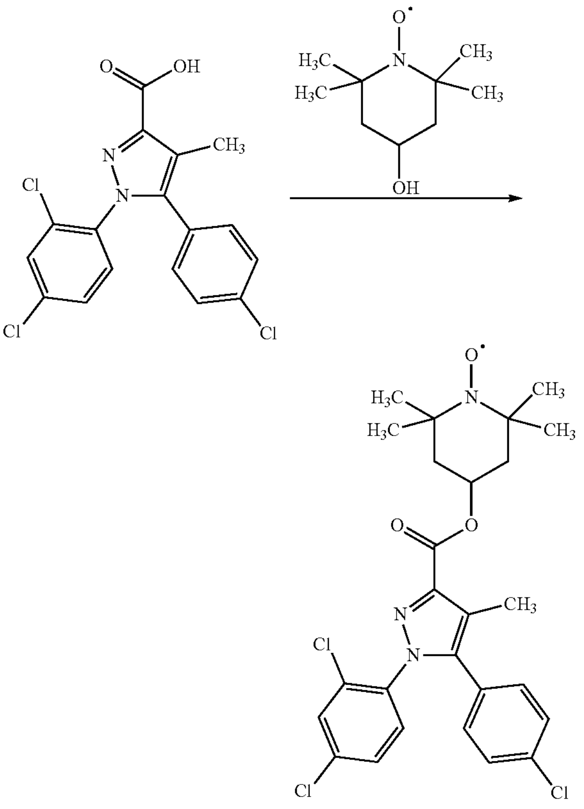

Characterization. The LC-MS and the Elemental analysis confirmed the structure of the title compound. The HPLC shows purity above 98%.
Elemental Analysis

TABLE 2

| Batch Number | Date | Code Sample | % C | % H | % N |
|---|---|---|---|---|---|
| 6-7154 | | | 58.20 | 5.22 | 7.83 |
| | 30 Jul. 2019 | BB1_EST | 57.71 | 5.17 | 7.54 |

Synthesis and characterization of 10-(4,5-dimethoxy-2-methyl-3,6-dioxocyclohexa-1,4-dien-1-yl) decyl 5-(4-chlorophenyl)-1-(2,4-dichlorophenyl)-4methyl-1H-pyrazole-3-carboxylate (BB1+IDB)

Synthesis procedure. N,N'-Dicyclohexylcarbodiimide (DCC, 1.3 g, 5.91 mmol) was added to 5-(4-chlorophenyl)-

1-(2,4-dichlorophenyl)-4-methyl-1H-pyrazole-3-carboxylic acid (BB1, 1.12 g, 2.95 mmol) in $CH_2Cl_2$ (70 ml). The resultant mixture was stirred for 10 min and then, Idebenone (IDB, 1, 2.95 mmol) was added. The reaction mixture was stirred at room temperature over 24 h. An orange solution and a white precipitate were formed. The mixture was filtered on white paper filter and washed with $CH_2Cl_2$ (50 ml). Following filtration, the $CH_2Cl_2$ was evaporated, and the crude was dissolved in $CH_2Cl_2$ again (50 ml). An orange solution and a white precipitate were formed. The mixture was filtered on white paper filter and washed with $CH_2Cl_2$ (50 ml). Following filtration, the $CH_2Cl_2$ was evaporated.

A 70% yield before column chromatography was obtained. The orange viscous oil was dissolved again in 10 ml of $CH_2Cl_2$ and incorporated with silica powder (silica gel 60), dried and load to pre-prepared silica column (radius 5 cm, length 25 cm). The separation and the purification were completed as follows: 2 fold volumes of column capacity were washed with hexane; followed by 2 volumes of column capacity with hexane:ethyl acetate (90:10) and ended after 4 volumes of column capacity with hexane:ethyl acetate (80:20).

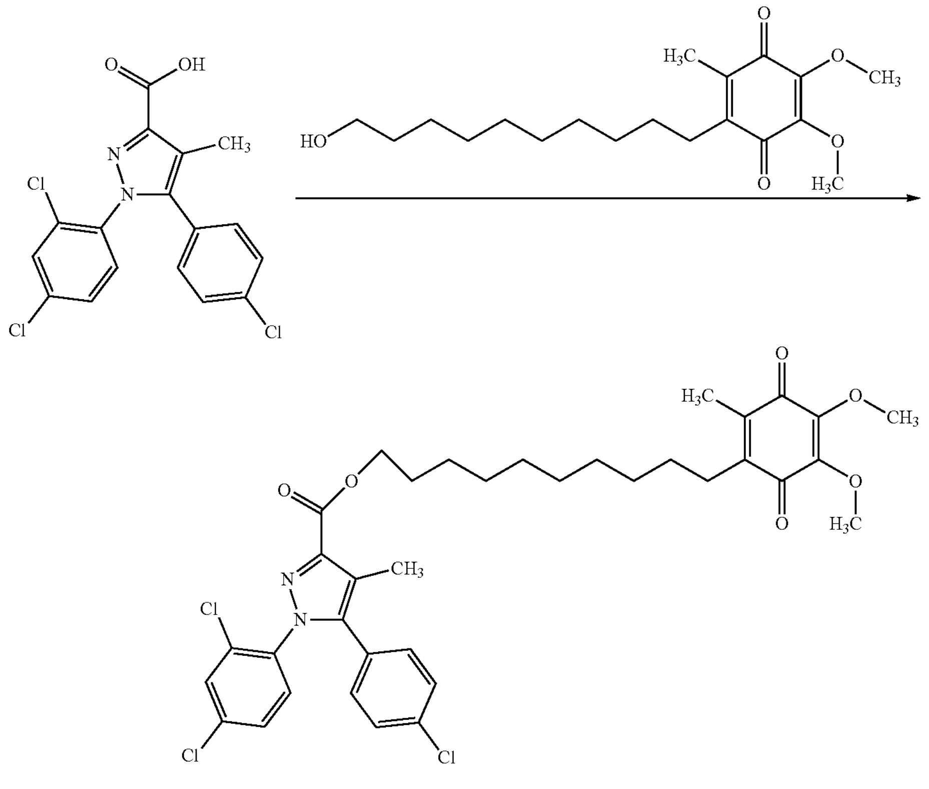

Characterization. The LC-MS and the H-NMR confirmed the structure of the title compound. The HPLC shows purity above 98%.

TMP, EST and IDB—In Vitro Binding Report

Radioligand binding assay. Binding of the tested compounds to CB1 receptor was assessed in competition displacement assays using [3H]CP-55,940 as the radioligand and crude membranes from mouse brain for CB1 receptor. Membranes were extracted according to an established protocol previously described by Catani V. M. and Gasperi V. [8]. Compounds were tested at different concentrations (10-5M-10-11M) and their ability to displace [3H]CP-55,940 was evaluated. Membranes with bound [3H]CP-55,940 were separated and washed from free ligand by vacuum filtration and bound [3H]CP-55,940 radioactivity was measured using a 13 counter. All data were in triplicates with Ki values extracted by nonlinear regression analysis using GraphPad Prism software.

Results

Figure 12:
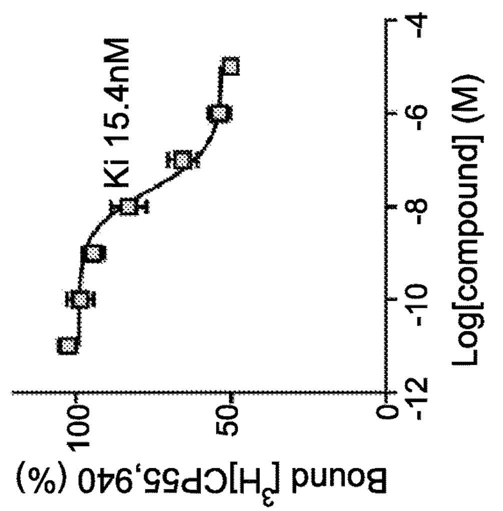
FIG. 12 provide Ki values determined for TMP using [$^3$H]CP-55,940 radioligand displacement assay.
Figure 13:
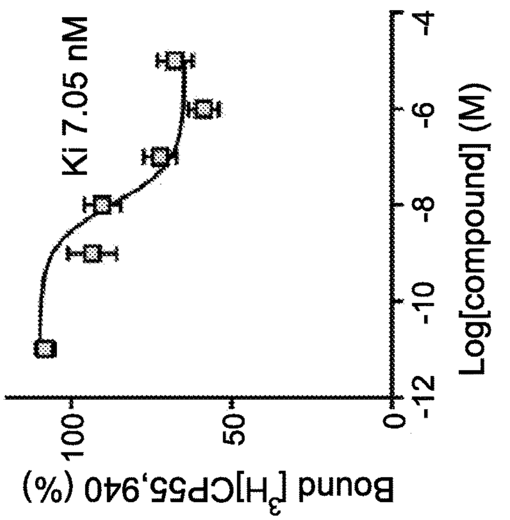
FIG. 13 provide Ki values determined for EST using [$^3$H]CP-55,940 radioligand displacement assay.
Figure 14:
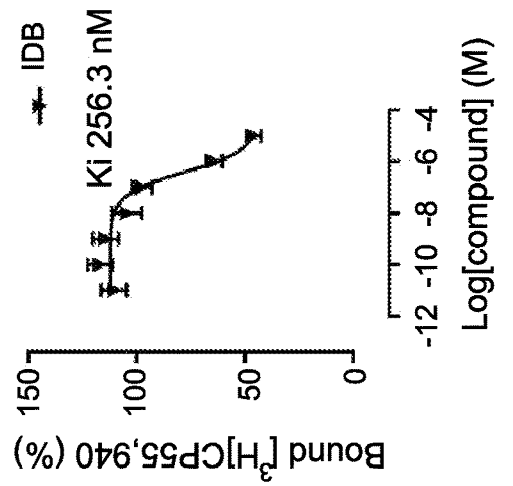
FIG. 14 provide Ki values determined for IDB using [$^3$H]CP-55,940 radioligand displacement assay.

In radioligand displacement assays, all three tested compounds were found active with high affinity to $CB_1$ receptor. Ki values were varying for each substance, ranging from 1.69 nM-446 nM for TMP (FIG. 12), 0.37 nM-7.81 nM for EST (FIG. 13) and 1.9 nM-134.6 nM for IDB (FIG. 14).

TMP, EST and IDB—In Vivo Safety Report (Lack of CNS Central Activity)

Centrally-mediated hyperactivity profile. Wild-type, male, C57Bl/6J mice (n=4-8) received a single dose of rimonabant (10 mg/kg, IP), TMP (35 mg/kg, IP), EST (40 mg/kg, IP), IDB (20 mg/kg, IP) or vehicle only (IP). Mice were placed in metabolic cages and their activity profile was evaluated. Locomotor activity was quantified by the number of disruptions of infrared XYZ beam arrays with a beam spacing of 0.25 cm in the Promethion High-Definition Behavioral Phenotyping System (Sable Instruments, Inc., Las Vegas, NV, USA).

Antagonizing cannabinoid-induced hypomotility. The ability of the different compounds to inhibit the hypomotility induced by HU210 (cannabinoid agonist) was evaluated. Wild-type, male, C57Bl/6J mice (n=4-10) received a single dose of rimonabant (10 mg/kg, IP), TMP (35 mg/kg, IP), EST (40 mg/kg, IP), IDB (20 mg/kg, IP) or vehicle only (IP). A half an hour thereafter, mice received a single dose of HU210 (30 ug/kg, IP) and their locomotor activity was evaluated as described above.

Results

Figure 15:
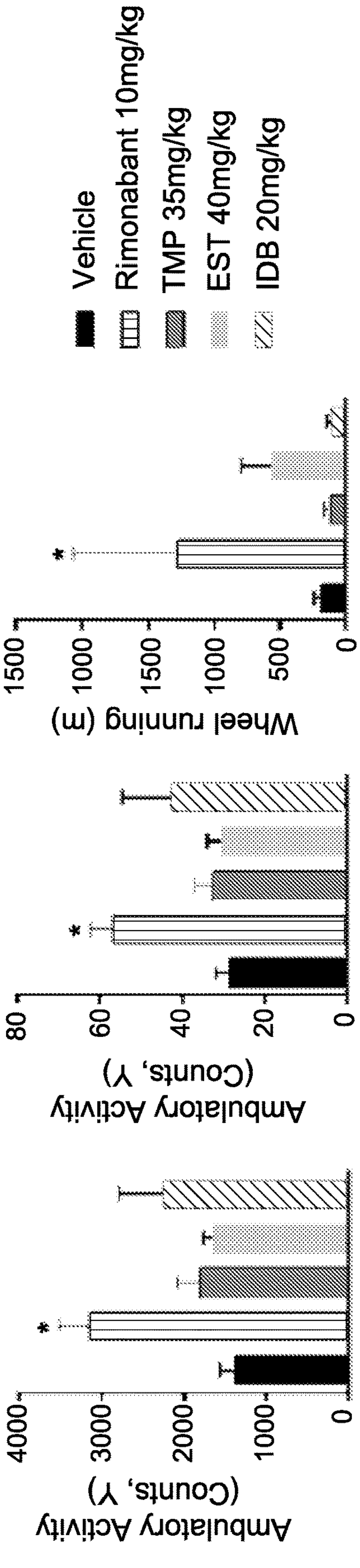
FIG. 15 shows the ability of IDB, EST, TMP and rimonabant (as a positive control) to induce centrally-mediated hyperactivity in mice. Wild-type, male, C57Bl/6J mice received a single dose of rimonabant (10 mg/kg, IP), IDB, EST, TMP (at 20, 40 and 35 mg/kg, IP respectively) or vehicle. Ambulatory activity was measured by the Promethion Metabolic System (Sable Instruments, Inc). Data represent the mean±SEM from 4-8 mice per group. *P<0.05 vs. Vehicle-treated control.
Figure 16:
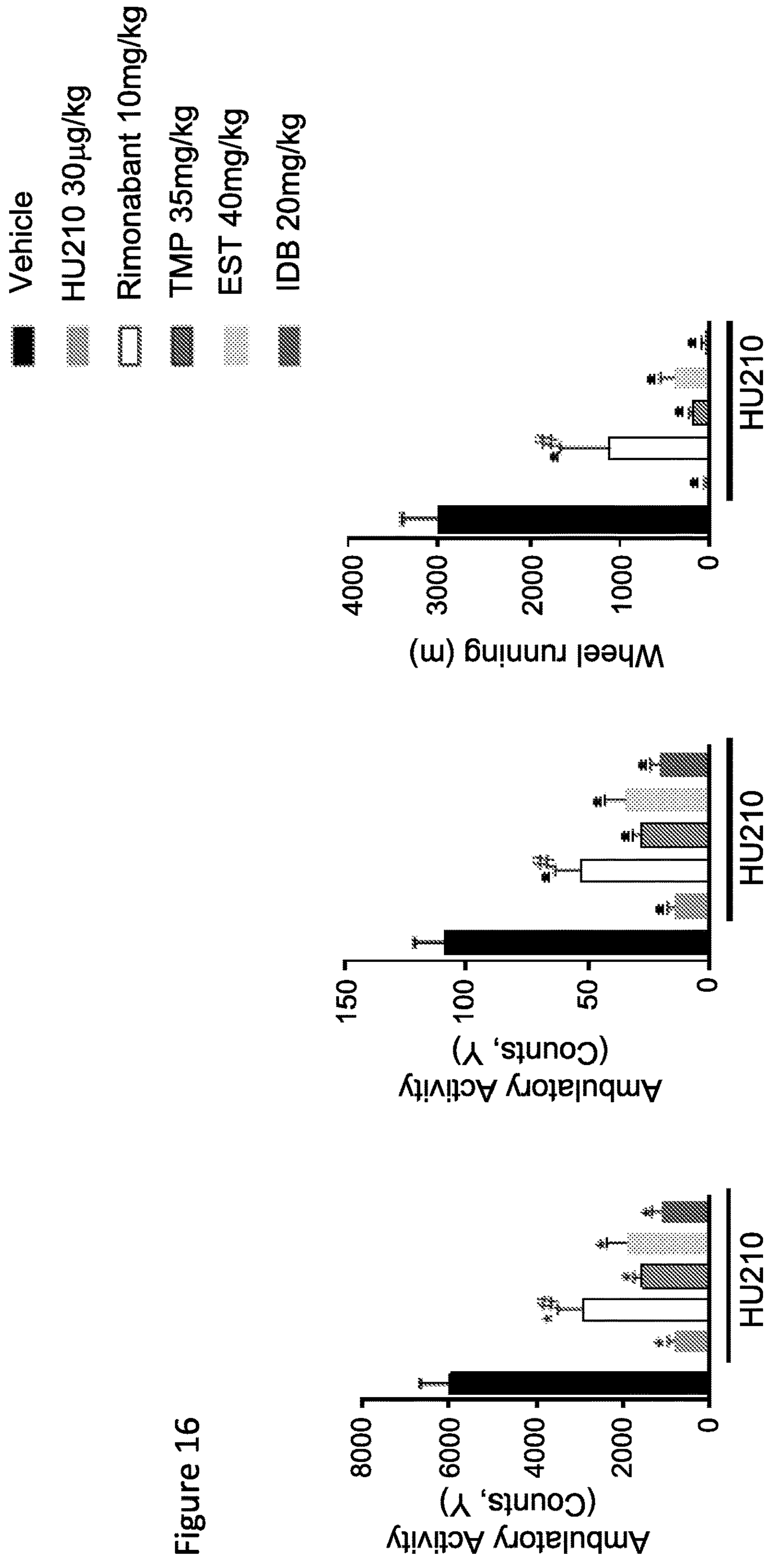
FIG. 16 demonstrates the ability of IDB, EST, TMP and rimonabant (as a positive control) to inhibit the hypomotility-induced by a $CB_1$ receptor agonist (HU210). Wild-type, male, C57Bl/6J mice received a single dose of rimonabant (10 mg/kg, IP), IDB, EST, TMP (at 20, 40 and 35 mg/kg IP, respectively) or vehicle. A half an hour after, mice received a single dose of HU210 (30 μg/kg, IP) and their locomotor activity was evaluated by the Promethion Metabolic System (Sable Instruments, Inc). Data represent the mean±SEM from 4-10 mice per group. *P<0.05 vs. Vehicle-treated control #P<0.05 vs. HU210.

Rimonabant (10 mg/kg) induced a marked increase in the activity profile in mice (FIG. 15), but no significant hyperactivity was recorded, compare to the vehicle group, following TMP (35 mg/kg, IP), EST (40 mg/kg, IP) and IDB (20 mg/kg, IP) injections (FIG. 15). The marked hypomotility induced in mice by the cannabinoid agonist HU210 (30 ug/kg, IP) was significantly blocked by rimonabant but was unaffected by the tested compounds (FIG. 16).

Figure 17A:
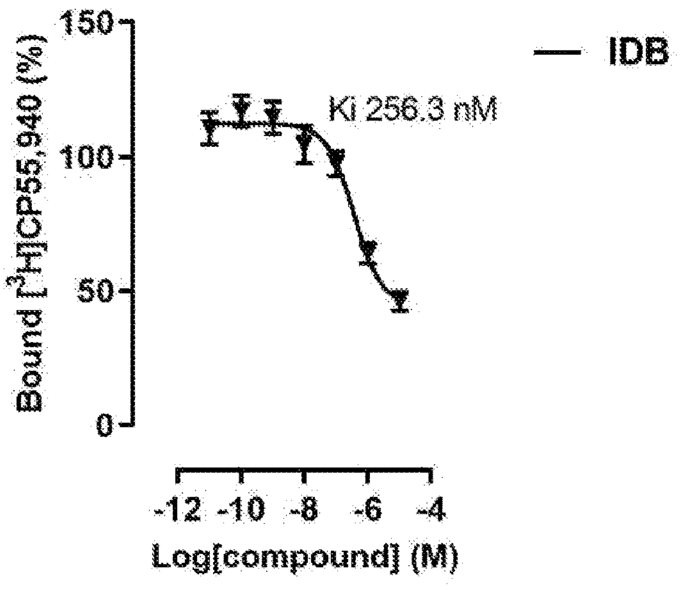
FIGS. 17A-B show that IDB has a $CB_1$ binding affinity of 256.3 nM (Ki) (A), and shows an inverse agonism profile, as tested by GTPγS binding (B). Data represent the mean±SEM of at least three independent experiments done in triplicates.
Figure 17B:
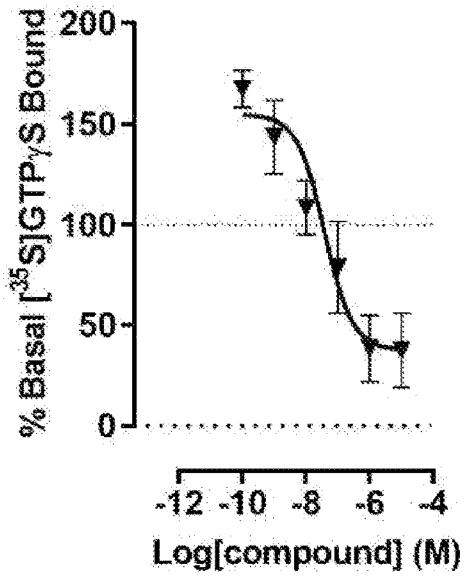
Figure 18A:
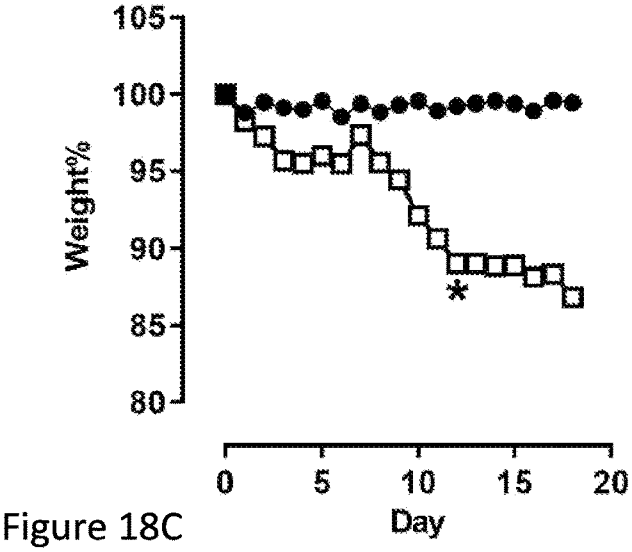
FIGS. 18A-F show that IDB (20 mg/kg/day for 20 days) reduced body weight (A, B), daily and total food intake (C, D) as well as reduced fat mas and increased lean mass (E, F) in DIO mice. Data represent the mean±SEM from 5 mice per group. *P<0.05 vs. Vehicle-treated control.
Figure 18B:
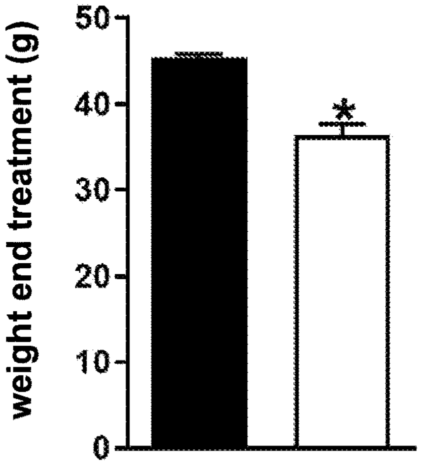
Figure 18C:
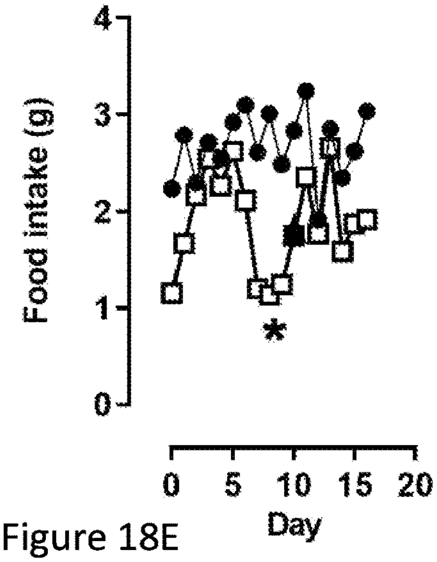
Figure 18D:
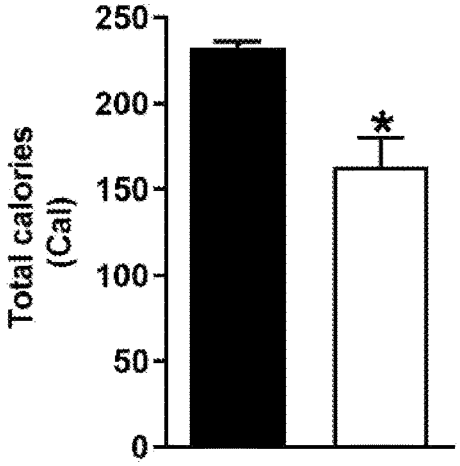
Figure 18E:
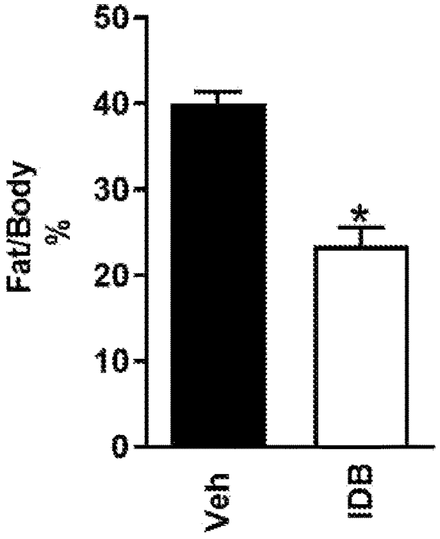
Figure 18F:
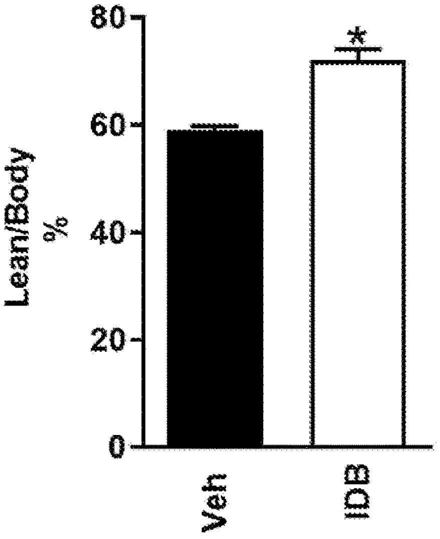

FIG. 17 shows that IDB has a CB1 binding affinity of 256.3 nM (Ki) (A), and shows an inverse agonism profile, as tested by GTPγS binding (B). Data represent the mean±SEM of at least three independent experiments done in triplicates.

IDB (20 mg/kg/day for 20 days) reduced body weight (A, B), daily and total food intake (C, D) as well as reduced fat mas and increased lean mass (E, F) in DIO mice is shown in FIG. 18. Data represent the mean±SEM from 5 mice per group. *P<0.05 vs. Vehicle-treated control.

Figures 19A, 19B, 19C:
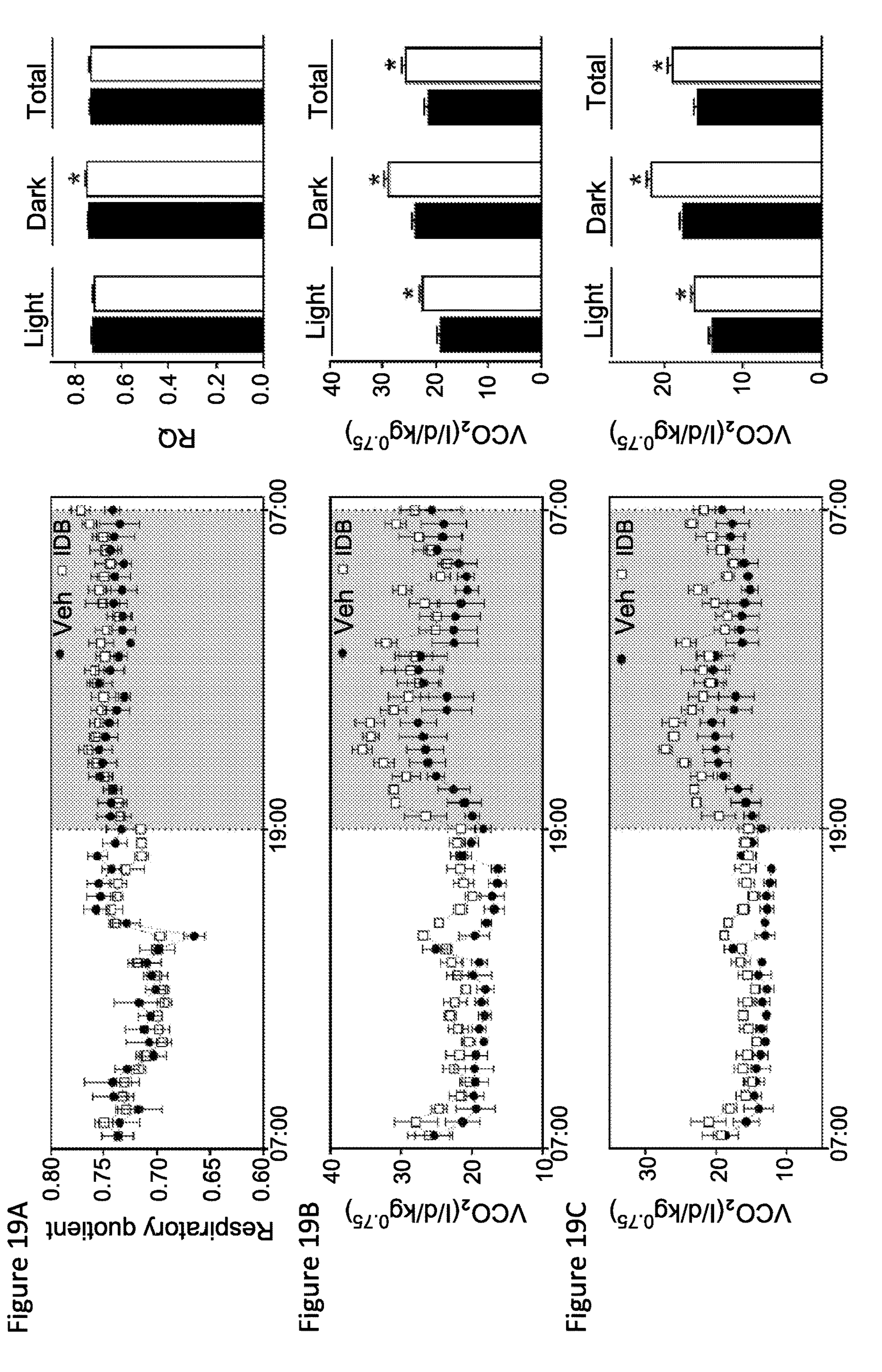
FIGS. 19A-F demonstrate that chronic IDB administration (20 mg/kg/day for 20 days) induces significant changes in metabolic parameters measured by the Promethion High-Definition Behavioral Phenotyping System (Sable Instruments, Inc.) over a 24 hr period. Respiratory quotient (A), VO2 (B), VCO2 (C), total energy expenditure (D), fat oxidation (E), and carbohydrate oxidation (F). Data are mean±SEM from 4 mice per group. *P<0.05 vs. Vehicle-treated control.
Figures 19D, 19E, 19F:
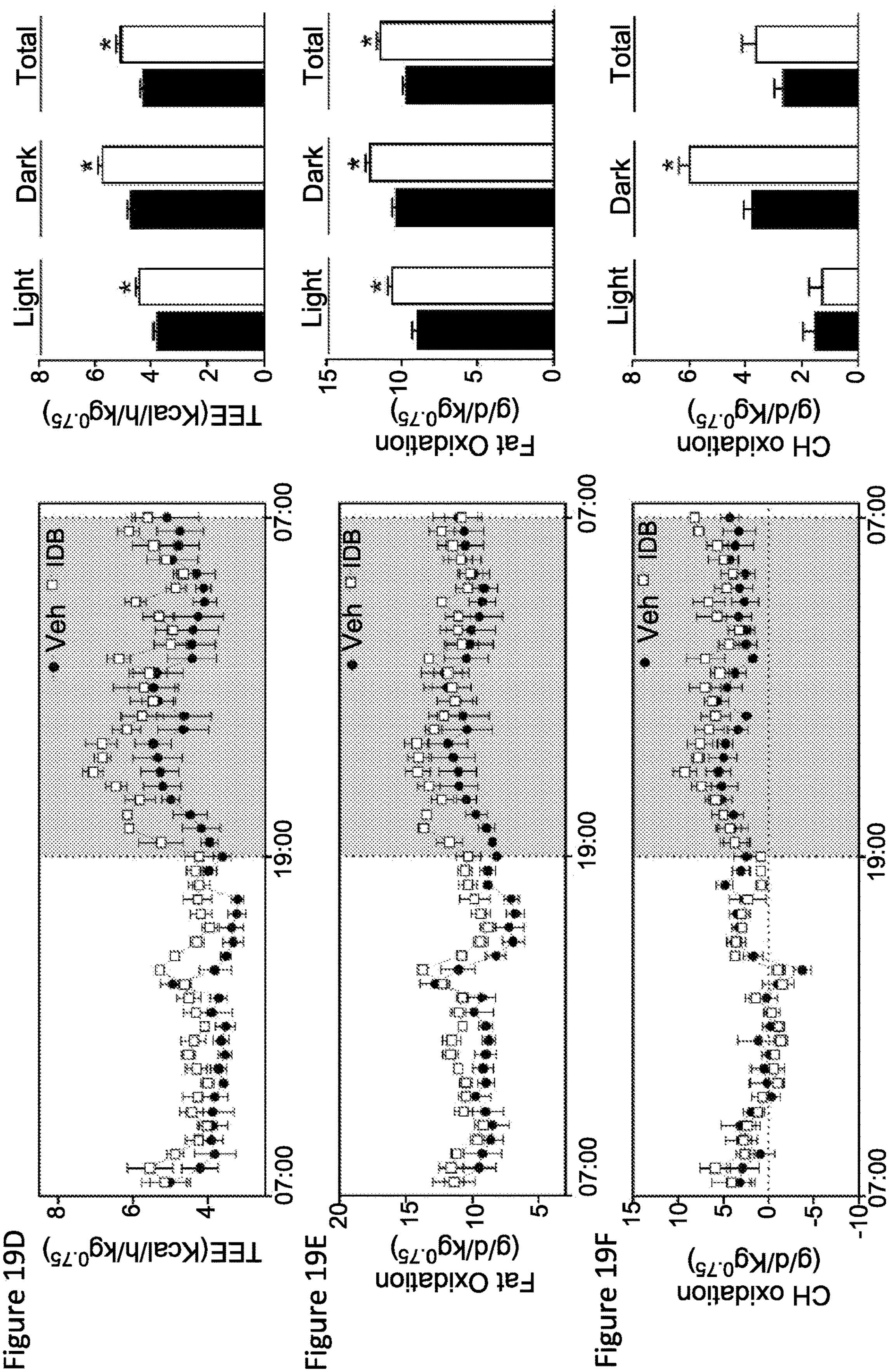

In FIG. 19 chronic IDB administration (20 mg/kg/day for 20 days) is shown to induce significant changes in metabolic parameters measured by the Promethion High-Definition Behavioral Phenotyping System (Sable Instruments, Inc.) over a 24 hr period. Respiratory quotient (A), VO2 (B), VCO2 (C), total energy expenditure (D), fat oxidation (E), and carbohydrate oxidation (F). Data are mean±SEM from 4 mice per group. *P<0.05 vs. Vehicle-treated control.

Figures 20A, 20B:
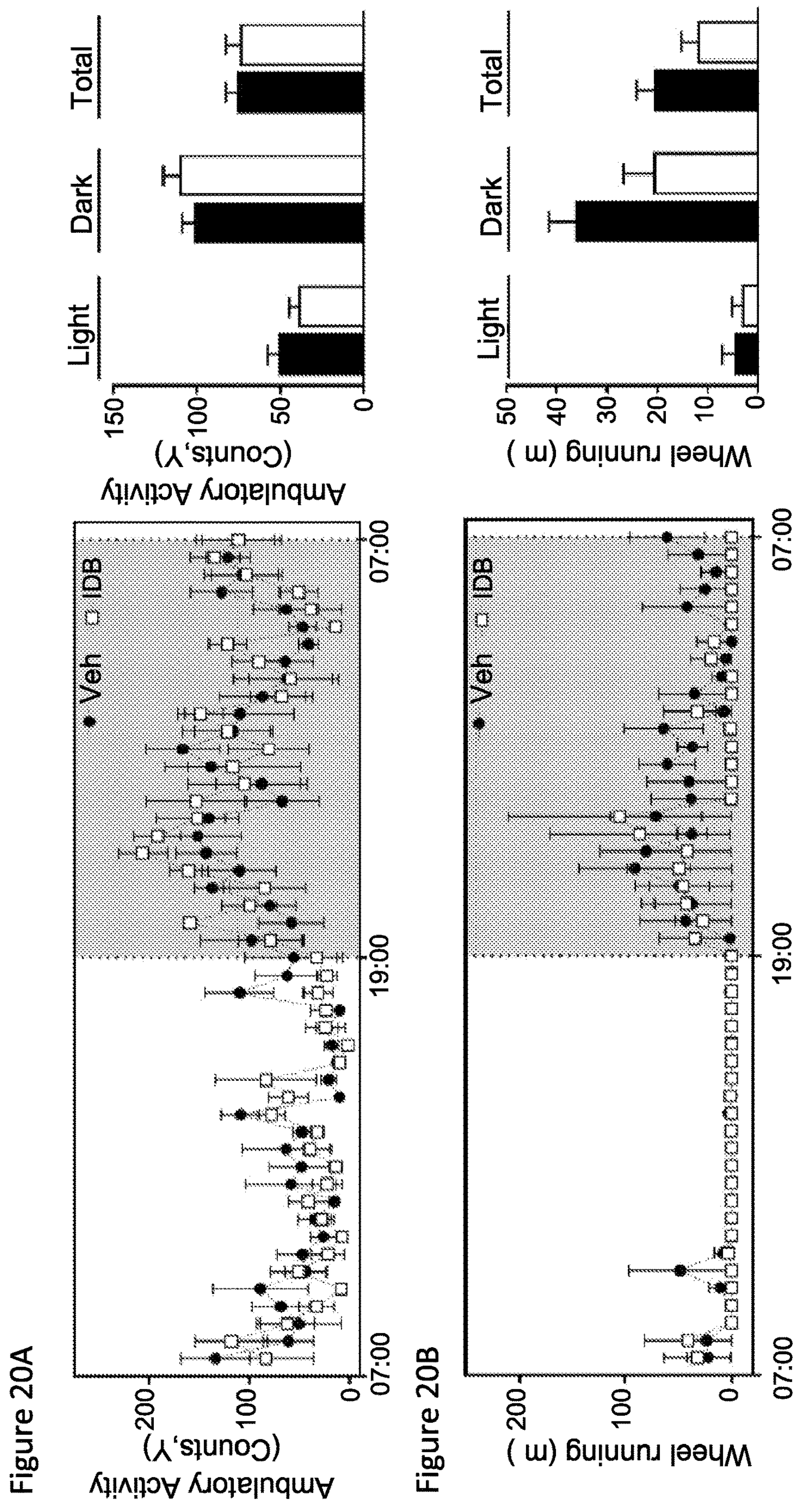
FIGS. 20A-D demonstrates that chronic IDB administration (20 mg/kg/day for 20 days) affects ambulation in DIO mice. Ambulatory activity (A), ability to run on a wheel (B), voluntary activity (C), and total meter (D). Method: Mice were monitored by the Promethion High-Definition Behavioral Phenotyping System (Sable Instruments, Inc.) over a 24 hr period. Data are mean±SEM from 4 mice per group.
Figure 20C:
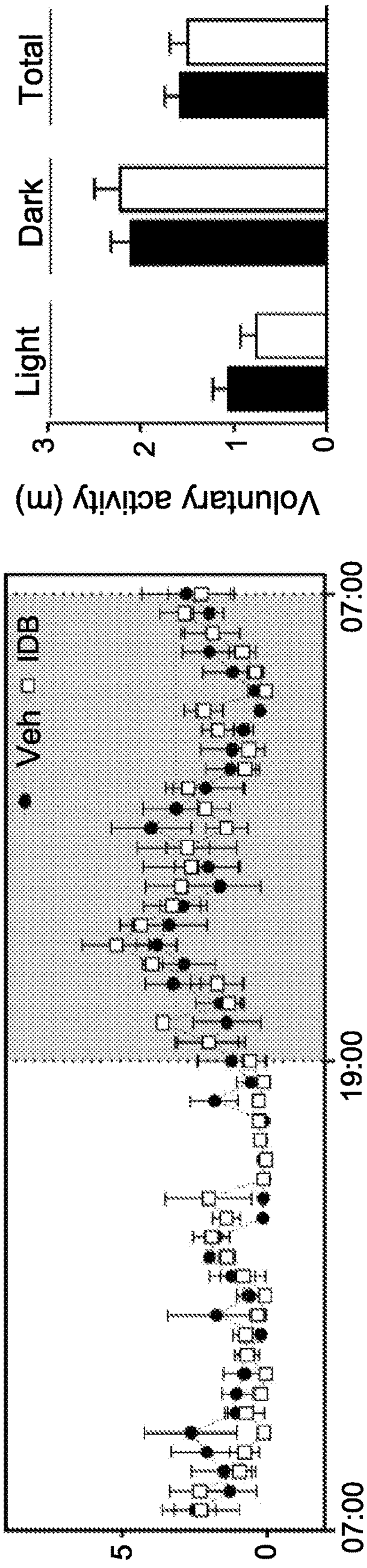
Figure 20D:
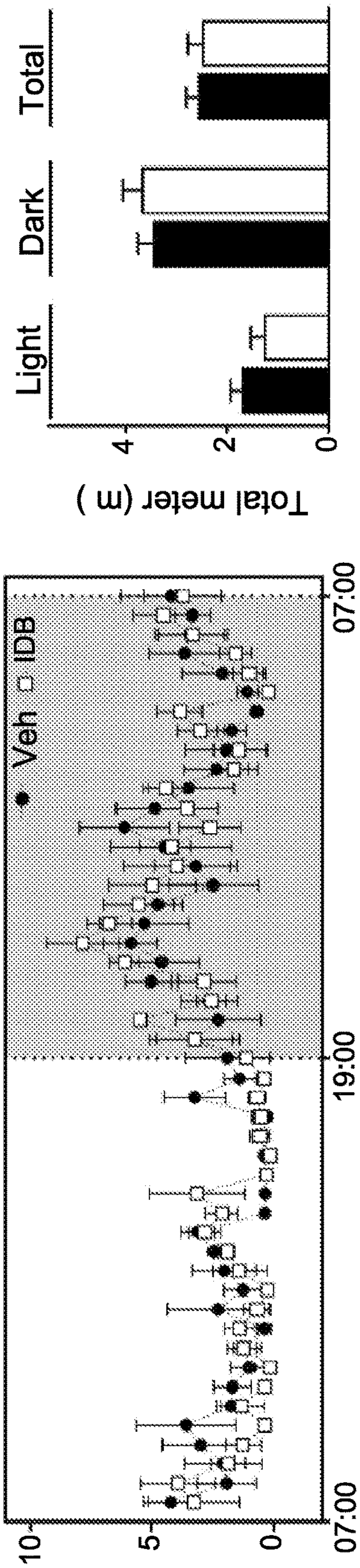

In FIG. 20 chronic IDB administration (20 mg/kg/day for 20 days) is shown not to affect ambulation in DIO mice. Ambulatory activity (A), ability to run on a wheel (B), voluntary activity (C), and total meter (D). Method: Mice were monitored by the Promethion High-Definition Behavioral Phenotyping System (Sable Instruments, Inc.) over a 24 hr period. Data are mean±SEM from 4 mice per group.

Figures 21A, 21B, 21C, 21D, 21E, 21F, 21G, 21H, 21I:
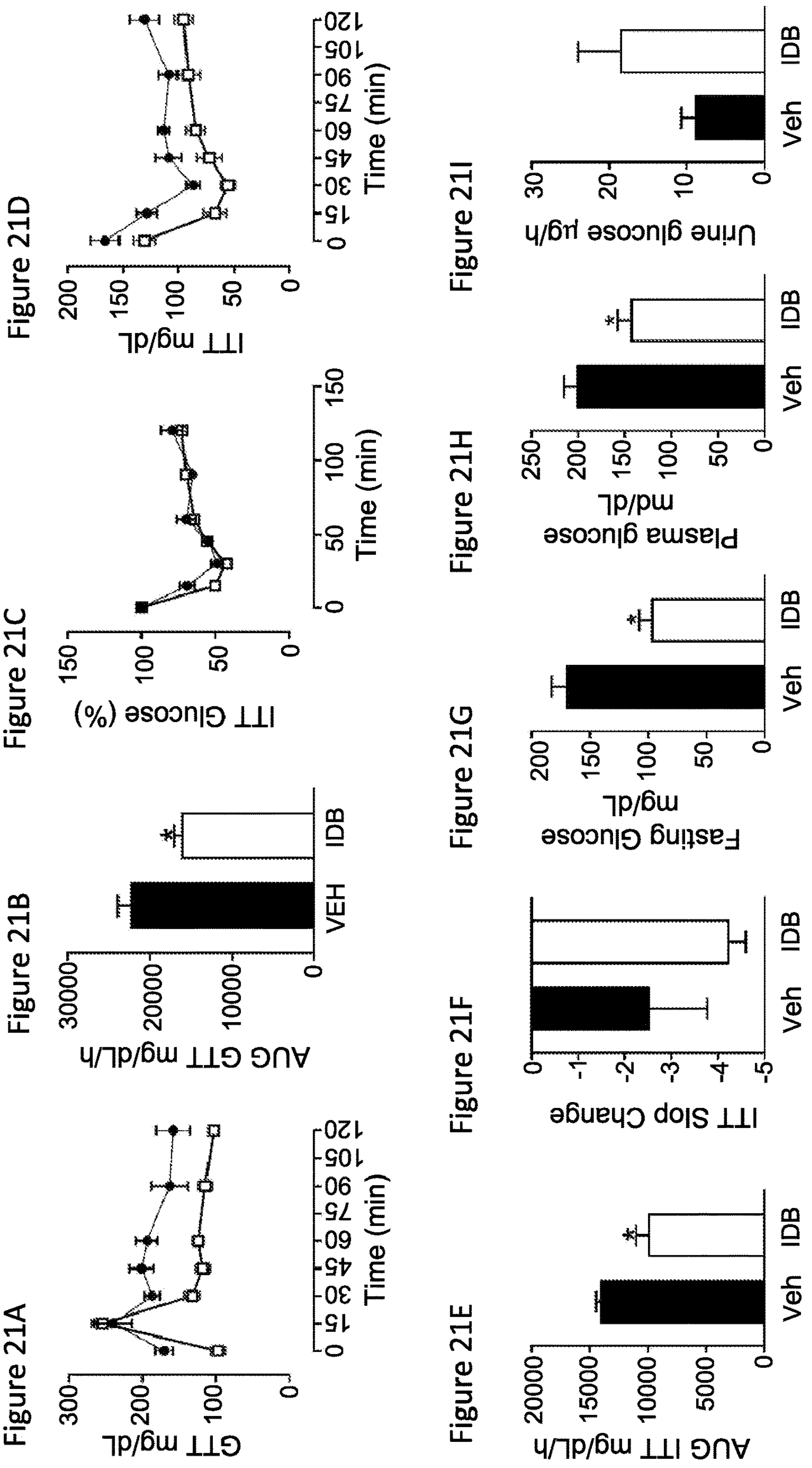
FIGS. 21A-I show the effect of chronic IDB administration (20 mg/kg/day for 20 days) on glycemic control. Mice on high-fat diet for 20 weeks were treated chronically with IDB or vehicle, and glucose homeostasis was assessed. Note that IDB reduced glucose tolerance (A-B), improved insulin sensitivity (C—F) as well as reduced fasting (G) and fed (H) glucose levels. In addition, IDB increases glycosuria (I). Data represent the mean±SEM from 5 mice per group. *P<0.05 vs. Vehicle-treated control.

In FIG. 21 the effect of chronic IDB administration (20 mg/kg/day for 20 days) on glycemic control is demonstrated. Mice on high-fat diet for 20 weeks were treated chronically with IDB or vehicle, and glucose homeostasis was assessed. Note that IDB reduced glucose tolerance (A-B), improved insulin sensitivity (C—F) as well as reduced fasting (G) and fed (H) glucose levels. In addition, IDB increases glycosuria (I). Data represent the mean±SEM from 5 mice per group. *P<0.05 vs. Vehicle-treated control.

In FIG. 22 chronic IDB administration (20 mg/kg/day for 20 days) is shown to reduce HFD-induced hepatic steatosis and liver injury in mice. An elevated in fat vacuoles deposition, measured by H&E staining, was evident in the DIO mice treated with vehicle compared with the IDB-treated animals on the same diet (A). Furthermore, a decrease in liver weight (B) as well as a reduction in liver enzymes (AST, ALT, and ALP), measured by the COBAS Chemistry analyzer, was noticeable in the IDB-treated mice. Data represent the mean±SEM from 5 mice per group. *P<0.05 vs. Vehicle-treated control.

Figures 23A, 23B, 23C, 23D, 23E:
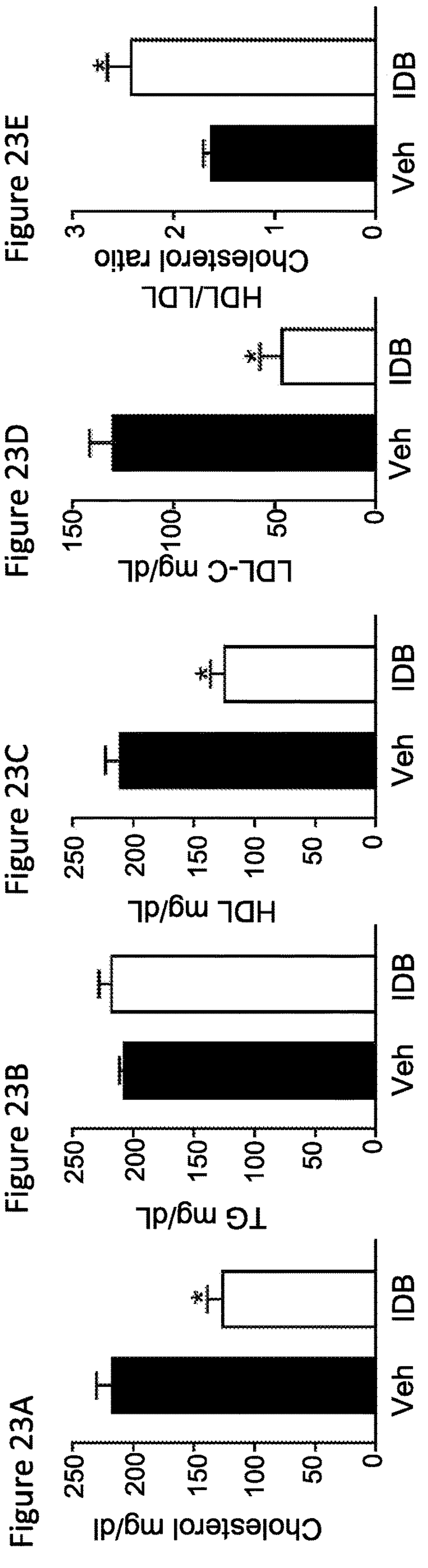
FIGS. 23A-E show that chronic IDB administration (20 mg/kg/day for 20 days) improves dyslipidemia in DIO mice. IDB was able to reduce total cholesterol (A), triglycerides (B), HDL (C), and LDL (D) as well as to increase HDL-to-LDL ratio (E). Data represent the mean±SEM from 5 mice per group. *P<0.05 vs. Vehicle-treated control.

In FIG. 23 chronic IDB administration (20 mg/kg/day for 20 days) is shown to improve dyslipidemia in DIO mice. IDB was able to reduce total cholesterol (A), triglycerides (B), HDL (C), and LDL (D) as well as to increase HDL-to-LDL ratio (E). Data represent the mean±SEM from 5 mice per group. *P<0.05 vs. Vehicle-treated control.

Figure 10:
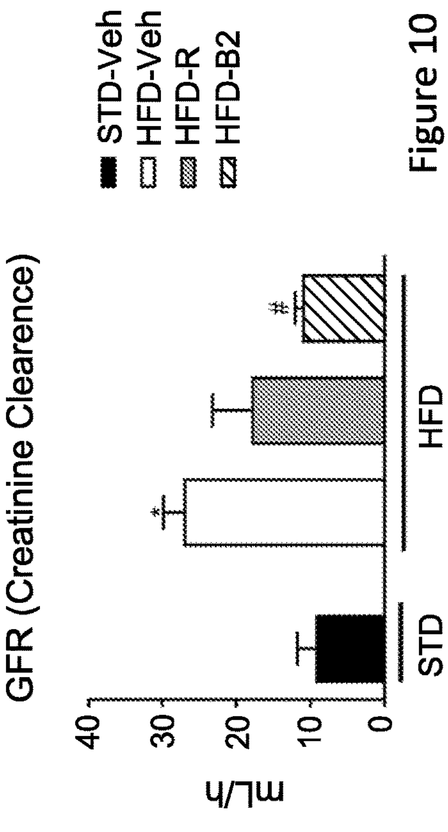
FIG. 10 shows efficacy of rimonabant and BNS-002 in reversing HI-D-induced kidney hyperfiltration. In addition, HFD-induced kidney hyperfiltration was completely normalized by BNS-002 (FIG. 10), suggesting increased ability of the novel compound to ameliorate obesity-induced kidney dysfunction.
Figures 22A, 22B:
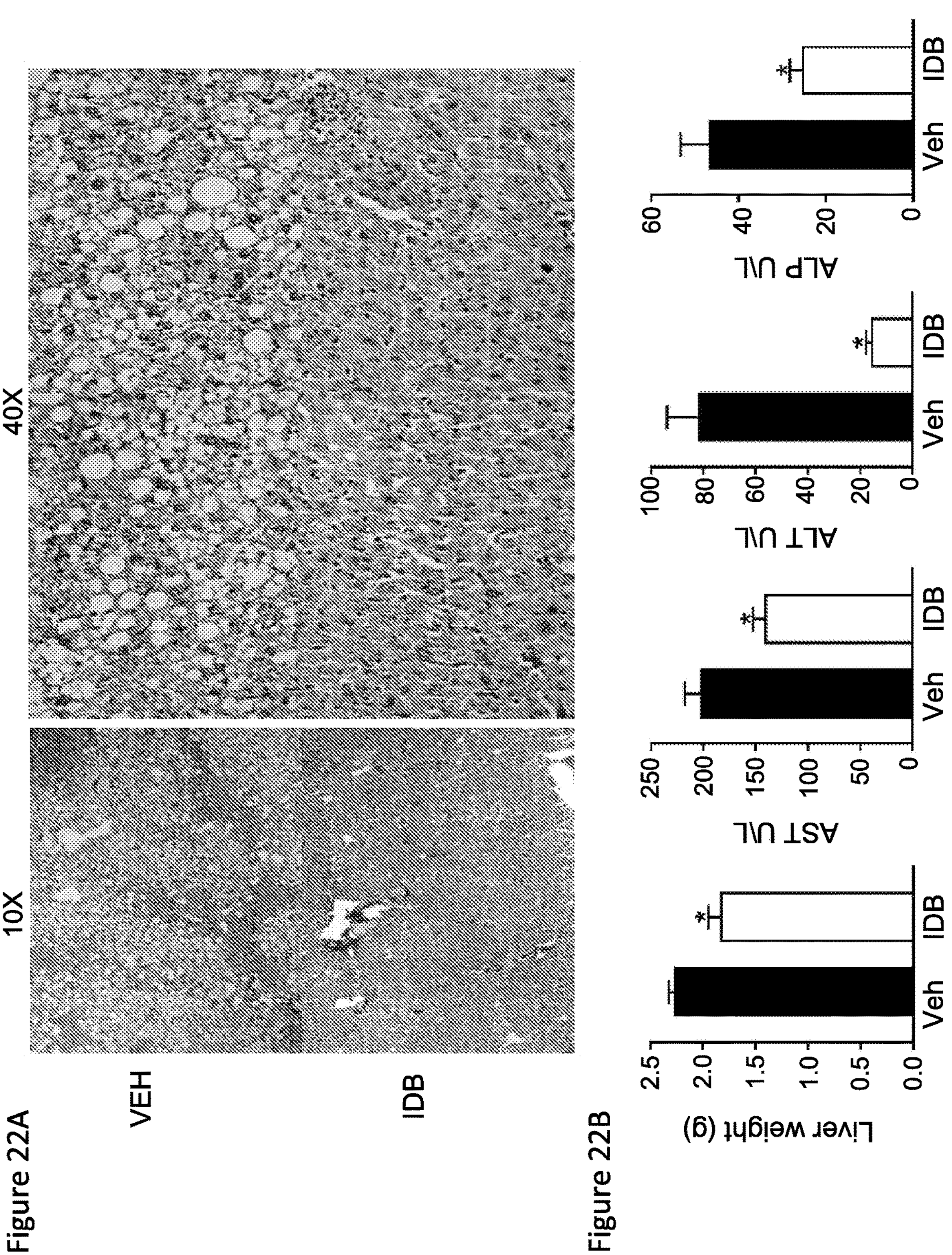
FIGS. 22A-B show that chronic IDB administration (20 mg/kg/day for 20 days) reduces HFD-induced hepatic steatosis and liver injury in mice. An elevated in fat vacuoles deposition, measured by H&E staining, was evident in the DIO mice treated with vehicle compared with the IDB-treated animals on the same diet (A). Furthermore, a decrease in liver weight (B) as well as a reduction in liver enzymes (AST, ALT, and ALP), measured by the COBAS Chemistry analyzer, was noticeable in the IDB-treated mice. Data represent the mean±SEM from 5 mice per group. *P<0.05 vs. Vehicle-treated control.

One very important difference between BNS-002 and IDB reside in the different impact on the liver and kidney functions. As can be seen in FIG. 10, HFD-induced kidney hyperfiltration was completely normalized by BNS-002, suggesting increased ability of the novel compound to ameliorate obesity-induced kidney dysfunction. Whereas IDB has no effect compared to the control. Furthermore, HFD-induced hepatic steatosis, as reflected in elevated fat vacuoles in the liver, was completely reversed by rimonabant and partially by BNS-002 (FIG. 9). Whereas chronic IDB administration (20 mg/kg/day for 20 days) of IDB reduces HFD-induced hepatic steatosis and liver injury in mice. An elevated in fat vacuoles deposition, measured by H&E staining, was evident in the DIO mice treated with vehicle compared with the IDB-treated animals on the same diet (FIG. 22A). Furthermore, a decrease in liver weight (FIG. 22B) as well as a reduction in liver enzymes (AST, ALT, and ALP), measured by the COBAS Chemistry analyzer, was noticeable in the IDB treated mice. Data represent the mean±SEM from 5 mice per group. *P<0.05 vs. Vehicle-treated control.

The invention claimed is:

1. A compound selected from compounds:

(A) of the general formula (II):

(II)

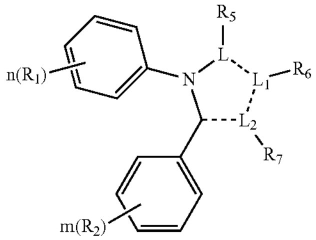

wherein each of $R_1$ and $R_2$, independently of the other, is a group selected from —H, halide, —CN, —$C_1$-$C_5$alkyl-OH and —OH;

each of n and m, independently of the other, is an integer between 0 and 5, designating the number of substituents on the ring;

one of L, $L_1$ and $L_2$ is a nitrogen atom and the others of L, $L_1$ and $L_2$ are each a carbon atom;

each of $R_5$, $R_6$ and $R_7$, independently of the other, is selected from —H, —$C_1$-$C_3$alkyl, —C(═O)—OH, —C(═O)—O—$R_8$, —C(═O)—NR'$R_8$, halide, —CN, —OH, and —NR'R"; or one of $R_5$ and $R_6$ or $R_6$ and $R_7$ together with the atoms to which they bond form a 5-, 6-, 7- or 8-membered carbocyclic ring optionally containing between 1 and 3 heteroatoms selected from N, O and S; or one of $R_5$, $R_6$ and $R_7$ is absent;

the 5-, 6-, 7- or 8-membered carbocyclic ring is optionally substituted by at least one functionality selected from —H, —$C_1$-$C_{25}$alkyl, —$C_2$-$C_{25}$alkenyl, —$C_2$-$C_{25}$alkynyl, —$C_6$-$C_{10}$aryl, an hydroxyl, an amine, a halide, —$ONO_2$, —$NO_2$, —S—, —S—$C_1$-$C_5$alkyl, —S—$C_2$-$C_5$alkenyl, —S—$C_2$-$C_5$alkynyl, —C(═O)—, —C(═O)—$C_1$-$C_{25}$alkyl, —C(═O)—O—$C_1$-$C_5$alkyl, —C(═O)—O—$C_2$-$C_5$alkenyl, —C(═O)—O—$C_2$-$C_5$alkynyl, —C(═O)—NR'R"R"', —C(═O)—NR'—C(═O)—$C_1$-$C_{25}$alkyl, —C(═O)—NR'—C(═O)—$C_2$-$C_{25}$alkenyl, —C(═O)—NR'—C(═O)—$C_2$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-

$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2C(CH_3)_2$—O-aryl-Cl, idebenonyl-derivative, -pyridine-3-C(═O)—OH and —NR'R"R'";

the 5-, 6-, 7- or 8-membered carbocyclic ring is optionally substituted by at least one functionality selected from structures (A) through (H):

(A)

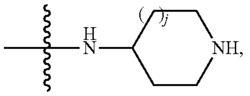

(B)

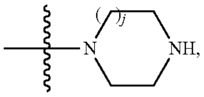

(C)

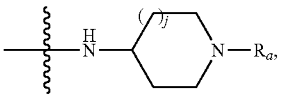

(D)

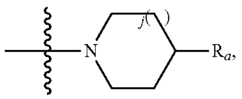

(E)

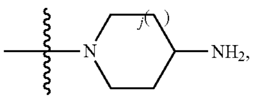

-continued (F)

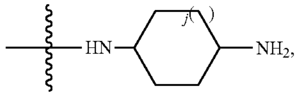

(G)

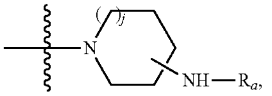

and (H)

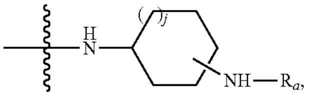

wherein in each functionality (A) through (H), the wavy line indicates point or bond of connectivity, j is 0 or 1 and Ra is selected from —H, —$C_1$-$C_{25}$alkyl, —$C_2$-$C_{25}$alkenyl, —$C_2$-$C_{25}$alkynyl, —C(═O)—$C_6$-$C_{10}$aryl and —C(═O)—$C_3$-$C_{10}$heteroaryl, wherein in functionalities (G) and (H) the pendant-NH—Ra group appears between 1 and 11 times at any position along the carbocycle;

$R_8$ is selected from —H, —$C_1$-$C_{25}$alkyl, —$C_2$-$C_{25}$alkenyl, —$C_2$-$C_{25}$alkynyl, —$C_6$-$C_{10}$aryl and $C_3$-$C_{10}$heteroaryl, each of which being optionally substituted by at least one functionality selected from an hydroxyl, an amine, a halide, —$ONO_2$, —$NO_2$, —S—, —S—$C_1$-$C_5$alkyl, —S—$C_2$-$C_5$alkenyl, —S—$C_2$-$C_5$alkynyl, —C(═O)—, —C(═O)—$C_1$-$C_{25}$alkyl, —C(═O)—O—$C_1$-$C_5$alkyl, —C(═O)—O—$C_2$-$C_5$alkenyl, —C(═O)—O—$C_2$-$C_5$alkynyl, —C(═O)—NR'R"R'", —C(═O)—NR'—C(═O)—$C_1$-$C_{25}$alkyl, —C(═O)—NR'—C(═O)—$C_1$-$C_{25}$alkenyl, —C(═O)—NR'—C(═O)—$C_1$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-$C_{10}$heteroaryl, —NHC(═O)$C_1$-$C_{25}$alkylene-$C_3$-$C_{10}$heteroaryl, —NHC(═O)$C_2$-$C_{25}$alkenylene-$C_3$-$C_{10}$heteroaryl, —NHC(═O)$C_2$-$C_{25}$alkynylene-$C_3$-$C_{10}$heteroaryl, 2,2,6,6-tetramethylpiperidin-1-ol-4-yl free radical, —NHC(═O)C$(CH_3)_2$—O-aryl-Cl, —NHC(═O)$CH_2C(CH_3)_2$—O-aryl-Cl, idebenonyl-derivative, -pyridine-3-C(═O)—OH and —NR'R"R'";

$R_{10}$ is selected from —H, —$C_1$-$C_{25}$alkyl, —$C_2$-$C_{25}$alkenyl, —$C_2$-$C_{25}$alkynyl, —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-aryl-Cl, idebenonyl-derivative, -pyridine-3-C(═O)—OH and —NR'R"R'";

each of R', R" and R'" is independently selected from H, $C_1$-$C_5$alkyl, $C_2$-$C_5$alkenyl, $C_2$-$C_5$alkynyl, —C(═O)—$C_2$-$C_{25}$alkyl, —C(═O)—$C_2$-$C_{25}$alkenyl and $C_5$-$C_{25}$alkynyl; or wherein one of R', R" and R'" is absent; and wherein each bond between N-L, L-$L_1$, $L_1$-$L_2$ and $L_2$-C (designated ---) is a single or double bond;

(B) of formula (III):

(III)

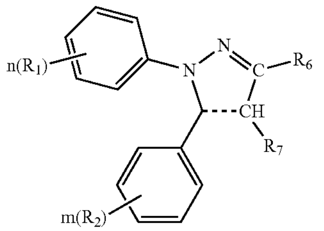

wherein each of $R_1$, $R_2$, n, m, $R_6$ and $R_7$ is as defined for compound (II); and wherein --- designates a single or a double bond and wherein, in case it is a double bond, the carbon atom bearing variant $R_7$ does not carry a bond to a hydrogen atom;

(C) of general formula (IV):

(IV)

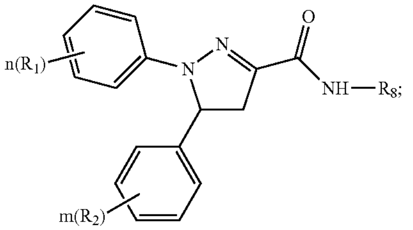

wherein each of $R_1$, $R_2$, n, m and $R_8$ is as defined for compound (II);

(D) of the formula (V):

(V)

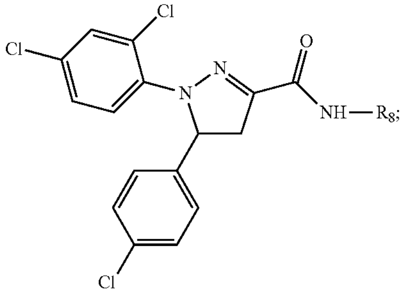

wherein $R_8$ is as defined for compound (II);

(E) of the general formula (VI):

(VI)

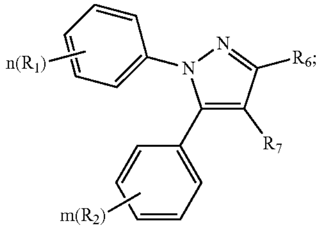

wherein each of $R_1$, $R_2$, n, m, $R_6$ and $R_7$ is as defined for compound (II);

(F) of general formula (VII):

(VII)

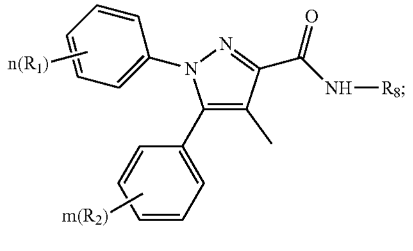

wherein each of $R_1$, $R_2$, n, m and $R_8$ is as defined for compound (II);

(G) of the general formula (VIII):

(VIII)

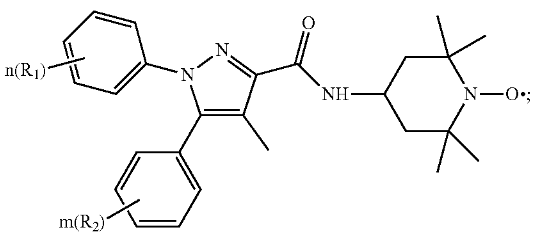

wherein each of $R_1$, $R_2$, n and m is as defined for compound (II);

(H) of the formula (IX):

(IX)

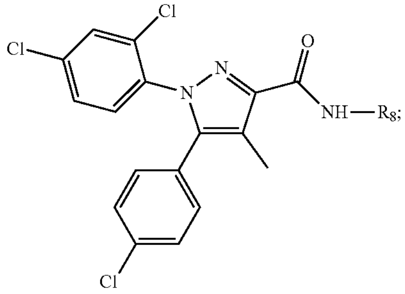

wherein $R_8$ is as defined for compound (II);

(I) of the general formula (XI):

(XI)

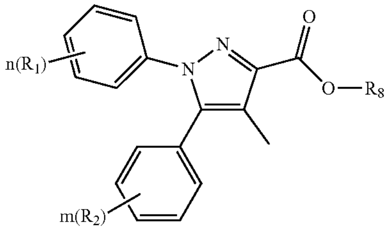

wherein each of $R_1$, $R_2$, n, m and $R_8$ is as defined for compound (II); and wherein optionally $R_8$ is not $C_7$-$C_{12}$alkyl;

(J) of the general formula (XII):

(XII)

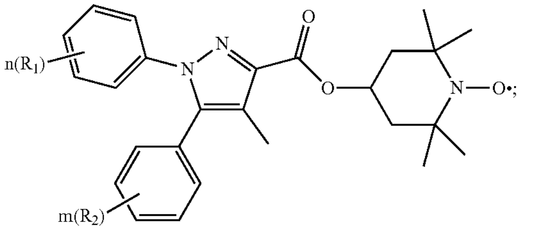

wherein each of $R_1$, $R_2$, n and m is as defined for compound (II);

(K) of the formula (XIII):

(XIII)

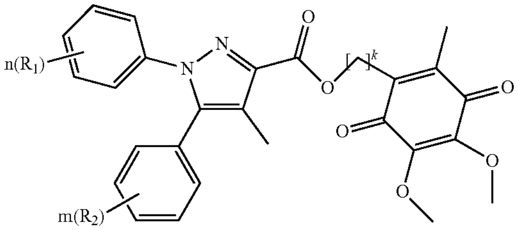

wherein each of $R_1$, $R_2$, n and m is as defined for compound (II); and wherein k is an integer between 0 to 25;

(L) of the general formula (XIV):

(XIV)

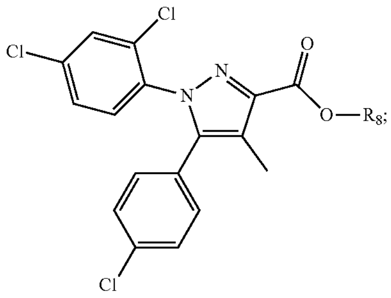

wherein $R_8$ is as defined for compound (II);

(M) of the formula (XVI):

(XVI)

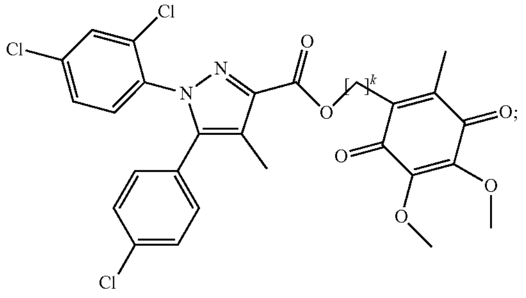

wherein k is an integer between 0 to 25;

(N) of the general formula (XVII):

(XVII)

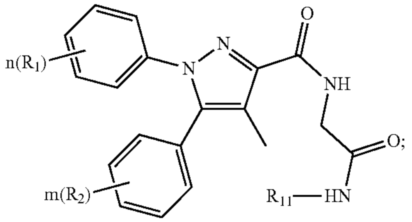

wherein each of $R_1$, $R_2$, n, m, is as defined for compound (II); and wherein $R_{11}$ is selected from —H, —$C_1$-$C_{25}$alkyl, —$C_2$-$C_{25}$alkenyl, —$C_2$-$C_{25}$alkynyl, and —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-Aryl-Cl, idebenonyl-derivative, -pyridine-3-C(═O)—OH and —NR'R"R'", and wherein R', R", R" and $R_{10}$ are as defined for compound (II);

(O) of the general formula (XVIII):

(XVIII)

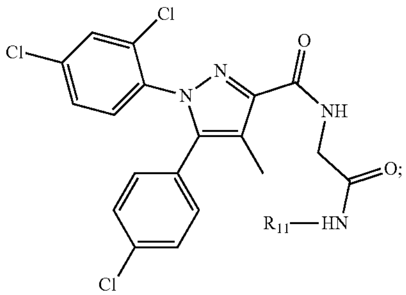

wherein $R_{11}$ is selected from —H, —$C_1$-$C_{25}$alkyl, —$C_2$-$C_{25}$alkenyl, —$C_2$-$C_{25}$alkynyl, and —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-Aryl-Cl, idebenonyl-derivative, -pyridine-3-C(═O)—OH and —NR'R"R'", and wherein R', R", R" and $R_{10}$ are as defined for compound (II);

(P) of the general formula (XIX):

(XIX)

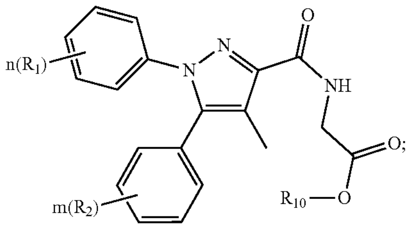

wherein each of $R_1$, $R_2$, n, m, and $R_{10}$ is as defined for compound (II);

(Q) of the general formula (XX):

(XX)

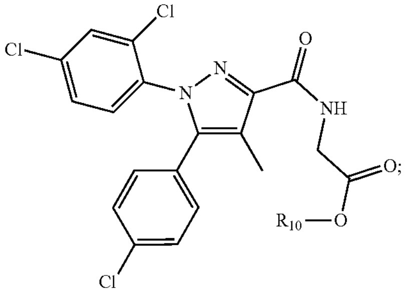

wherein $R_{10}$ is as defined for compound (II);

(R) of the general formula (XXI):

(XXI)

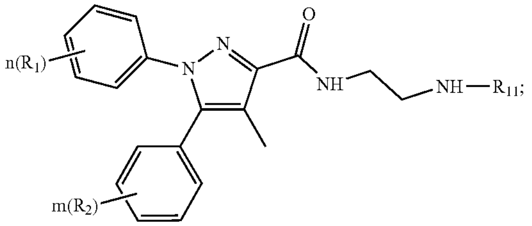

wherein each of $R_1$, $R_2$, n, m, is as defined for compound (II); and wherein $R_{11}$ is selected from —H, —$C_1$-$C_{25}$alkyl, —$C_2$-$C_{25}$alkenyl, —$C_2$-$C_{25}$alkynyl, and —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-Aryl-Cl, idebenonyl-derivative, -pyridine-3-C(═O)—OH and —NR'R"R'", and wherein R', R", R" and $R_{10}$ are as defined for compound (II);

(S) of the general formula (XXII):

(XXII)

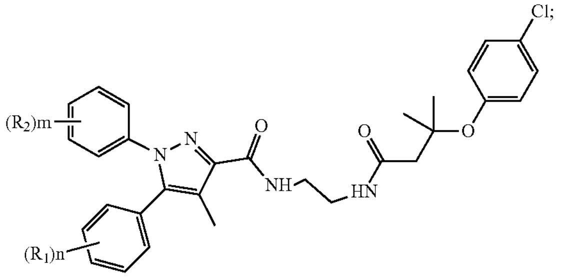

wherein each of $R_1$, $R_2$, n, m, is as defined for compound (II);

(T) of the general formula (XXIII):

(XXIII)

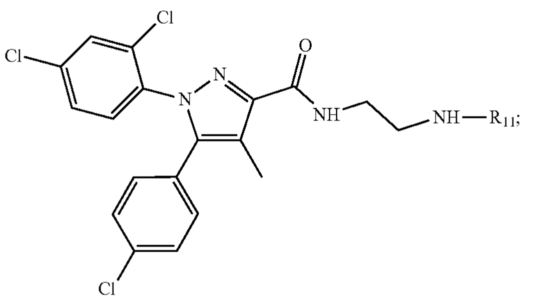

wherein $R_{11}$ is selected from —H, —$C_1$-$C_{25}$alkyl, —$C_2$-$C_{25}$alkenyl, —$C_2$-$C_{25}$alkynyl, and —$C_6$-$C_{10}$aryl, each of which being optionally substituted by at least one functionality selected from an hydroxyl, an amine, a halide, —$C_1$-$C_5$alkyl, —$C_2$-$C_5$alkenyl, —$C_2$-$C_5$alkynyl, —C(═O)—, —C(═O)—$C_1$-$C_{25}$alkyl, —C(═O)—O—$C_1$-$C_5$alkyl, —C(═O)—O—$C_1$-$C_5$alkenyl, —C(═O)—O—$C_1$-$C_5$alkynyl, —C(═O)—NR'R"R'", —C(═O)—$OR_{10}$, —O—$C_1$-$C_5$alkyl, —O—$C_1$-$C_5$alkenyl, —O—$C_1$-$C_5$alkynyl, —S—, —S—$C_1$-$C_5$alkyl, —S—$C_1$-$C_5$alkenyl, —S—$C_1$-$C_5$alkynyl, —$ONO_2$, —$NO_2$, 2,2,6,6-tetramethylpiperidin-1-ol-4-yl, —NHC(═O)$CH_2C(CH_3)_2$—O-Aryl-Cl, idebenonyl-derivative, -pyridine-3-C(═O)—OH and —NR'R"R'", and wherein R', R", R" and $R_{10}$ are as defined for compound (II);

(U) of the general formula (XXV):

(XXV)

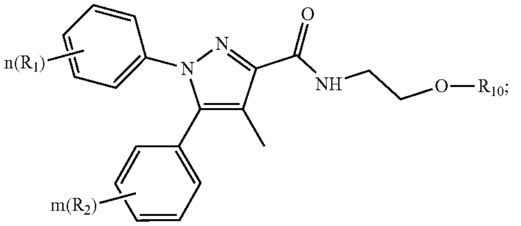

or wherein each of $R_1$, $R_2$, n, m, and $R_{10}$ is as defined for compound (II); or (V) of the general formula (XXVI):

(XXVI)

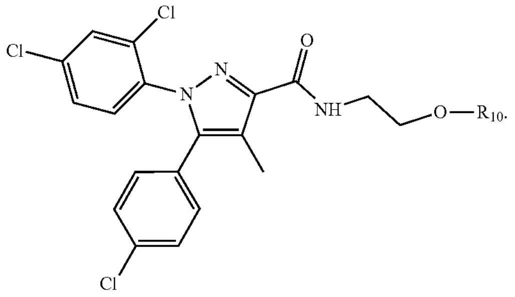

wherein $R_{10}$ is as defined for compound (II).

2. A compound of the formula selected from (A) general formula (XXVII):

(XXVII)

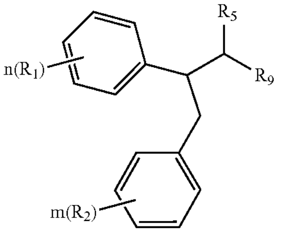

wherein each of $R_1$, $R_2$, n, m is as defined in claim 1;

$R_5$ is absent or selected from H, —$C_1$-$C_3$alkyl, —C(═O)—O—$R_8$, —C(═O)—NR'—$R_8$, halide, CN, and OH; and $R_9$ is selected from —C(═O)—O—$R_8$, —C(═O)—NR'—$R_8$, —NH—C(═O)—O—$R_8$, —NH—C(═O)—NR'—$R_8$, —O—C(═O)—O—$R_8$ and —O—C(═O)—NR'—$R_8$; and where $R_8$ is as defined in claim 1;

(B) general formula (XXVIII):

(XXVIII)

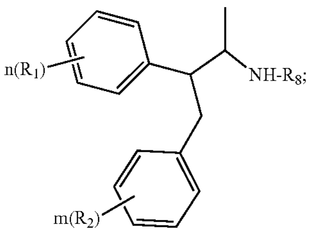

wherein each of $R_1$, $R_2$, n, m, and $R_8$ is as defined for compound (XXVII);

(C) general formula (XXIX):

(XXIX)

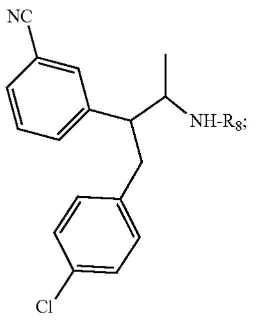

wherein $R_8$ is as defined for compound (XXVII);

(D) general formula (XXX):

(XXX)

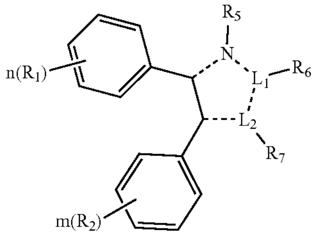

wherein each of $R_1$, $R_2$, n, m, is as defined for compound (XXVII);

one of $L_1$ and $L_2$ is a nitrogen atom and the other of $L_1$ and $L_2$ is a carbon atom being selected from C, CH or $CH_2$;

each of $R_5$, $R_6$ and $R_7$, independently of the other, is absent or selected from —H, $C_1$-$C_3$alkyl, —C(═O)—O—$R_8$, —C(═O)—NR'—$R_8$, halide, CN, OH, and NR'R";

each of R', and R" is independently selected from H, $C_1$-$C_5$alkyl, $C_2$-$C_5$alkenyl, $C_2$-$C_5$alkynyl, —C(═O)—$C_2$-$C_{25}$alkyl, —C(═O)—$C_2$-$C_{25}$alkenyl and $C_5$-$C_{25}$alkynyl;

$R_8$ is as defined for compound (XXVII);

and wherein each bond between C—N, N-$L_1$, $L_1$-$L_2$ and $L_2$-C (designated ---) is a single bond or double bond;

(E) general formula (XXXI):

(XXXI)

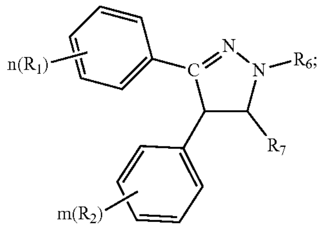

wherein each of $R_1$, $R_2$, n, m, is as defined for compound (XXVII);

each of $R_6$ and $R_7$, independently of the other, is absent or selected from —H, $C_1$-$C_3$alkyl, —C(═O)—O—$R_8$, —C(═O)—NR'—$R_8$, halide, CN, OH, and NR'R";

each of R', and R" is independently selected from H, $C_1$-$C_5$alkyl, $C_2$-$C_5$alkenyl, $C_2$-$C_5$alkynyl, —C(═O)—$C_2$-$C_{25}$alkyl, —C(═O)—$C_2$-$C_{25}$alkenyl and $C_5$-$C_{25}$alkynyl; and wherein $R_8$ is as defined for compound (XXVII);

(F) general formula (XXXII):

(XXXII)

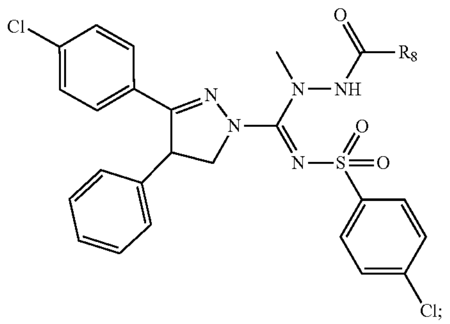

wherein $R_8$ is as defined for compound (XXVII); or (G) general formula (XXXIII):

(XXXIII)

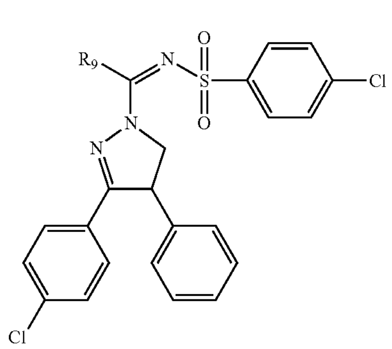

wherein $R_9$ is selected from —O—$R_8$ and —NR'—$R_8$; and wherein $R_8$ is as defined for compound (XXVII).

3. The compound according to claim 1 being a compound of formula (XXXIV):

(XXXIV)

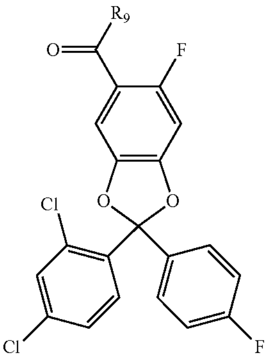

wherein $R_9$ is selected from —O—$R_8$ and —NR'—$R_8$; and wherein $R_8$ is as defined for compound (II);

or a compound of (XXXV):

(XXXV)

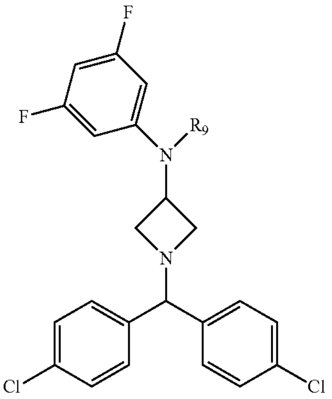

wherein $R_9$ is selected from —O—$R_8$ and —NR'—$R_8$; and wherein $R_8$ is as defined for compound (II);

or a compound of formula (XXXVI):

(XXXVI)

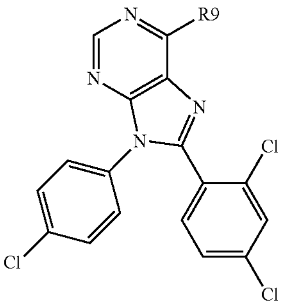

wherein $R_9$ is selected from —O—$R_8$ and —NR'—$R_8$; and wherein $R_8$ is as defined for compound (II);

or a compound of formula (XXXVII):

(XXXVII)

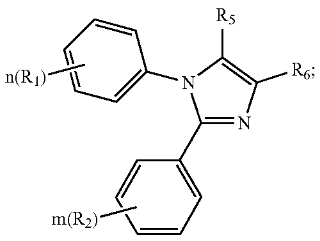

wherein each of $R_1$, $R_2$, n, m, $R_5$ and $R_6$ is as defined for compound (II);

or a compound of formula (XXXVIII):

(XXXVIII)

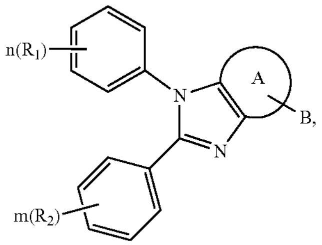

wherein, each of $R_1$, $R_2$, n, m, is as defined for compound (II);

ring A is a 5-, 6-, 7- or 8-membered carbocyclic ring optionally containing between 1 and 3 heteroatoms selected from N, O and S, and optionally substituted by a group B selected from —H, —$C_1$-$C_{25}$alkyl, —$C_2$-$C_{25}$alkynyl, —$C_6$-$C_{10}$aryl, an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(═O)—, —C(═O)—$C_1$-$C_{25}$alkyl, —C(═O)—O—$C_1$-$C_5$alkyl, —C(═O)—O—$C_2$-$C_5$alkenyl, —C(═O)—O—$C_2$-$C_5$alkynyl, —C(═O)—NR'R"R'", —C(═O)—NR'—C(═O)—$C_1$-$C_{25}$alkyl, —C(═O)—NR'—C(═O)—$C_2$-$C_{25}$alkenyl, —C(═O)—NR'—C(═O)—$C_2$-$C_{25}$alkynyl, —C(═O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(═O)—$C_1$-$C_{25}$alkyl, —NH—NH—C(═O)—$C_2$-$C_{25}$alkenyl, —NH—NH—C(═O)—$C_2$-$C_{25}$alkynyl, —NH—NH—C(═O)—$C_6$-$C_{10}$aryl, —NH—NH—C(═O)—$C_3$-$C_{10}$heteroaryl, —NH—$C_1$-$C_{25}$alkyl-C(═O)—OH, —NH—$C_2$-$C_{25}$alkenyl-C(═O)—OH, —NH—$C_2$-$C_{25}$alkynyl-C(═O)—OH, —NH—$C_1$-$C_{25}$alkyl-C(═O)—NR'R"R'", —NH—$C_2$-$C_{25}$alkenyl-C(═O)—NR'R"R'", —NH—$C_2$-$C_{25}$alkynyl-C(═O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(═O)—$C_1$-$C_{25}$alkyl, —NH—$C_2$-$C_{25}$alkenyl-NH—C(═O)—$C_1$-$C_{25}$alkyl, —NH—$C_2$-$C_{25}$alkynyl-NH—C(═O)—$C_1$-$C_{25}$alkyl, —NH—$C_1$-$C_{25}$alkyl-NH—C(═O)—$C_6$-$C_{10}$aryl, —NH—$C_2$-$C_{25}$alkenyl-NH—C(═O)—$C_6$-$C_{10}$aryl, —NH—$C_2$-$C_{25}$alkynyl-NH—C(═O)—$C_6$-$C_{10}$aryl, —NH—$C_1$-$C_{25}$alkyl-NH—C(═O)—$C_3$-$C_{10}$heteroaryl, —NH—$C_2$-$C_{25}$alkenyl-NH—C(═O)—$C_3$-$C_{10}$heteroaryl, —NH—$C_2$-$C_{25}$alkynyl-NH—C(═O)—$C_3$-$C_{10}$heteroaryl, —NH—$C_1$-$C_{25}$alkylene-C(═O)—NR'R"R'", —NH—$C_2$-$C_{25}$alkenylene-C(═O)—NR'R"R'", —NH—$C_2$-$C_{25}$alkynylene-C(═O)—NR'R"R'", —NH—$C_1$-$C_{25}$alkylene-C(═O)—O—$C_1$-$C_{25}$alkyl, —NH—$C_2$-$C_{25}$alkenylene-C(═O)—O—$C_1$-$C_{25}$alkyl, —NH—$C_2$-$C_{25}$alkynylene-C(═O)—O—$C_1$-$C_{25}$alkyl, —NHC(═O)$C_1$-$C_{25}$alkyl, —NHC(═O)$C_2$-$C_{25}$alkenyl, —NHC(═O)$C_2$-$C_{25}$alkynyl, —NHC(═O)$C_1$-$C_{25}$alkylene-NR'R"R'", —NHC(═O)$C_2$-$C_{25}$alkenylene-NR'R"R'", —NHC(═O)$C_2$-$C_{25}$alkynylene-NR'R"R'", —NHC(═O)$C_1$-$C_{25}$alkylene-OH, —NHC(═O)$C_2$-$C_{25}$alkenylene-OH, —NHC(═O)$C_2$-$C_{25}$alkynylene-OH, —NHC(═O)$C_6$-$C_{10}$aryl, —NHC(═O)$C_3$-$C_{10}$heteroaryl, —NHC(═O)$C_1$-$C_{25}$alkylene-$C_6$-$C_{10}$aryl, —NHC(═O)$C_2$-$C_{25}$alkenylene-$C_6$-$C_{10}$aryl, —NHC(═O)$C_2$-$C_{25}$alkynylene-$C_6$-$C_{10}$aryl, —NHC(═O)$C_3$-

$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C($CH_3$)$_2$—O-aryl-Cl, —NHC(=O)$CH_2$C($CH_3$)$_2$—O-aryl-Cl, idebenonyl-derivative, -pyridine-3-C(=O)—OH and —NR'R"R'";

the 5-, 6-, 7- or 8-membered carbocyclic ring is optionally substituted by at least one functionality selected from structures (A) through (H):

(A)

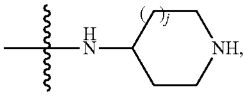

(B)

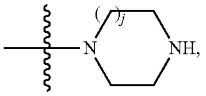

(C)

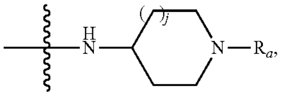

(D)

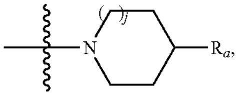

(E)

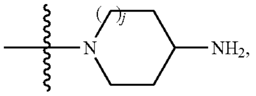

(F)

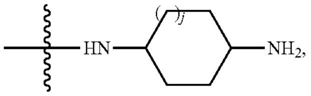

(G)

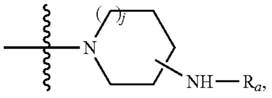

and (H)

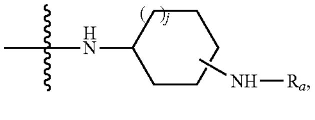

wherein in each functionality (A) through (H), the wavy line indicates point or bond of connectivity, j is 0 or 1 and Ra is selected from —H, —$C_1$-$C_{25}$alkyl, —$C_2$-$C_{25}$alkenyl, —$C_2$-$C_{25}$alkynyl, —C(=O)—$C_6$-$C_{10}$aryl and —C(=O)—$C_3$-$C_{10}$heteroaryl, wherein in functionalities (G) and (H) the pendant-NH—Ra group is present between 1 and 11 times at any position along the carbocycle;

or a compound of the formula (XXXIX):

(XXXIX)

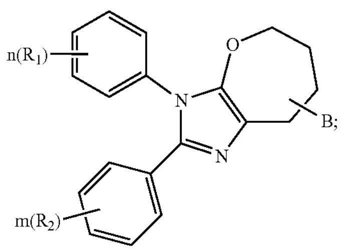

wherein each of $R_1$, $R_2$, n, m, is as defined for compound (II); and

B is selected from —H, —$C_1$-$C_{25}$alkyl, —$C_2$-$C_{25}$alkynyl, —$C_6$-$C_{10}$aryl, an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(=O)—, —C(=O)—$C_1$-$C_{25}$alkyl, —C(=O)—O—$C_1$-$C_5$alkyl, —C(=O)—O—$C_2$-$C_5$alkenyl, —C(=O)—O—$C_2$-$C_5$alkynyl, —C(=O)—NR'R"R'", —C(=O)—NR'—C(=O)—$C_1$-$C_{25}$alkyl, —C(=O)—NR'—C(=O)—$C_2$-$C_{25}$alkenyl, —C(=O)—NR'—C(=O)—$C_2$-$C_{25}$alkynyl, —C(=O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(=O)—$C_1$-$C_{25}$alkyl, —NH—NH—C(=O)—$C_2$-$C_{25}$alkenyl, —NH—NH—C(=O)—$C_2$-$C_{25}$alkynyl, —NH—NH—C(=O)—$C_6$-$C_{10}$aryl, —NH—NH—C(=O)—$C_3$-$C_{10}$heteroaryl, —NH—$C_1$-$C_{25}$alkyl-C(=O)—OH, —NH—$C_2$-$C_{25}$alkenyl-C(=O)—OH, —NH—$C_2$-$C_{25}$alkynyl-C(=O)—OH, —NH—$C_1$-$C_{25}$alkyl-C(=O)—NR'R"R'", —NH—$C_2$-$C_{25}$alkenyl-C(=O)—NR'R"R'", —NH—$C_2$-$C_{25}$alkynyl-C(=O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(=O)—$C_1$-$C_{25}$alkyl, —NH—$C_2$-$C_{25}$alkenyl-NH—C(=O)—$C_1$-$C_{25}$alkyl, —NH—$C_2$-$C_{25}$alkynyl-NH—C(=O)—$C_1$-$C_{25}$alkyl, —NH—$C_1$-$C_{25}$alkyl-NH—C(=O)—$C_6$-$C_{10}$aryl, —NH—$C_2$-$C_{25}$alkenyl-NH—C(=O)—$C_6$-$C_{10}$aryl, —NH—$C_2$-$C_{25}$alkynyl-NH—C(=O)—$C_6$-$C_{10}$aryl, —NH—$C_1$-$C_{25}$alkyl-NH—C(=O)—$C_3$-$C_{10}$heteroaryl, —NH—$C_2$-$C_{25}$alkenyl-NH—C(=O)—$C_3$-$C_{10}$heteroaryl, —NH—$C_2$-$C_{25}$alkynyl-NH—C(=O)—$C_3$-$C_{10}$heteroaryl, —NH—$C_1$-$C_{25}$alkylene-C(=O)—NR'R"R'", —NH—$C_2$-$C_{25}$alkenylene-C(=O)—NR'R"R'", —NH—$C_2$-$C_{25}$alkynylene-C(=O)—NR'R"R'", —NH—$C_1$-$C_{25}$alkylene-C(=O)—O—$C_1$-$C_{25}$alkyl, —NH—$C_2$-$C_{25}$alkenylene-C(=O)—O—$C_1$-$C_{25}$alkyl, —NH—$C_2$-$C_{25}$alkynylene-C(=O)—O—$C_1$-$C_{25}$alkyl, —NHC(=O)$C_1$-$C_{25}$alkyl, —NHC(=O)$C_2$-$C_{25}$alkenyl, —NHC(=O)$C_2$-$C_{25}$alkynyl, —NHC(=O)$C_1$-$C_{25}$alkylene-NR'R"R'", —NHC(=O)$C_2$-$C_{25}$alkenylene-NR'R"R'", —NHC(=O)$C_2$-$C_{25}$alkynylene-NR'R"R'", —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(═O)C(CH$_3$)$_2$—O-aryl-Cl, —NHC(═O)CH$_2$C(CH$_3$)$_2$—O-aryl-Cl, idebenonyl-derivative, -pyridine-3-C(═O)—OH and —NR'R"R'"; or a compound of formula (XXXX):

(XXXX)

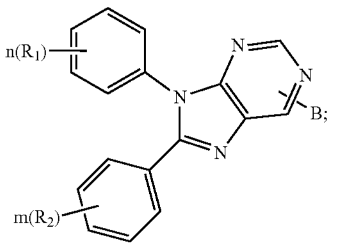

wherein each of R$_1$, R$_2$, n, m, is as defined for compound (II); and

B is selected from —H, —C$_1$-C$_{25}$alkyl, —C$_2$-C$_{25}$alkynyl, —C$_6$-C$_{10}$aryl, an hydroxyl, an amine, a halide, —ONO$_2$, —NO$_2$, —S—, —S—C$_1$-C$_5$alkyl, —S—C$_1$-C$_5$alkenyl, —S—C$_1$-C$_5$alkynyl, —C(═O)—, —C(═O)—C$_1$-C$_{25}$alkyl, —C(═O)—O—C$_1$-C$_5$alkyl, —C(═O)—O—C$_2$-C$_5$alkenyl, —C(═O)—O—C$_2$-C$_5$alkynyl, —C(═O)—NR'R"R'", —C(═O)—NR'—C(═O)—C$_1$-C$_{25}$alkyl, —C(═O)—NR'—C(═O)—C$_2$-C$_{25}$alkenyl, —C(═O)—NR'—C(═O)—C$_2$-C$_{25}$alkynyl, —C(═O)—OR$_{10}$, —O—C$_1$-C$_5$alkyl, —O—C$_1$-C$_5$alkenyl, —O—C$_1$-C$_5$alkynyl, —NH—NH$_2$, —NH—NH—C(═O)—C$_1$-C$_{25}$alkyl, —NH—NH—C(═O)—C$_2$-C$_{25}$alkenyl, —NH—NH—C(═O)—C$_2$-C$_{25}$alkynyl, —NH—NH—C(═O)—C$_6$-C$_{10}$aryl, —NH—NH—C(═O)—C$_3$-C$_{10}$heteroaryl, —NH—C$_1$-C$_{25}$alkyl-C(═O)—OH, —NH—C$_2$-C$_{25}$alkenyl-C(═O)—OH, —NH—C$_2$-C$_{25}$alkynyl-C(═O)—OH, —NH—C$_1$-C$_{25}$alkyl-C(═O)—NR'R"R'", —NH—C$_2$-C$_{25}$alkenyl-C(═O)—NR'R"R'", —NH—C$_2$-C$_{25}$alkynyl-C(═O)—NR'R"R'", —NH—C$_1$-C$_{25}$alkyl-NH$_2$, —NH—C$_2$-C$_{25}$alkenyl-NH$_2$, —NH—C$_2$-C$_{25}$alkynyl-NH$_2$, —NH—C$_1$-C$_{25}$alkyl-NH—C(═O)—C$_1$-C$_{25}$alkyl, —NH—C$_2$-C$_{25}$alkenyl-NH—C(═O)—C$_1$-C$_{25}$alkyl, —NH—C$_2$-C$_{25}$alkynyl-NH—C(═O)—C$_1$-C$_{25}$alkyl, —NH—C$_1$-C$_{25}$alkyl-NH—C(═O)—C$_6$-C$_{10}$aryl, —NH—C$_2$-C$_{25}$alkenyl-NH—C(═O)—C$_6$-C$_{10}$aryl, —NH—C$_2$-C$_{25}$alkynyl-NH—C(═O)—C$_6$-C$_{10}$aryl, —NH—C$_1$-C$_{25}$alkyl-NH—C(═O)—C$_3$-C$_{10}$heteroaryl, —NH—C$_2$-C$_{25}$alkenyl-NH—C(═O)—C$_3$-C$_{10}$heteroaryl, —NH—C$_2$-C$_{25}$alkynyl-NH—C(═O)—C$_3$-C$_{10}$heteroaryl, —NH—C$_1$-C$_{25}$alkylene-C(═O)—NR'R"R'", —NH—C$_2$-C$_{25}$alkenylene-C(═O)—NR'R"R'", —NH—C$_2$-C$_{25}$alkynylene-C(═O)—NR'R"R'", —NH—C$_1$-C$_{25}$alkylene-C(═O)—O—C$_1$-C$_{25}$alkyl, —NH—C$_2$-C$_{25}$alkenylene-C(═O)—O—C$_1$-C$_{25}$alkyl, —NH—C$_2$-C$_{25}$alkynylene-C(═O)—O—C$_1$-C$_{25}$alkyl, —NHC(═O)C$_1$-C$_{25}$alkyl, —NHC(═O)C$_2$-C$_{25}$alkenyl, —NHC(═O)C$_2$-C$_{25}$alkynyl, —NHC(═O)C$_1$-C$_{25}$alkylene-NR'R"R'", —NHC(═O)C$_2$-C$_{25}$alkenylene-NR'R"R'", —NHC(═O)C$_2$-C$_{25}$alkynylene-NR'R"R'", —NHC(═O)C$_1$-C$_{25}$alkylene-OH, —NHC(═O)C$_2$-C$_{25}$alkenylene-OH, —NHC(═O)C$_2$-C$_{25}$alkynylene-OH, —NHC(═O)C$_6$-C$_{10}$aryl, —NHC(═O)C$_3$-C$_{10}$heteroaryl, —NHC(═O)C$_1$-C$_{25}$alkylene-C$_6$-C$_{10}$aryl, —NHC(═O)C$_2$-C$_{25}$alkenylene-C$_6$-C$_{10}$aryl, —NHC(═O)C$_2$-C$_{25}$alkynylene-C$_6$-C$_{10}$aryl, —NHC(═O)C$_3$-C$_{10}$heteroaryl, —NHC(═O)C$_1$-C$_{25}$alkylene-C$_3$-C$_{10}$heteroaryl, —NHC(═O)C$_2$-C$_{25}$alkenylene-C$_3$-C$_{10}$heteroaryl, —NHC(═O)C$_2$-C$_{25}$alkynylene-C$_3$-C$_{10}$heteroaryl, 2,2,6,6-tetramethylpiperidin-1-ol-4-yl free radical, —NHC(═O)C(CH$_3$)$_2$—O-aryl-Cl, —NHC(═O)CH$_2$C(CH$_3$)$_2$—O-aryl-Cl, idebenonyl-derivative, -pyridine-3-C(═O)—OH and —NR'R"R'"; or a compound of formula (XXXXI):

(XXXXI)

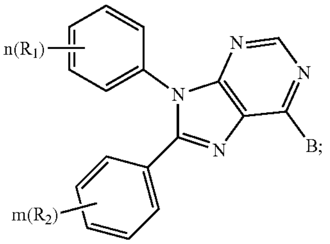

wherein each of R$_1$, R$_2$, n, m, is as defined for compound (II); and

B is selected from —H, —C$_1$-C$_{25}$alkyl, —C$_2$-C$_{25}$alkynyl, —C$_6$-C$_{10}$aryl, an hydroxyl, an amine, a halide, —ONO$_2$, —NO$_2$, —S—, —S—C$_1$-C$_5$alkyl, —S—C$_1$-C$_5$alkenyl, —S—C$_1$-C$_5$alkynyl, —C(═O)—, —C(═O)—C$_1$-C$_{25}$alkyl, —C(═O)—O—C$_1$-C$_5$alkyl, —C(═O)—O—C$_2$-C$_5$alkenyl, —C(═O)—O—C$_2$-C$_5$alkynyl, —C(═O)—NR'R"R'", —C(═O)—NR'—C(═O)—C$_1$-C$_{25}$alkyl, —C(═O)—NR'—C(═O)—C$_2$-C$_{25}$alkenyl, —C(═O)—NR'—C(═O)—C$_2$-C$_{25}$alkynyl, —C(═O)—OR$_{10}$, —O—C$_1$-C$_5$alkyl, —O—C$_1$-C$_5$alkenyl, —O—C$_1$-C$_5$alkynyl, —NH—NH$_2$, —NH—NH—C(═O)—C$_1$-C$_{25}$alkyl, —NH—NH—C(═O)—C$_2$-C$_{25}$alkenyl, —NH—NH—C(═O)—C$_2$-C$_{25}$alkynyl, —NH—NH—C(═O)—C$_6$-C$_{10}$aryl, —NH—NH—C(═O)—C$_3$-C$_{10}$heteroaryl, —NH—C$_1$-C$_{25}$alkyl-C(═O)—OH, —NH—C$_2$-C$_{25}$alkenyl-C(═O)—OH, —NH—C$_2$-C$_{25}$alkynyl-C(═O)—OH, —NH—C$_1$-C$_{25}$alkyl-C(═O)—NR'R"R'", —NH—C$_2$-C$_{25}$alkenyl-C(═O)—NR'R"R'", —NH—C$_2$-C$_{25}$alkynyl-C(═O)—NR'R"R'", —NH—C$_1$-C$_{25}$alkyl-NH$_2$, —NH—C$_2$-C$_{25}$alkenyl-NH$_2$, —NH—C$_2$-C$_{25}$alkynyl-NH$_2$, —NH—C$_1$-C$_{25}$alkyl-NH—C(═O)—C$_1$-C$_{25}$alkyl, —NH—C$_2$-C$_{25}$alkenyl-NH—C(═O)—C$_1$-C$_{25}$alkyl, —NH—C$_2$-C$_{25}$alkynyl-NH—C(═O)—C$_1$-C$_{25}$alkyl, —NH—C$_1$-C$_{25}$alkyl-NH—C(═O)—C$_6$-C$_{10}$aryl, —NH—C$_2$-C$_{25}$alkenyl-NH—C(═O)—C$_6$-C$_{10}$aryl, —NH—C$_2$-C$_{25}$alkynyl-NH—C(═O)—C$_6$-C$_{10}$aryl, —NH—C$_1$-C$_{25}$alkyl-NH—C(═O)—C$_3$-C$_{10}$heteroaryl, —NH—C$_2$-C$_{25}$alkenyl-NH—C(═O)—C$_3$-C$_{10}$heteroaryl, —NH—C$_2$-C$_{25}$alkynyl-NH—C(═O)—C$_3$-C$_{10}$heteroaryl, —NH—C$_1$-C$_{25}$alkylene-C(═O)—NR'R"R'", —NH—C$_2$-C$_{25}$alkenylene-C(═O)—NR'R"R'", —NH—C$_2$-C$_{25}$alkynylene-C(═O)—NR'R"R'", —NH—C$_1$-C$_{25}$alkylene-C(═O)—O—C$_1$-C$_{25}$alkyl, —NH—C$_2$-C$_{25}$alkenylene-C(═O)—O—C$_1$-C$_{25}$alkyl, —NH—C$_2$-C$_{25}$alkynylene-C(═O)—O—C$_1$-C$_{25}$alkyl, —NHC(═O)C$_1$-C$_{25}$alkyl, —NHC(═O)C$_2$-C$_{25}$alkenyl, —NHC(═O)C$_2$-C$_{25}$alkynyl, —NHC(═O)C$_1$-C$_{25}$alkylene-NR'R"R'", —NHC(═O)C$_2$-C$_{25}$alkenylene-NR'R"R'", —NHC(═O)C$_2$-C$_{25}$alkynylene-NR'R"R'", —NHC(═O)C$_1$-C$_{25}$alkylene-OH, —NHC(═O)C$_2$-C$_{25}$alkenylene-OH, —NHC(═O)C$_2$-C$_{25}$alkynylene-OH, —NHC(═O)C$_6$-C$_{10}$aryl, —NHC(═O)C$_3$-C$_{10}$heteroaryl, —NHC(═O)C$_1$-C$_{25}$alkylene-C$_6$-C$_{10}$aryl, —NHC(═O)C$_2$-C$_{25}$alkenylene-C$_6$-C$_{10}$aryl, —NHC(═O)C$_2$-C$_{25}$alkynylene-C$_6$-C$_{10}$aryl, —NHC(═O)C$_3$-C$_{10}$heteroaryl, —NHC(═O)C$_1$-C$_{25}$alkylene-C$_3$-

$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C($CH_3$)$_2$—O-aryl-Cl, —NHC(=O)$CH_2$C($CH_3$)$_2$—O-aryl-Cl, idebenonyl-derivative, -pyridine-3-C(=O)—OH and —NR'R"R'";

or a compound of formula (XXXXII):

(XXXXII)

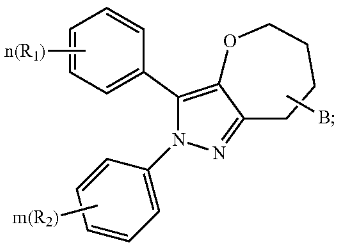

wherein each of $R_1$, $R_2$, n, m, is as defined for compound (II); and

B is selected from —H, —$C_1$-$C_{25}$alkyl, —$C_2$-$C_{25}$alkynyl, —$C_6$-$C_{10}$aryl, an hydroxyl, an amine, a halide, —$ONO_2$, —$NO_2$, —S—, —S—$C_1$-$C_5$alkyl, —S—$C_1$-$C_5$alkenyl, —S—$C_1$-$C_5$alkynyl, —C(=O)—, —C(=O)—$C_1$-$C_{25}$alkyl, —C(=O)—O—$C_1$-$C_5$alkyl, —C(=O)—O—$C_2$-$C_5$alkenyl, —C(=O)—O—$C_2$-$C_5$alkynyl, —C(=O)—NR'R"R'", —C(=O)—NR'—C(=O)—$C_1$-$C_{25}$alkyl, —C(=O)—NR'—C(=O)—$C_2$-$C_{25}$alkenyl, —C(=O)—NR'—C(=O)—$C_2$-$C_{25}$alkynyl, —C(=O)—$OR_{10}$, —O—$C_1$-$C_5$alkyl, —O—$C_1$-$C_5$alkenyl, —O—$C_1$-$C_5$alkynyl, —NH—$NH_2$, —NH—NH—C(=O)—$C_1$-$C_{25}$alkyl, —NH—NH—C(=O)—$C_2$-$C_{25}$alkenyl, —NH—NH—C(=O)—$C_2$-$C_{25}$alkynyl, —NH—NH—C(=O)—$C_6$-$C_{10}$aryl, —NH—NH—C(=O)—$C_3$-$C_{10}$heteroaryl, —NH—$C_1$-$C_{25}$alkyl-C(=O)—OH, —NH—$C_2$-$C_{25}$alkenyl-C(=O)—OH, —NH—$C_2$-$C_{25}$alkynyl-C(=O)—OH, —NH—$C_1$-$C_{25}$alkyl-C(=O)—NR'R"R'", —NH—$C_2$-$C_{25}$alkenyl-C(=O)—NR'R"R'", —NH—$C_2$-$C_{25}$alkynyl-C(=O)—NR'R"R'", —NH—$C_1$-$C_{25}$alkyl-$NH_2$, —NH—$C_2$-$C_{25}$alkenyl-$NH_2$, —NH—$C_2$-$C_{25}$alkynyl-$NH_2$, —NH—$C_1$-$C_{25}$alkyl-NH—C(=O)—$C_1$-$C_{25}$alkyl, —NH—$C_2$-$C_{25}$alkenyl-NH—C(=O)—$C_1$-$C_{25}$alkyl, —NH—$C_2$-$C_{25}$alkynyl-NH—C(=O)—$C_1$-$C_{25}$alkyl, —NH—$C_1$-$C_{25}$alkyl-NH—C(=O)—$C_6$-$C_{10}$aryl, —NH—$C_2$-$C_{25}$alkenyl-NH—C(=O)—$C_6$-$C_{10}$aryl, —NH—$C_2$-$C_{25}$alkynyl-NH—C(=O)—$C_6$-$C_{10}$aryl, —NH—$C_1$-$C_{25}$alkyl-NH—C(=O)—$C_3$-$C_{10}$heteroaryl, —NH—$C_2$-$C_{25}$alkenyl-NH—C(=O)—$C_3$-$C_{10}$heteroaryl, —NH—$C_2$-$C_{25}$alkynyl-NH—C(=O)—$C_3$-$C_{10}$heteroaryl, —NH—$C_1$-$C_{25}$alkylene-C(=O)—NR'R"R'", —NH—$C_2$-$C_{25}$alkenylene-C(=O)—NR'R"R'", —NH—$C_2$-$C_{25}$alkynylene-C(=O)—NR'R"R'", —NH—$C_1$-$C_{25}$alkylene-C(=O)—O—$C_1$-$C_{25}$alkyl, —NH—$C_2$-$C_{25}$alkenylene-C(=O)—O—$C_1$-$C_{25}$alkyl, —NH—$C_2$-$C_{25}$alkynylene-C(=O)—O—$C_1$-$C_{25}$alkyl, —NHC(=O)$C_1$-$C_{25}$alkyl, —NHC(=O)$C_2$-$C_{25}$alkenyl, —NHC(=O)$C_2$-$C_{25}$alkynyl, —NHC(=O)$C_1$-$C_{25}$alkylene-NR'R"R'", —NHC(=O)$C_2$-$C_{25}$alkenylene-NR'R"R'", —NHC(=O)$C_2$-$C_{25}$alkynylene-NR'R"R'", —NHC(=O)$C_1$-$C_{25}$alkylene-OH, —NHC(=O)$C_2$-$C_{25}$alkenylene-OH, —NHC(=O)$C_2$-$C_{25}$alkynylene-OH, —NHC(=O)$C_6$-$C_{10}$aryl, —NHC(=O)$C_3$-$C_{10}$heteroaryl, —NHC(=O)$C_1$-$C_{25}$alkylene-$C_6$-$C_{10}$aryl, —NHC(=O)$C_2$-$C_{25}$alkenylene-$C_6$-$C_{10}$aryl, —NHC(=O)$C_2$-$C_{25}$alkynylene-$C_6$-$C_{10}$aryl, —NHC(=O)$C_3$-$C_{10}$heteroaryl, —NHC(=O)$C_1$-$C_{25}$alkylene-$C_3$-$C_{10}$heteroaryl, —NHC(=O)$C_2$-$C_{25}$alkenylene-$C_3$-$C_{10}$heteroaryl, —NHC(=O)$C_2$-$C_{25}$alkynylene-$C_3$-$C_{10}$heteroaryl, 2,2,6,6-tetramethylpiperidin-1-ol-4-yl free radical, —NHC(=O)C($CH_3$)$_2$—O-aryl-Cl, —NHC(=O)$CH_2$C($CH_3$)$_2$—O-aryl-Cl, idebenonyl-derivative, -pyridine-3-C(=O)—OH and —NR'R"R'";

or any one compound of:

A

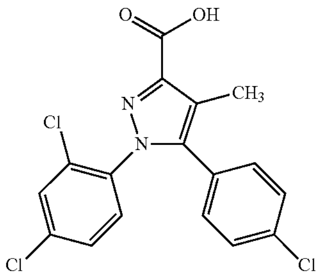

B

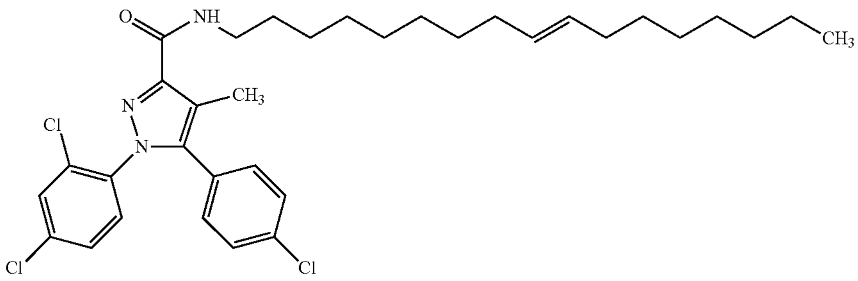

-continued
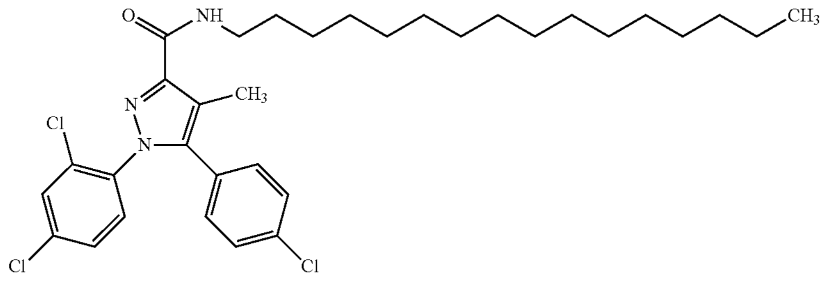
C
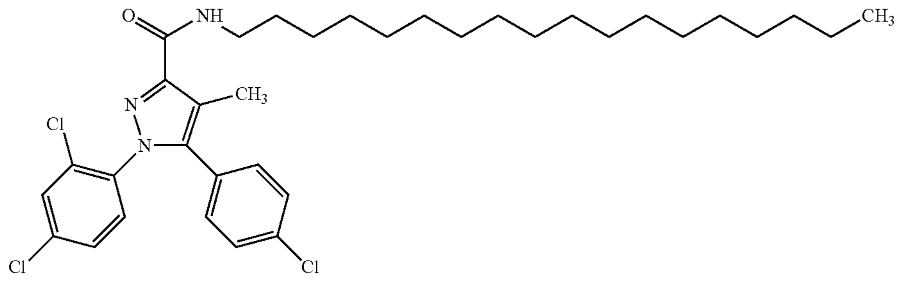
D
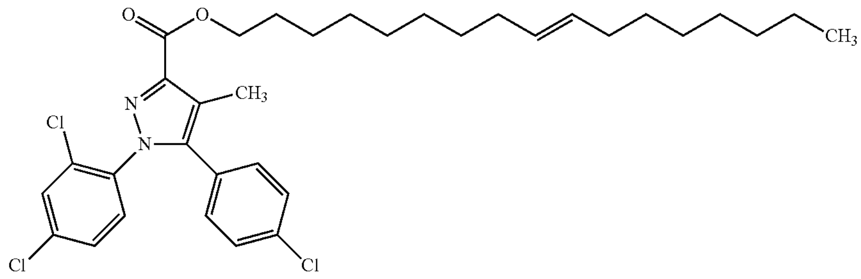
E
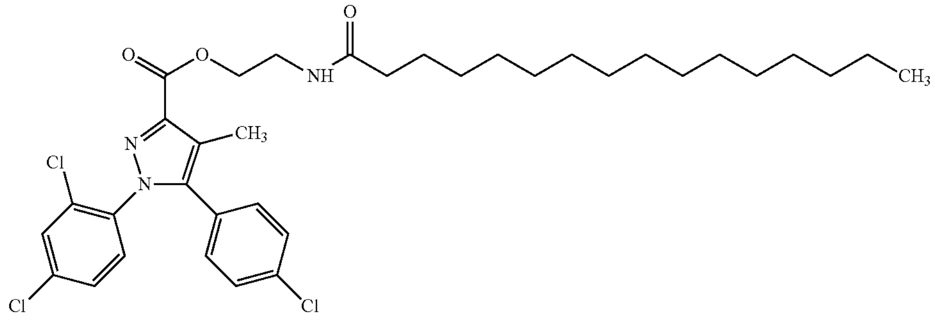
F
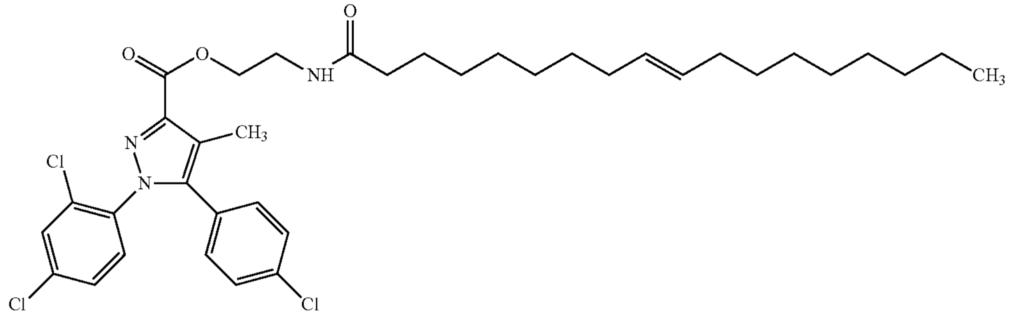
G -continued
H
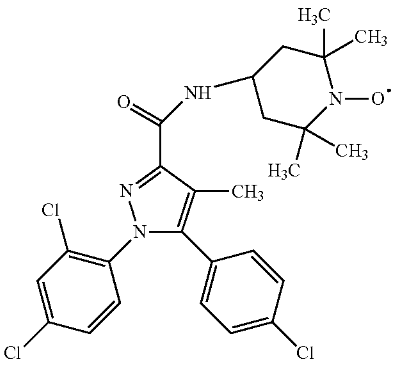
I
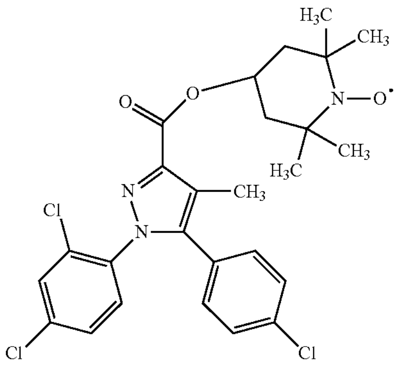
J
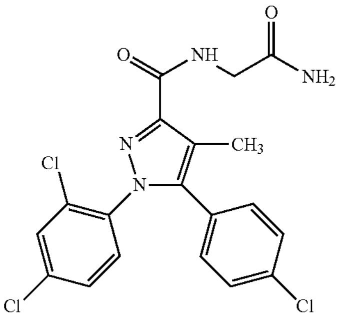
K
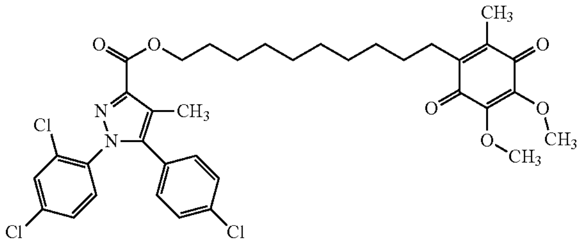
L
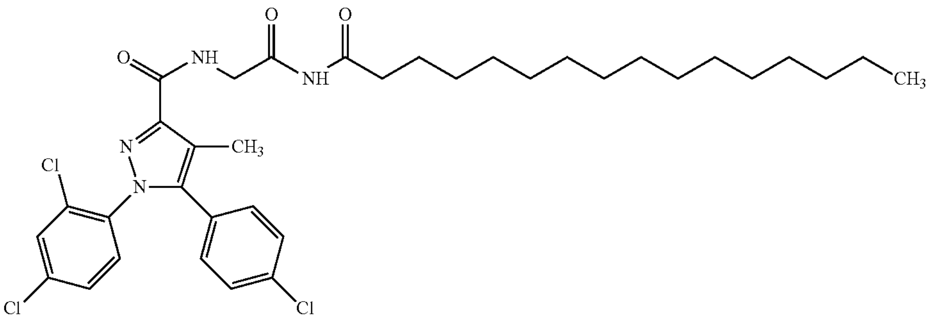
M
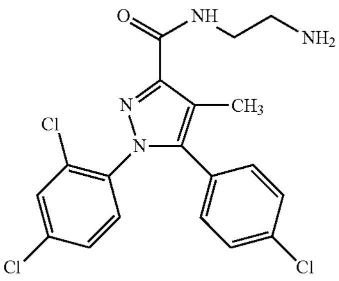
N
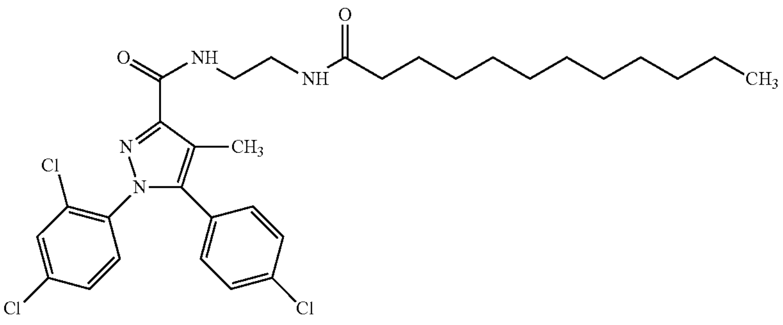

-continued
O
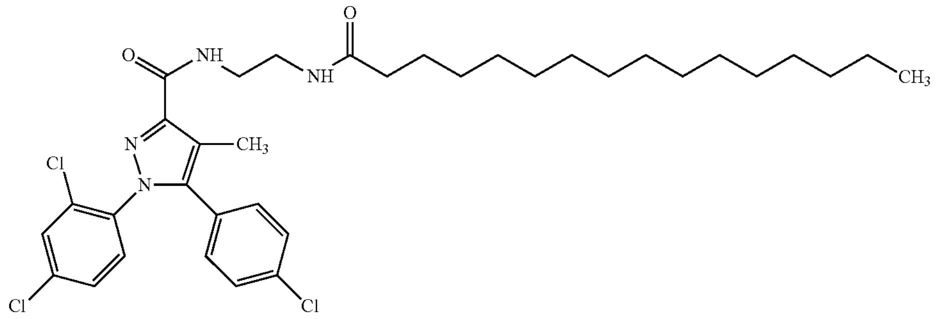
P
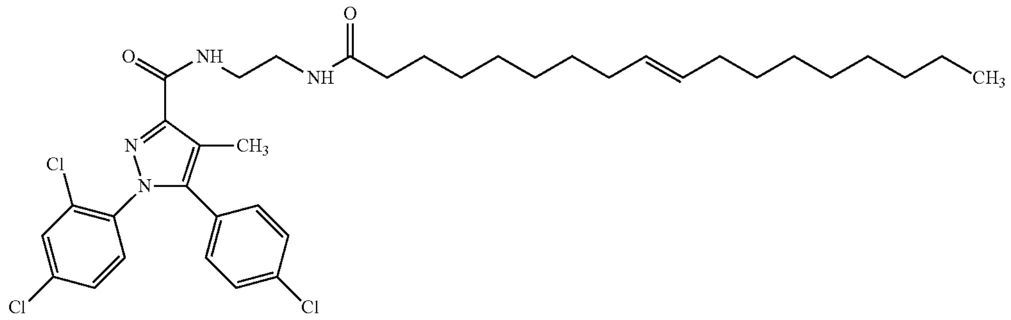
Q
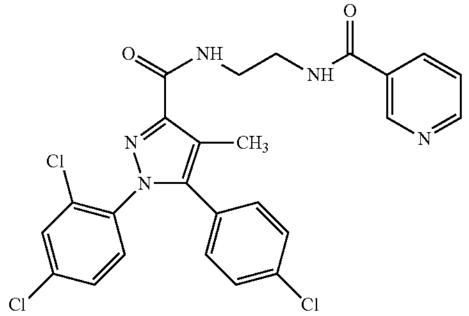
R
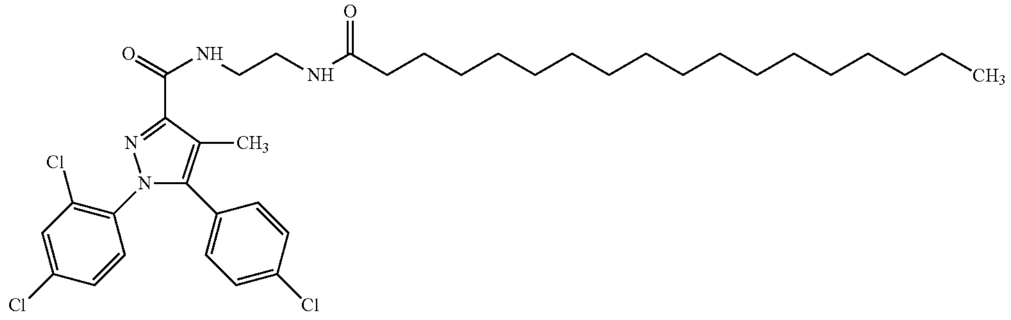
S
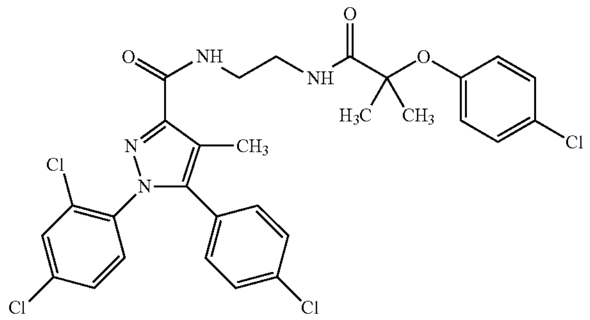

-continued
T
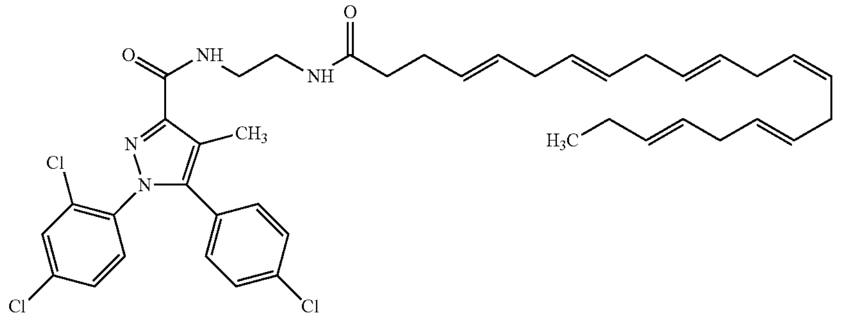
U
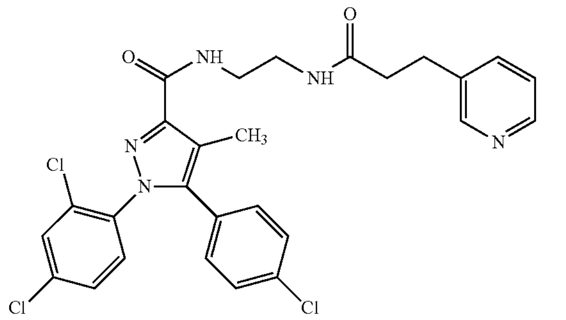
V
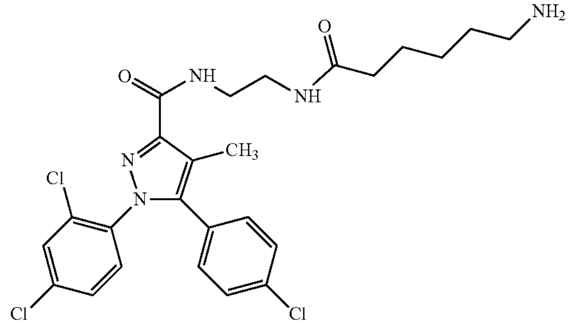
W
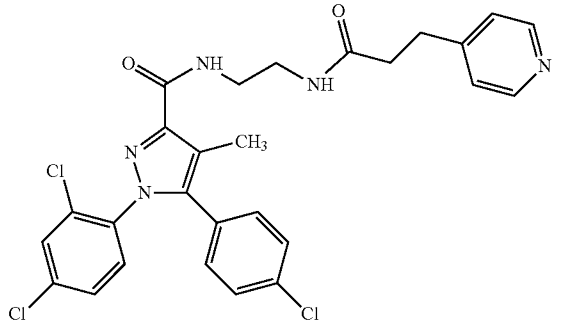
X
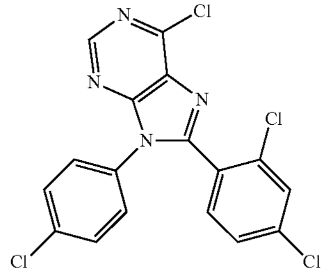
Y
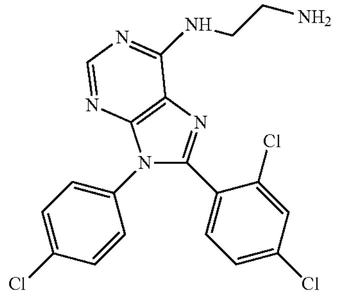
Z
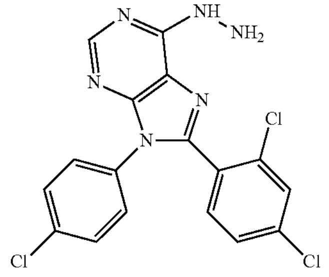
AA
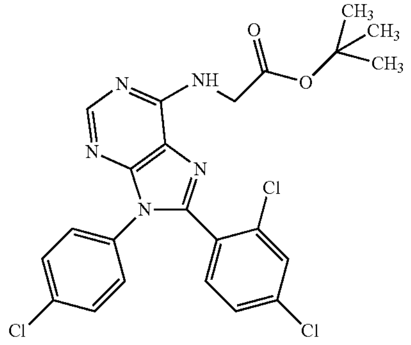
AB
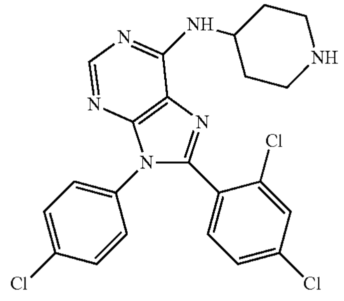

-continued
AC
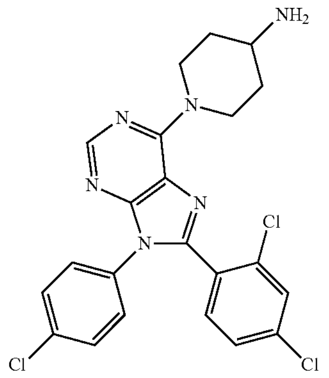
AD
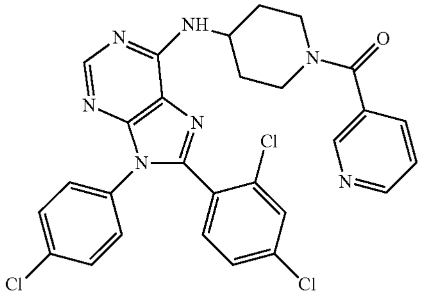
AE
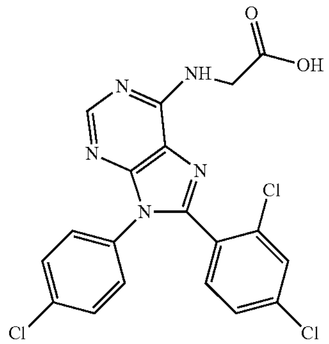
AF
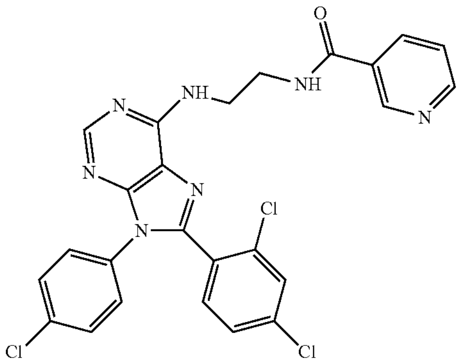
AG
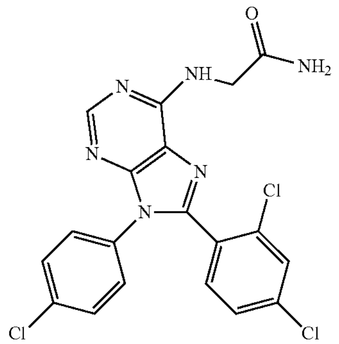
AH
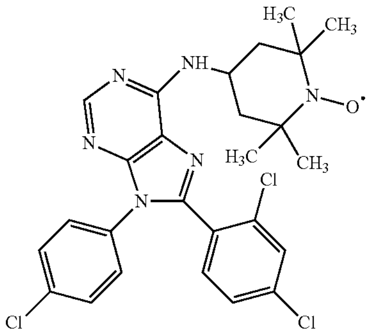
AI
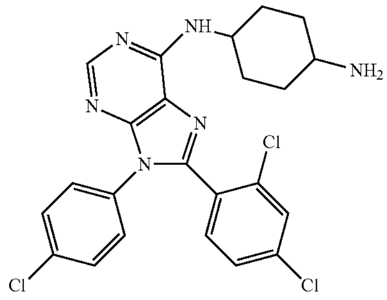
AJ
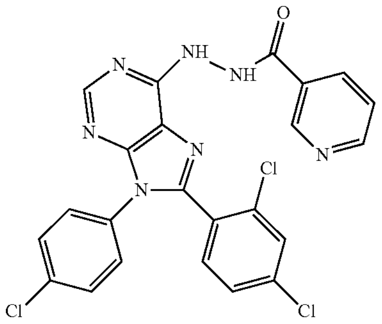

-continued
AK
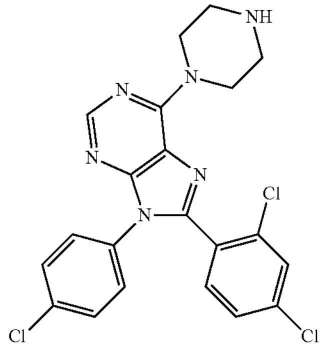
AL
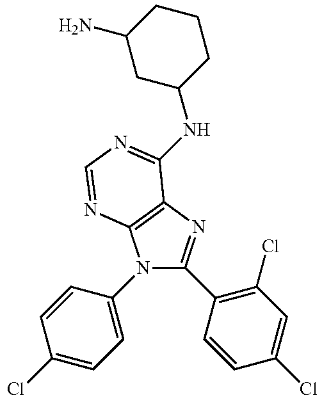
AM
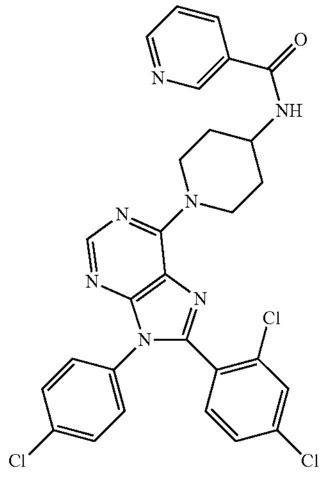
AN
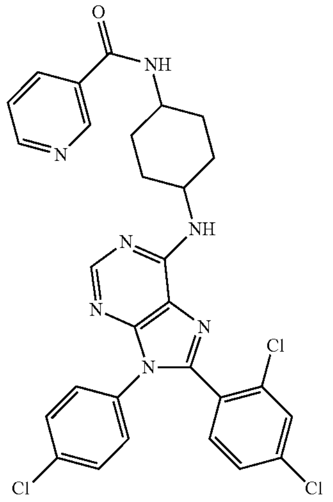
AO
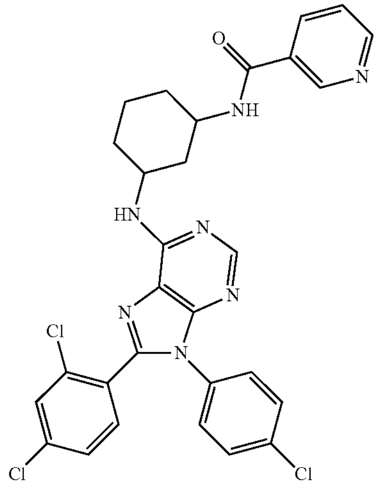
AP
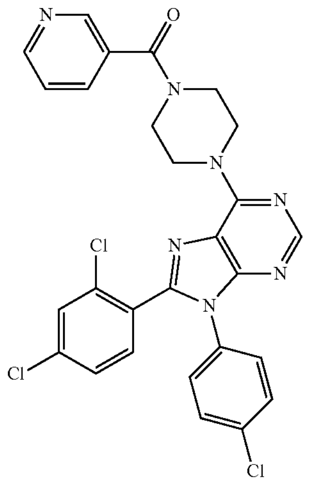

-continued
AQ
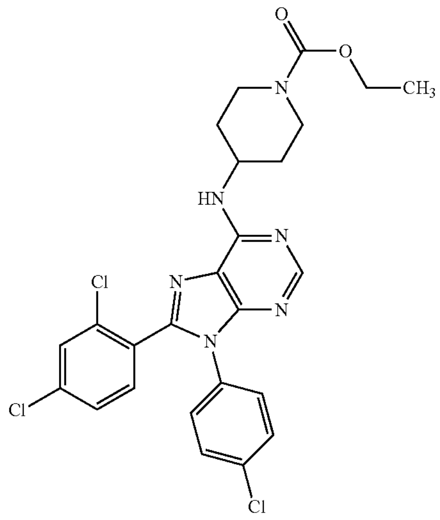
AR
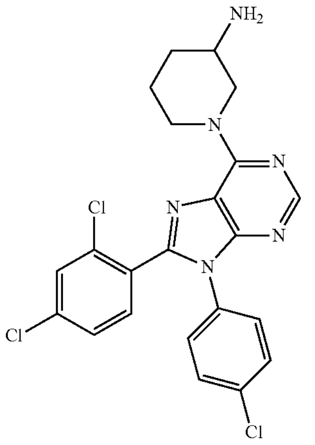
AS
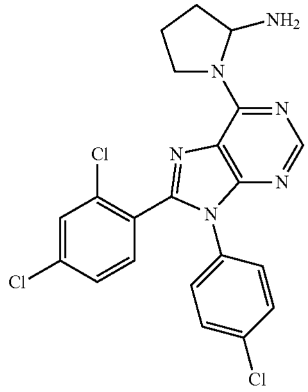
AT
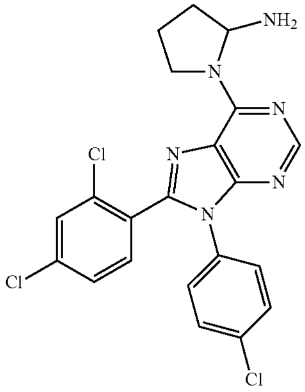
AU
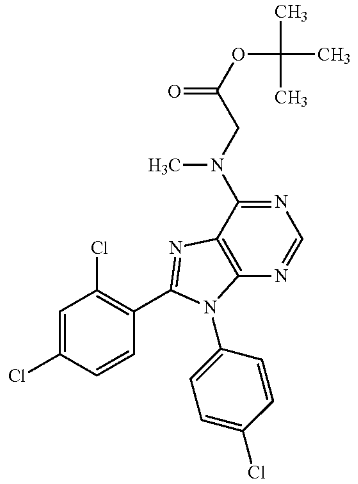
AV
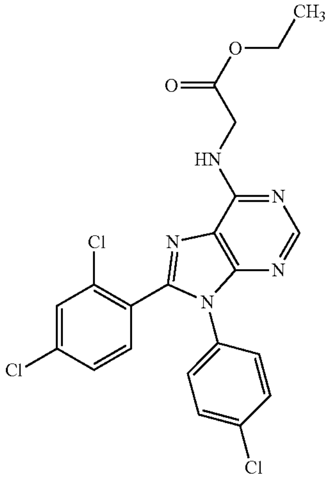

-continued
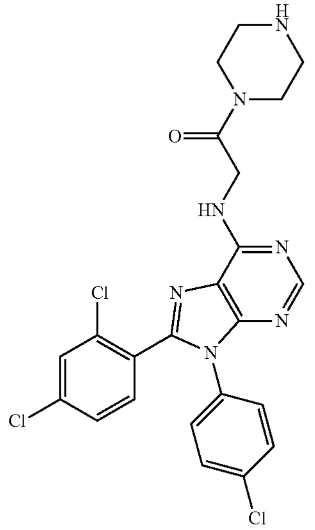
AW
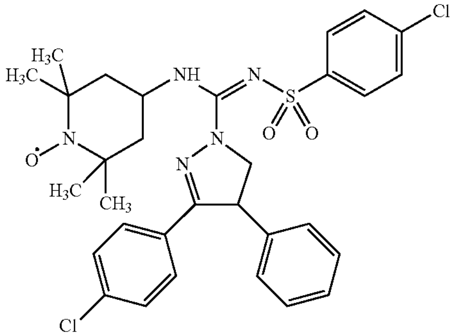
AX
AY
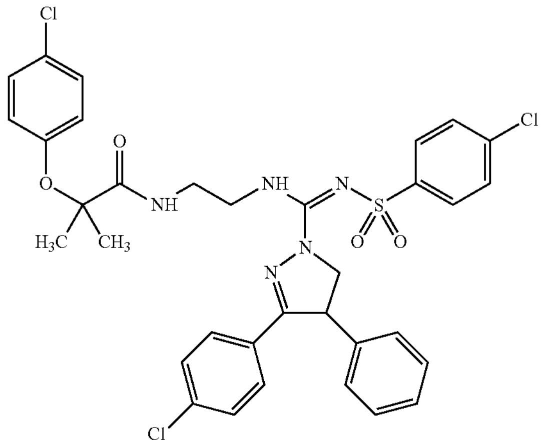
AZ
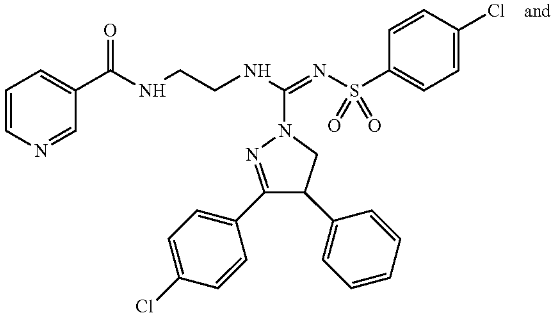
and
BB
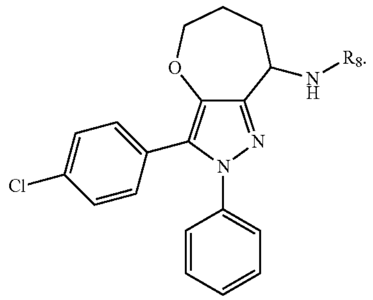
wherein $R_8$ is as defined in claim 1.

4. A compound having any one of the structures:
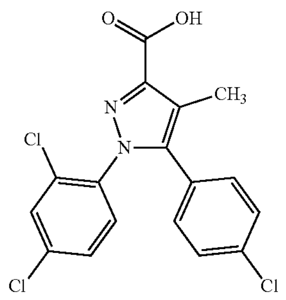
A
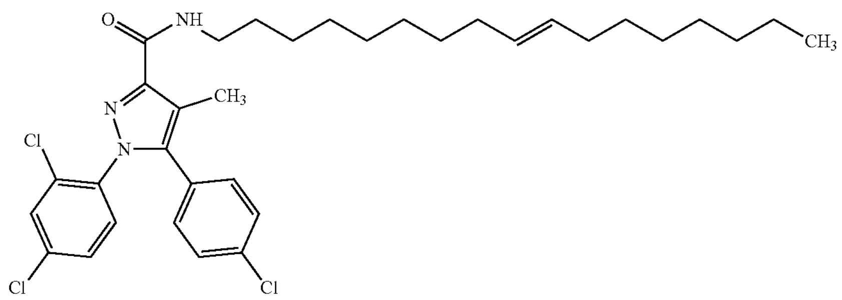
B
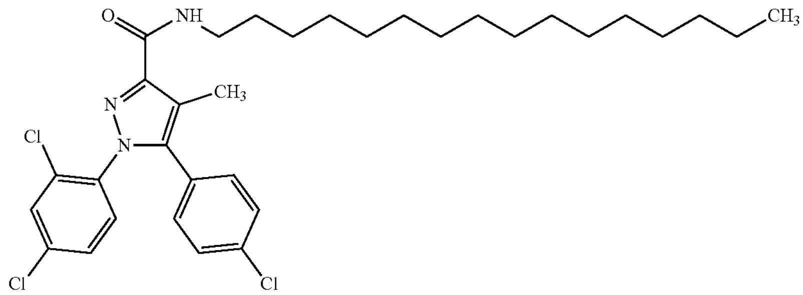
C
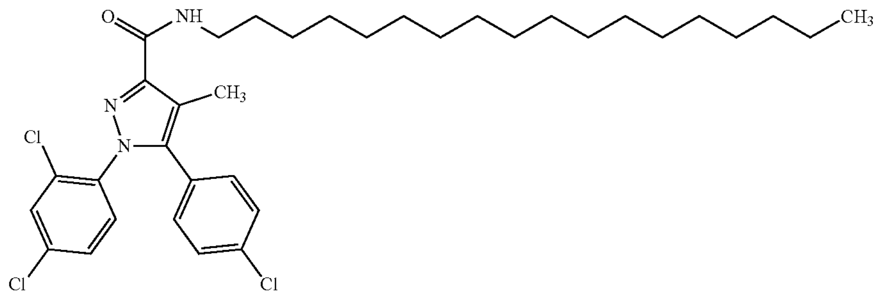
D
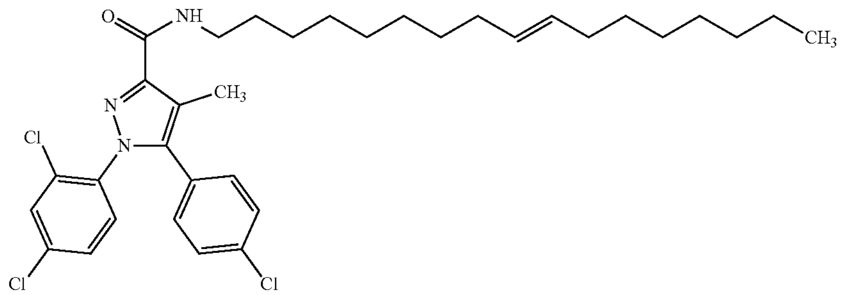
E -continued
F
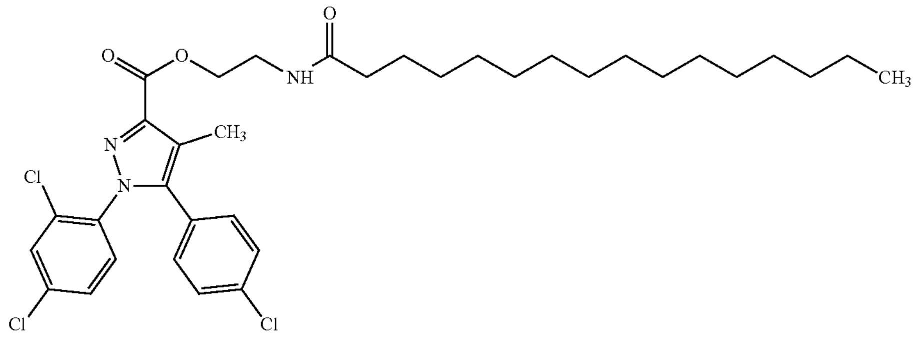
G
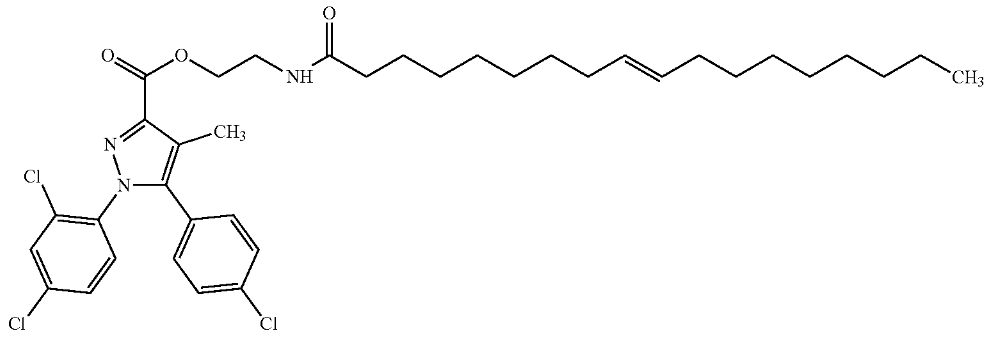
H
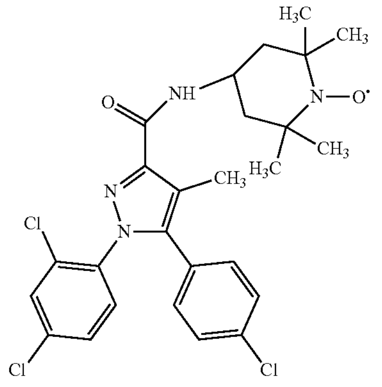
I
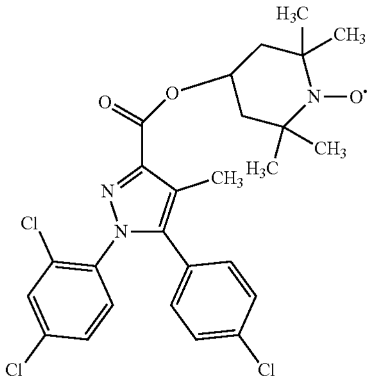
J
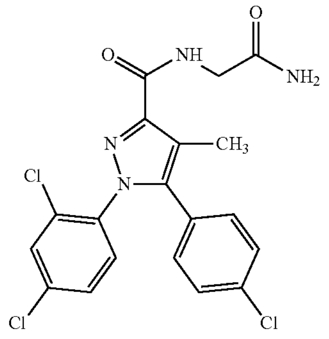

-continued
K
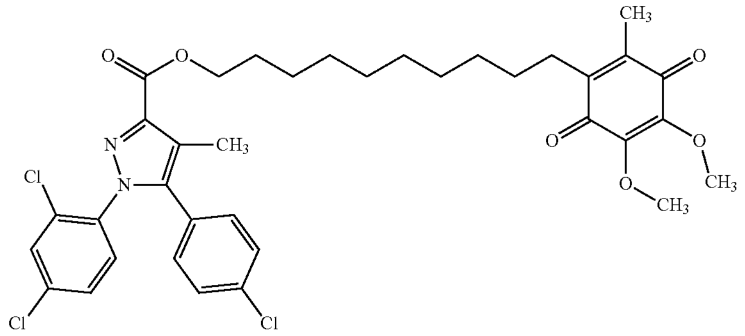
L
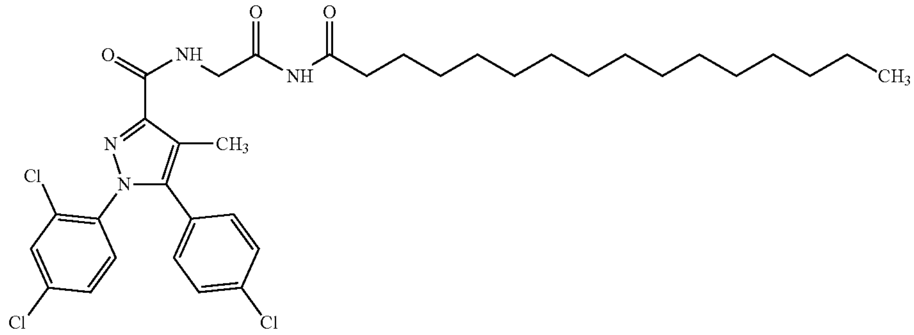
M
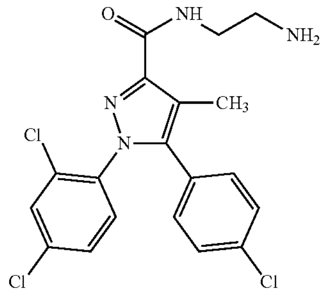
N
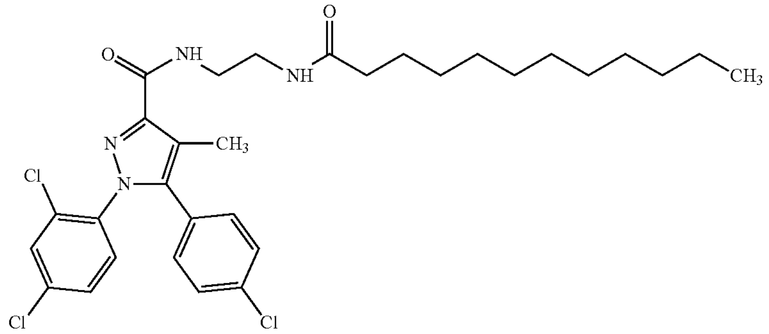
O
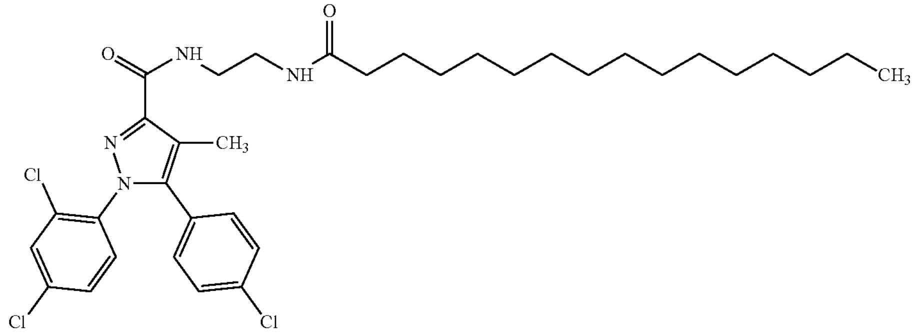

-continued
P
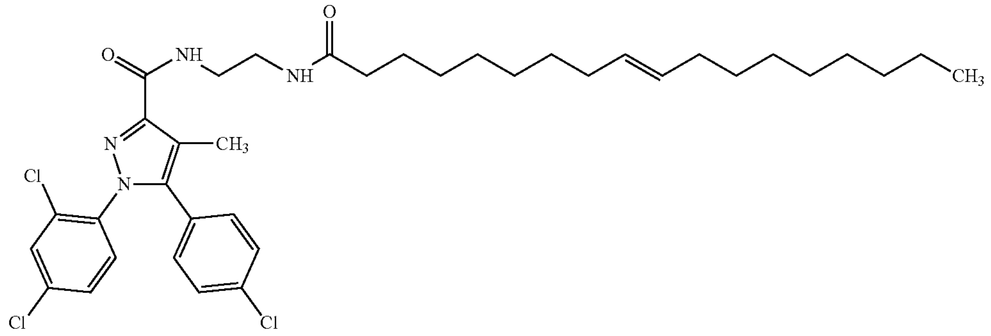
Q
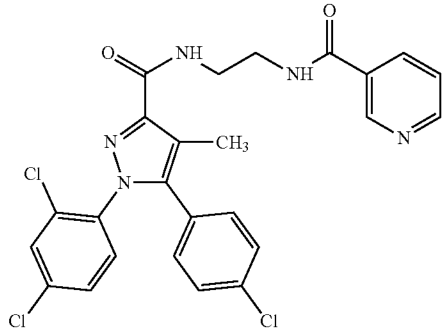
R
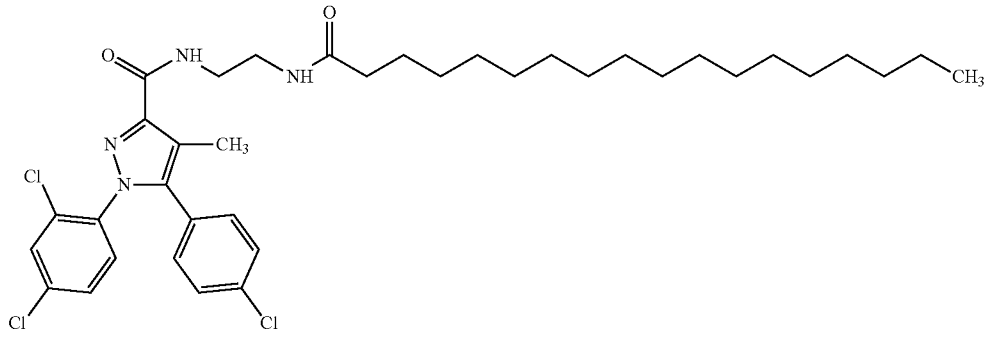
S
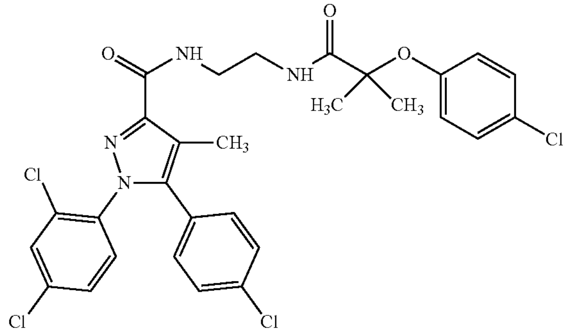

-continued
T
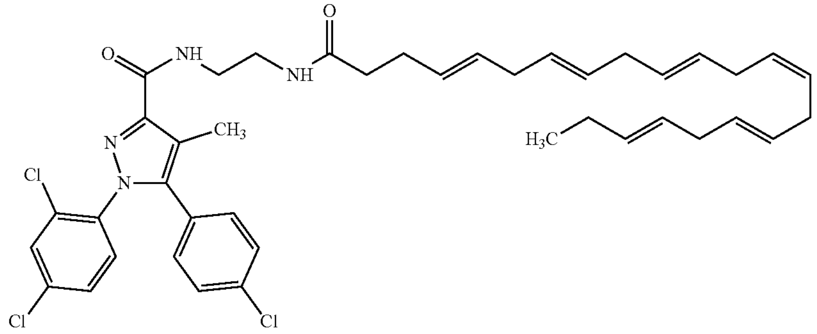
U
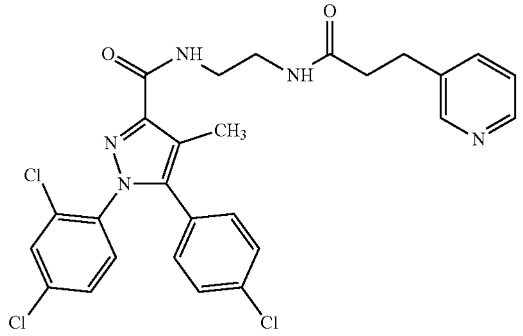
V
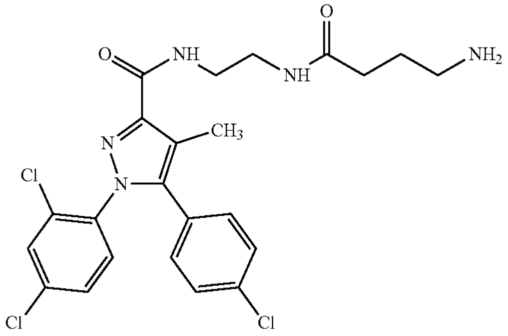
W
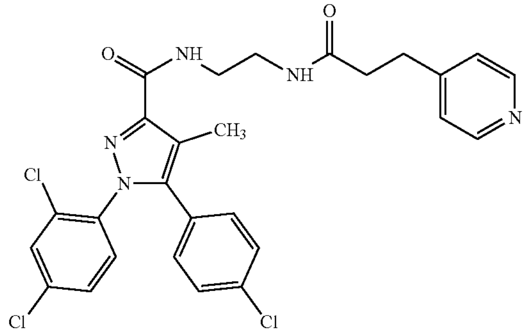
X
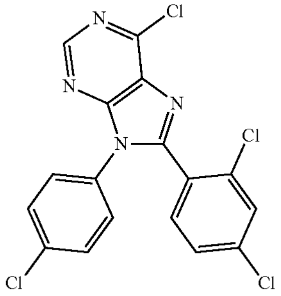
Y
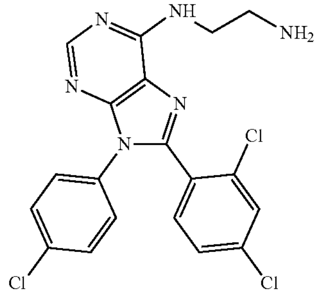
Z
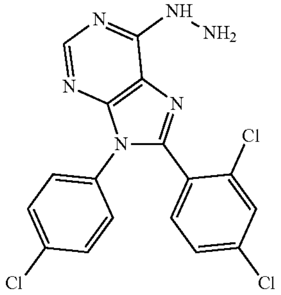

-continued
AA
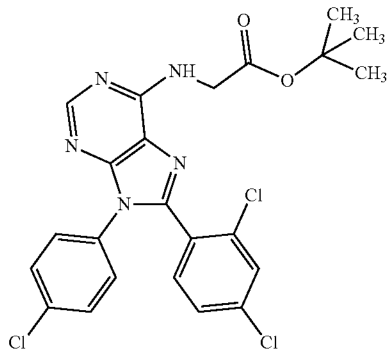
AB
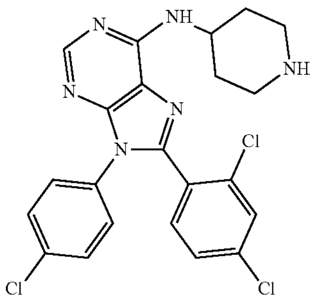
AC
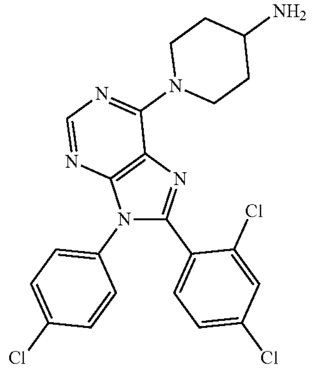
AD
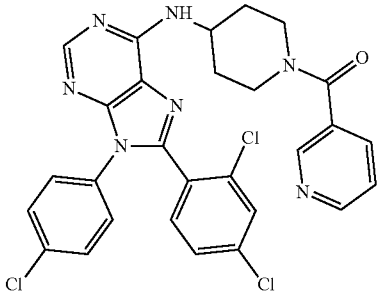
AE
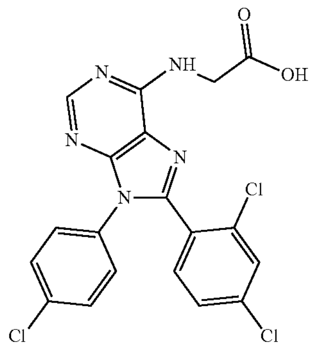
AF
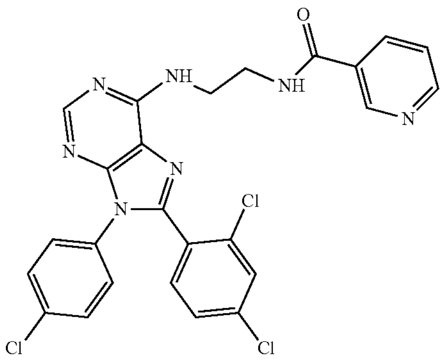
AG
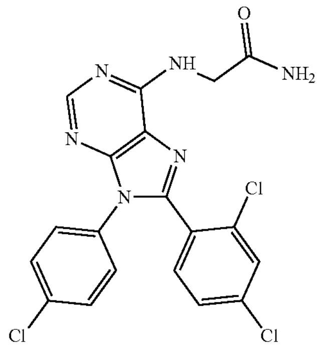
AH
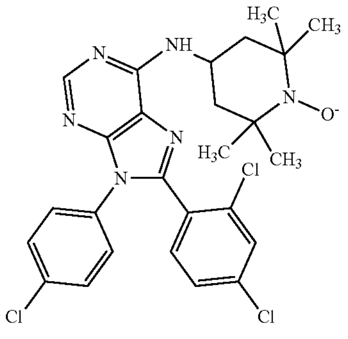

-continued
AJ
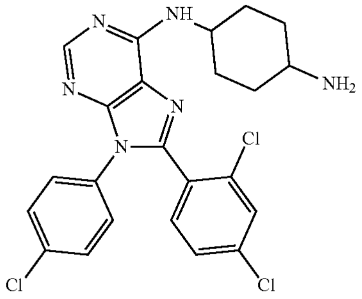
AI
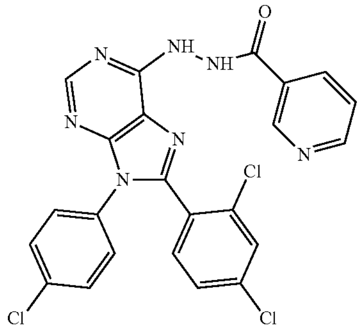
AK
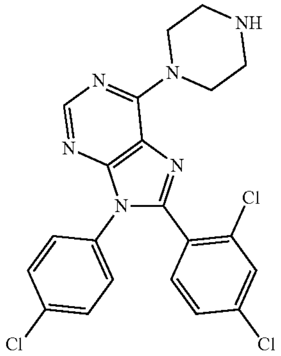
AL
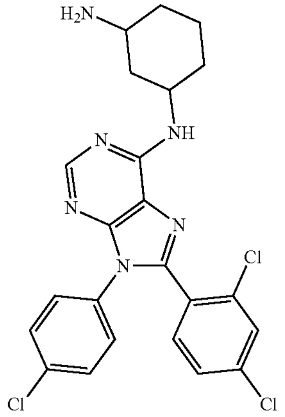
AM
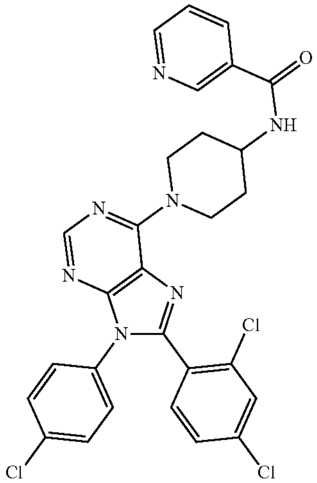
AN
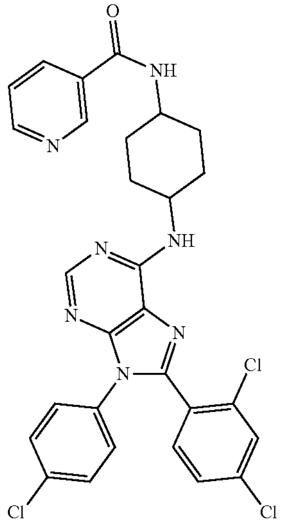

-continued
AO
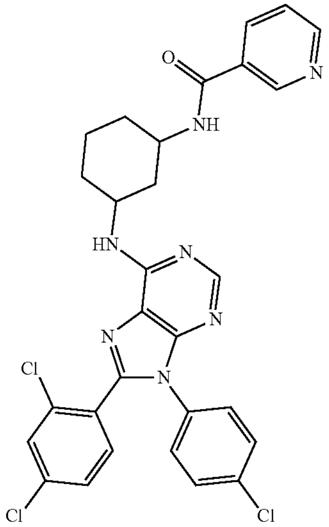
AP
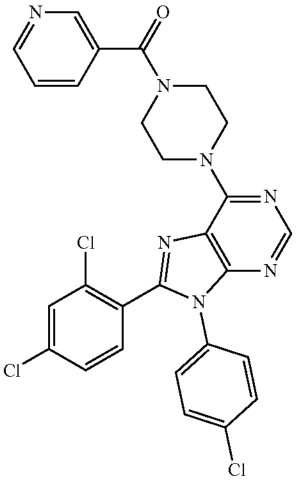
AQ
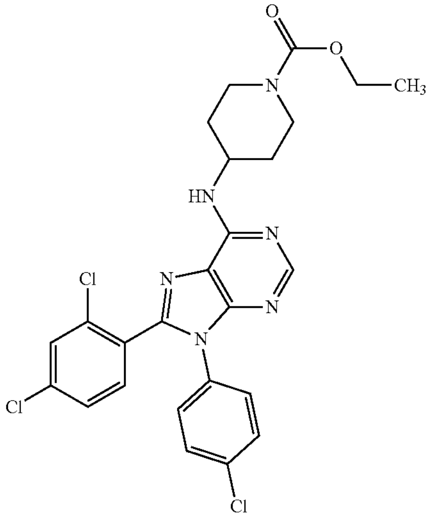
AR
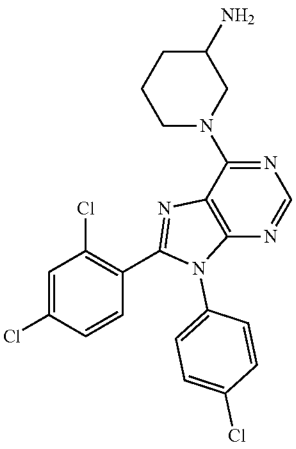
AS
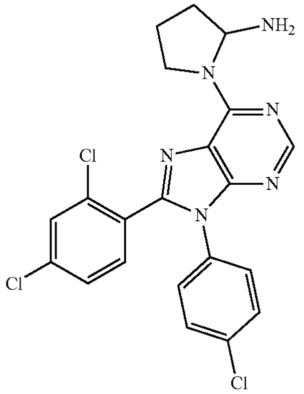
AT
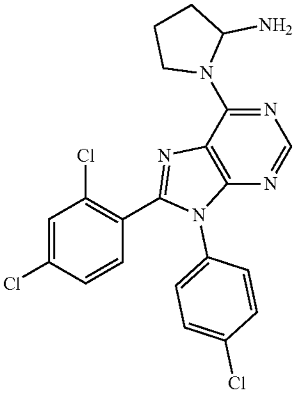

-continued
AU
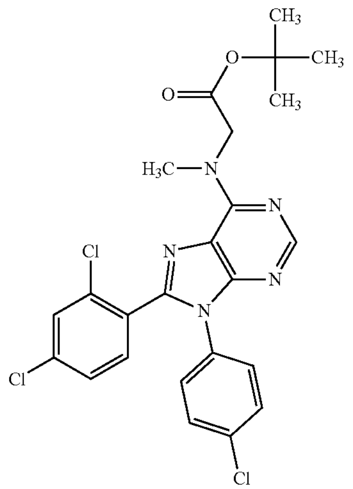
AV
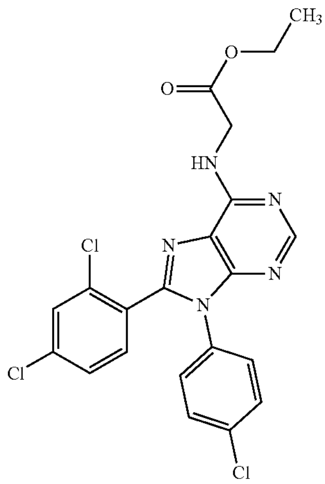
AW
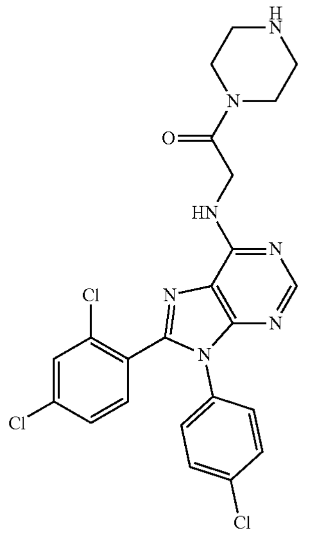
AX
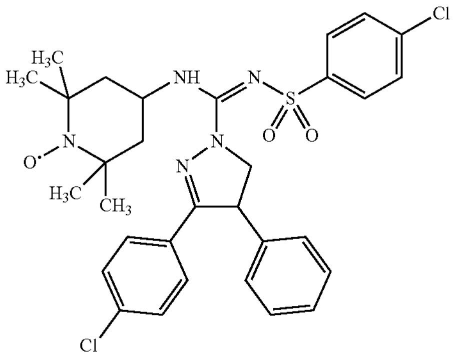
AY
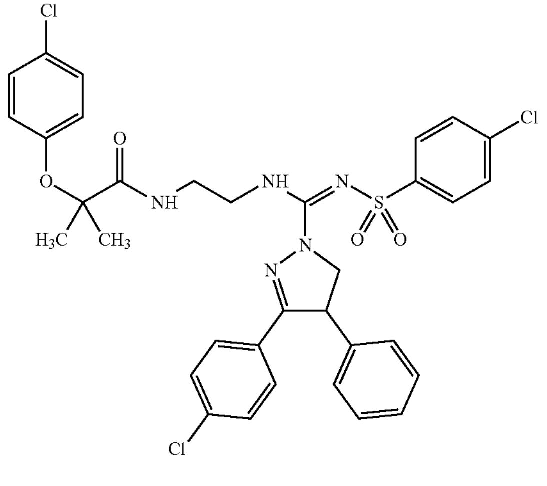
AZ
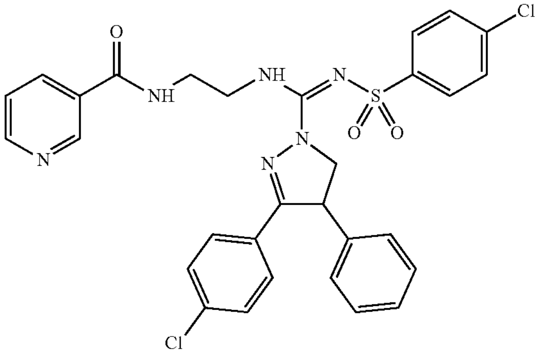
and -continued

BB

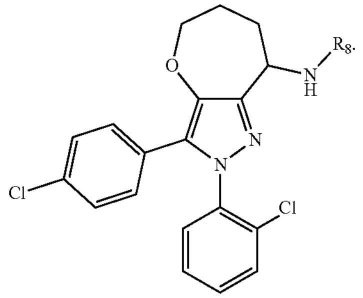

wherein $R_8$ is as defined in claim 1.

5. The compound according to claim 1, wherein the compound is a modulator of peripheral cannabinoid receptors.

6. The compound according to claim 4, wherein the peripheral cannabinoid receptors is selected from peripherally restricted $CB_1$ receptors and peripherally restricted $CB_2$ receptors.

7. The compound according to claim 1, wherein the compound is a neutral antagonist of peripheral cannabinoid receptors.

8. The compound according to claim 1, wherein the compound is an inverse agonist of peripheral cannabinoid receptors.

9. The compound according to claim 1, wherein the compound is an inhibitor of peripheral cannabinoid receptors.

10. A compound according to claim 1, being a peripherally restricted $CB_1$ receptor inverse agonist.

11. A pharmaceutical composition comprising a compound according to claim 1.

12. A nanocarrier comprising at least one compound of claim 1.

13. A method of treating a metabolic syndrome and disorders, the method comprises administering to a human or animal subject an amount of a compound of claim 1.

14. The method according to claim 12, wherein the metabolic syndrome or disorders are selected from obesity, insulin resistance, diabetes, coronary heart disease, liver cirrhosis and cancer.

15. A method of treating a subject to reduce body fat, or to reduce body weight, or to treat insulin resistance, or to treat diabetes, or to reduce or control high blood pressure, or to improve a poor lipid profile with elevated LDL cholesterol, low HDL cholesterol, and elevated triglycerides, or to treat a metabolic syndrome, the method comprising administering to the subject at least one compound according to claim 1.

* * * * *